United States Patent
Lee et al.

(10) Patent No.: US 9,757,402 B2
(45) Date of Patent: Sep. 12, 2017

(54) METHOD FOR MEASURING CELL-TO-CELL TRANSMISSION OF α-SYNUCLEIN AGGREGATES USING BIMOLECULAR FLUORESCENCE COMPLEMENTATION SYSTEM AND METHOD FOR SCREENING A SUBSTANCE FOR PREVENTING OR TREATING NEURODEGENERATIVE DISEASE USING THE SAME

(71) Applicant: KONKUK UNIVERSITY INDUSTRIAL COOPERATION CORP, Seoul (KR)

(72) Inventors: Seung-Jae Lee, Seoul (KR); He-Jin Lee, Seoul (KR); Eun-Jin Bae, Seoul (KR); Dong Kyu Kim, Seoul (KR)

(73) Assignee: KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 0 days.

(21) Appl. No.: 14/855,645

(22) Filed: Sep. 16, 2015

(65) Prior Publication Data

US 2016/0123961 A1    May 5, 2016

(30) Foreign Application Priority Data

Sep. 16, 2014   (KR) .................. 10-2014-0122973
Sep. 4, 2015    (KR) .................. 10-2015-0125245

(51) Int. Cl.
| | | |
|---|---|---|
| *C12N 15/00* | (2006.01) | |
| *G01N 33/52* | (2006.01) | |
| *A61K 31/7008* | (2006.01) | |
| *A01K 67/033* | (2006.01) | |
| *A61K 49/00* | (2006.01) | |
| *A61K 31/00* | (2006.01) | |
| *G01N 33/50* | (2006.01) | |

(52) U.S. Cl.
CPC ...... *A61K 31/7008* (2013.01); *A01K 67/0336* (2013.01); *A61K 31/00* (2013.01); *A61K 49/0008* (2013.01); *A61K 49/0045* (2013.01); *A01K 2217/052* (2013.01); *A01K 2217/15* (2013.01); *A01K 2217/206* (2013.01); *A01K 2227/703* (2013.01); *A01K 2267/0318* (2013.01); *A01K 2267/0393* (2013.01); *G01N 33/5058* (2013.01); *G01N 2500/10* (2013.01); *G01N 2800/28* (2013.01)

(58) Field of Classification Search
None
See application file for complete search history.

(56) References Cited

U.S. PATENT DOCUMENTS

2009/0029943 A1    1/2009    Kim

OTHER PUBLICATIONS

Danzer et al., Heat-shock protein 70 modulates toxic extracellular a-synuclein oligomers and rescues trans-synaptic toxicity. FASEB J. 25, 326-336 (2011).*
Heydari et al., Expression of Heat Shock Protein 70 is Altered by Age and Diet at the Level of Transcription. Molecular and Cellular Biology, May 1993, p. 2909-2918 vol. 13, No. 5.*
Li-Wei Lee et al., Vectors for co-expression of two genes in *Caenorhabditis elegans*, Gene, 455, 2010, pp. 16-21.
Craig C. Mello et al., Efficient gene transfer in *C. elegans*: extrachromosomal maintenance and integration of transforming sequences, The EMBO Journal, vol. 10, No. 12, pp. 3959-3970, 1991.
Federico Herrera et al., Visualization of cell-to-cell transmission of mutant huntingtin oligomers, PLoS Currents: Huntington Disease, Jan. 26, 2011, pp. 1-19.
Kurt A. Jellinger, α-Synuclein pathology in Parkinson's and Alzheimer's disease brain: incidence and topographic distribution—a pilot study, Acta Neuropathol (2003) 106:191-202.
Patrik Brundin et al., Prion-like transmission of protein aggregates in neurodegenerative diseases, Nature, vol. 11, pp. 301-307, Apr. 2010.
Seung-Jae Lee et al., Cell-to-cell transmission of non-prion protein aggregates, Nature, vol. 6, pp. 702-705, Dec. 2010.
Elodie Angot et al., Alpha-Synuclein Cell-to-Cell Transfer and Seeding in Grafted Dopaminergic Neurons In Vivo, PLOS One, vol. 7, Issue 6, pp. 1-11, Jun. 2012.
Karin M Danzer et al., Exosomal cell-to-cell transmission of alpha synuclein oligomers, Molecular Neurodegeneration, 2012, 7:42, pp. 1-12.
He-Jin Lee et al., Extracellular a☐synuclein—a novel and crucial factor in Lewy body diseases, Nature, vol. 10, pp. 92-97, Feb. 2014.
Tianhong Pan et al., The role of autophagy-lysosome pathway in neurodegeneration associated with Parkinson's disease, A Journal of Neurology, Brain, (2008), 131, 1969-1978.
Ellen Sidransky et al., Multi-center analysis of glucocerebrosidase mutations in Parkinson disease, N Engl J Med., Oct. 22, 2009; 361(17): 1651-1661.
Michael A. Nalls et al., A Multicenter Study of Glucocerebrosidase Mutations in Dementia With Lewy Bodies, JAMA Neurol. Jun. 2013 ; 70(6): . doi:10.1001/jamaneurol.2013.1925.
Paula Desplatsa et al., Inclusion formation and neuronal cell death through neuron-to-neuron transmission of a-synuclein, PNAS, vol. 106, No. 31, pp. 13010-13015, Aug. 4, 2009.
He-Jin Lee et al., Assembly-dependent endocytosis and clearanceof extracellular α-synuclein, The International Journal of Biochemistry & Cell Biology, 40 (2008) 1835-1849.

(Continued)

*Primary Examiner* — Scott Long
*Assistant Examiner* — Arthur S Leonard
(74) *Attorney, Agent, or Firm* — The PL Law Group, PLLC

(57) ABSTRACT

The present disclosure relates to dual-cell model and *Caenorhabditis elegans* model systems for measuring neuron-to-neuron transmission of protein aggregates, and more particularly to transgenic cell and animal model systems expressing fusion proteins of N-terminus or C-terminus of fluorescent proteins with α-synuclein proteins, methods for measuring continuous cell-to-cell transmission of α-synuclein aggregates using the same, and methods for screening substances for preventing or treating neurodegenerative diseases.

10 Claims, 64 Drawing Sheets

(56) References Cited

OTHER PUBLICATIONS

Susana A. Gonc̦alves et al., Zooming into protein oligomerization in neurodegeneration using BiFC, Trends in Biochemical Sciences, vol. 35, No. 11, pp. 643-651.
Tiago Fleming Outeiro et al., Formation of Toxic Oligomeric α-*Synuclein* Species in Living Cells, PLOS One, Apr. 2008, vol. 3, Issue 4, e1867.
Hideo Fujiwara et al, α-Synuclein is phosphorylated insynucleinopathy lesions, Nature Cell Biology, vol. 4, pp. 160-164, Feb. 2002.
Maria Grazia Spillantini et al., α-Synuclein in filamentous inclusions of Lewy bodies from Parkinson's disease and dementia with Lewy bodies, Proc. Natl. Acad. Sci. USA, vol. 95, pp. 6469-6473, May 1998.
Philipp J. Kahle, α-Synucleinopathy models and human neuropathology: similarities and diVerences, Acta Neuropathol (2008) 115:87-95.
Changyoun Kim et al., Neuron-released oligomeric a-synuclein is an endogenous agonist of TLR2 for paracrine activation of microglia, Nature Communications, DOI: 10.1038/ncomms2534, pp. 1-12.
Ara Jang et al., Non-classical of α-synuclein is sensitive to folding states and promoted under stress conditions, International Society for Neurochemistry, J. Neurochem, (2010) 113, pp. 1263-1274.
Matthew E. Gegg et al., Glucocerebrosidase Deficiency in Substantia Nigra of Parkinson Disease Brains, Annals of Neurology, vol. 72, No. 3, Sep. 2012, pp. 455-463.
Clark et al., Association of Glucocerebrosidase Mutations With Dementia With Lewy Bodies, Arch Neurol. May 2009 ; 66(5): 578-583.
R.N. Alcalay et al., Cognitive performance of GBA mutation carriers with early-onset PD, Neurology, 78 May 1, 2012, pp. 1434-1440.
Sophie E. Winder-Rhodes et al., Glucocerebrosidase mutations influence the natural history of Parkinson's disease in a community-based incident cohort, A Journal of Neurology, Brain, 2013: 136; pp. 392-399.
He-Jin Lee et al., Direct Transfer of α-Synuclein from Neuron to Astroglia Causes Inflammatory Responses in Synucleinopathies, Journal of Biological Chemistry, vol. 285, No. 12, pp. 9262-9272, Mar. 19, 2010.
Juan F. Reyes et al., Alpha-Synuclein Transfers from Neurons to Oligodendrocytes, GLLA, vol. 62, No. 3, pp. 387-398, Mar. 2014.
Idit Ron et al., ER retention and degradation as the molecular basis underlying Gaucher disease heterogeneity, Human Molecular Genetics, 2005, vol. 14, No. 16 2387-2398.
Thai Leong Yap et al., α-Synuclein Interacts with Glucocerebrosidase Providing a Molecular Link between Parkinson and Gaucher Diseases, Journal of Biological Chemistry, vol. 286, No. 32, pp. 28080-28088, Aug. 12, 2011.
S. Pablo Sardia et al., CNS expression of glucocerebrosidase corrects α-synuclein pathology and memory in a mouse model of Gaucher-related synucleinopathy, PNAS, vol. 108, No. 29, pp. 12101-12106, Jul. 19, 2011.
He-Jin Lee et al., Clearance of α-Synuclein Oligomeric Intermediates via the Lysosomal Degradation Pathway, J. Neurosci., Feb. 25, 2004, 24(8): pp. 1888-1896.
He-Jin Lee et al., Enzyme-linked immunosorbent assays for alpha-synuclein with species and multimeric state specificities, Journal of Neuroscience Methods, 199 (2011), pp. 249-257.
He-Jin Lee et al., Characterization of Cytoplasmic α-Synuclein Aggregates, The Journal of Biological Chemistry, vol. 277, No. 50, Issue of Dec. 13, pp. 48976-48983, 2002vol. 277, No. 50, Issue of Dec. 13, pp. 48976-48983, 2002.
Edward Rockenstein et al., Differential Neuropathological Alterations in Transgenic Mice Expressing α-synuclein From the Platelet-derived Growth Factor and Thy-1 Promoters, Journal of Neuroscience Research 68: pp. 568-578, (2002).
Sheila M. Fleming et al., Early and Progressive Sensorimotor Anomalies in Mice Overexpressing Wild-Type Human α-Synuclein, The Journal of Neuroscience, Oct. 20, 2004, 24(42): pp. 9434-9440.
Eun-Jin Bae et al., Antibody-Aided Clearance of Extracellular α-Synuclein Prevents Cell-to-Cell Aggregate Transmission, The Journal of Neuroscience, Sep. 26, 2012, 32(39): pp. 13454-13469.
Eliezer Masliah et al., Passive Immunization Reduces Behavioral and Neuropathological Deficits in an Alpha-Synuclein Transgenic Model of Lewy Body Disease, PLOS One, Apr. 2011, vol. 6, Issue 4, e19338.
Eun-Jin Bae et al., Glucocerebrosidase depletion enhances cell-to-cell transmission of a-synuclein, Nature Communications, 5:4755, DOI: 10.1038/ncomms5755, www.nature.com/naturecommunications, 2014, pp. 1-23.
S. Brenner, The Genetics of Caenorhabdztzs Elegans, Genetics, 77 : pp. 71-94, May 1974.
Martin S. Denzel et al., Hexosamine Pathway Metabolites Enhance Protein Quality Control and Prolong Life, Cell 156, pp. 1167-1178, Mar. 13, 2014.
Christian Hansen et al., α-Synuclein propagates from mouse brain to grafted dopaminergic neurons and seeds aggregation in cultured human cells, The Journal of Clinical Investigation, vol. 121, No. 2, pp. 715-725, Feb. 2011.
Cynthia Kenyon et al., A C. elegans mutant that lives twice as long as wile type, Letters, vol. 366, pp. 461-464, Dec. 2, 1993.
Louis R. Lapierre et al, The TFEB orthologue HLH-30 regulates autophagy and modulates longevity in Caenorhabditis elegans, Nature Communications, 4:2267, DOI: 10.1038/ncomms3267, www.nature.com/naturecommunications, 2013, pp. 1-17.
He-Jin Lee et al., Autophagic failure promotes the exocytosis and intercellular transfer of a-synuclein, Experimental & Molecular Medicine, (2013) 45, e22; doi:10.1038/emm.2013.45.
James P. McKay et al., eat-2 and eat-18 Are Required for Nicotinic Neurotransmission in the Caenorhabditis elegans Pharynx, Genetics, 166: pp. 161-169, Jan. 2004.
Candida Rogers et al., Inhibition of Caenorhabditis elegans social feeding by FMRFamide-related peptide activation of NPR-1, Nature Neuroscience, vol. 6, No. 11, pp. 1178-1185, 2003.
Marco Sardiello et al., A Gene Network Regulating Lysosomal Biogenesis and Function, Science, vol. 325, pp. 473-477, Jul. 24, 2009.
Popi Syntichaki et al., Specific aspartyl and calpain proteases are required for neurodegeneration in C. elegans, Nature, vol. 419, pp. 939-94431, Oct. 2002.
Hien T. Tran et al., α-Synuclein Immunotherapy Blocks Uptake and Templated Propagation of Misfolded α-Synuclein and Neurodegeneration, Cell Reports 7, pp. 2054-2065, Jun. 26, 2014.
David Vilchez et al., RPN-6 determines C. elegans longevity under proteotoxic stress conditions, Nature, vol. 498, pp. 263-269, Sep. 13, 2012.
Christian Frøkjr-Jensen et al., Single-copy insertion of transgenes in Caenorhabditis elegans, Nature Genatics, vol. 40, No. 11, pp. 1375-1383, Nov. 2008.
Keiko Gengyo-Ando et al., An efficient transgenic system by TA cloning vectors and RNAi for C. elegans, Biochemical and Biophysical Research Communications, 349, (2006), pp. 1345-1350.
PCR Fusion-Based Approach to Create Reporter Gene Constructs for Expression Analysis in Transgenic C. elegans, BioTechniques, vol. 32, No. 4, pp. 728-730, Apr. 2002 Partial Heat Denaturation Step during Reverse Transcription and PCR Screening Yields Full-Length 5'-cDNAs, BioTechniques, vol. 32, No. 4, pp. 730, Apr. 2002.
Ru-Huei Fu et al., Acetylcorynoline attenuates dopaminergic neuron degeneration and a-synuclein aggregation in animal models of Parkinson's disease, Neuropharmacology, vol. 82, pp. 108-120, Jul. 2014.

\* cited by examiner

Venus1-linker-αSyn

ATGGTGAGCAAGGGCGAGGAGCTGTTCACCGGGGTGGTGCCCATCCTGGTCGAGCTGGACGG
CGACGTAAACGGCCACAAGTTCAGCGTGTCCGGCGAGGGCGAGGGCGATGCCACCTACGGCA
AGCTGACCCTGAAGCTGATCTGCACCACCGGCAAGCTGCCCGTGCCCTGGCCCACCCTCGTG
ACCACCCTGGGCTACGGCCTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAGGACG
ACGGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTACAA
CTACAACAGCCACAACGTCTATATCACCGCCGACAAGCAAATCGATGGTGGCGGTGGCTCTG
GAGGTGGTGGGTCCCTTAAGGATGTATTCATGAAAGGACTTTCAAAGGCCAAGGAGGGAGTT
GTGGCTGCTGCTGAGAAAACCAAACAGGGTGTGGCAGAAGCAGCAGGAAAGACAAAAGAGGG
TGTTCTCTATGTAGGCTCCAAAACCAAGGAGGGAGTGGTGCATGGTGTGGCAACAGTGGCTG
AGAAGACCAAAGAGCAAGTGACAAATGTTGGAGGAGCAGTGGTGACGGGTGTGACAGCAGTA
GCCCAGAAGACAGTGGAGGGAGCAGGGAGCATTGCAGCAGCCACTGGCTTTGTCAAAAAGGA
CCAGTTGGGCAAGAATGAAGAAGGAGCCCCACAGGAAGGAATTCTGGAAGATATGCCTGTGG
ATCCTGACAATGAGGCTTATGAAATGCCTTCTGAGGAAGGGTATCAAGACTACGAACCTGAA
GCC (SEQ ID NO: 24)

αSyn-linker- Venus2

ATGGATGTATTCATGAAAGGACTTTCAAAGGCCAAGGAGGGAGTTGTGGCTGCTGCTGAGAA
AACCAAACAGGGTGTGGCAGAAGCAGCAGGAAAGACAAAAGAGGGTGTTCTCTATGTAGGCT
CCAAAACCAAGGAGGGAGTGGTGCATGGTGTGGCAACAGTGGCTGAGAAGACCAAAGAGCAA
GTGACAAATGTTGGAGGAGCAGTGGTGACGGGTGTGACAGCAGTAGCCCAGAAGACAGTGGA
GGGAGCAGGGAGCATTGCAGCAGCCACTGGCTTTGTCAAAAAGGACCAGTTGGGCAAGAATG
AAGAAGGAGCCCCACAGGAAGGAATTCTGGAAGATATGCCTGTGGATCCTGACAATGAGGCT
TATGAAATGCCTTCTGAGGAAGGGTATCAAGACTACGAACCTGAAGCCCTCGAGGAAGAACG
GCATCAAGGCCAACTTCAAGATCCGCCACAACATCGAGGACGGCGGCGTGCAGCTCGCCGAC
CACTACCAGCAGAACACCCCCATCGGCGACGGCCCCGTGCTGCTGCCCGACAACCACTACCT
GAGCTACCAGTCCAAGCTGAGCAAAGACCCCAACGAGAAGCGCGATCACATGGTCCTGCTGG
AGTTCGTGACCGCCGCCGGGATCACTCTCGGCATGGACGAGCTGTACAAGTAA (SEQ ID
NO: 25)

FIG.22

METHOD FOR MEASURING CELL-TO-CELL TRANSMISSION OF α-SYNUCLEIN AGGREGATES USING BIMOLECULAR FLUORESCENCE COMPLEMENTATION SYSTEM AND METHOD FOR SCREENING A SUBSTANCE FOR PREVENTING OR TREATING NEURODEGENERATIVE DISEASE USING THE SAME

CROSS-REFERENCE TO RELATED APPLICATIONS

This application claims priority to and the benefit of Korean Patent Application No. 10-2014-0122973 filed in the Korean Intellectual Property Office on Sep. 16, 2014 and Korean Patent Application No. 10-2015-0125245 filed in the Korean Intellectual Property Office on Sep. 4, 2015, the entire contents of which are incorporated herein by reference.

BACKGROUND

Technical Field

The present disclosure relates to dual-cell model and *Caenorhabditis elegans* model systems for measuring neuron-to-neuron transmission of protein aggregates, and more particularly to transgenic cell and animal model systems expressing fusion proteins of N-terminus or C-terminus of fluorescent proteins with α-synuclein proteins, methods for measuring continuous cell-to-cell transmission of α-synuclein aggregates using the same, and methods for screening substances for preventing or treating neurodegenerative diseases.

Related Art

Abnormal deposition of α-synuclein aggregates is a pathological feature of Parkinson's disease (PD) (Jellinger, K. A. 2003. *Acta Neuropathol* 106, 191-201). While a large body of recent studies suggests that transcellular transmission of α-synuclein aggregates drives the progression of PD (Danzer, K. M., et al. 2012 *Mol Neurodegener* 7, 42), the mechanisms underlying such transmission are not clearly understood. Particularly urgent issues include whether cell-to-cell transmission of aggregates is seeding-dependent, and whether the aggregates disseminate to large cell populations through continuous transmission and the role of other PD-related genes in this process (Lee, H. J. et al., 2014 *Nat Rev Neurol*).

Genetic and pathological evidence suggests that lysosomal impairment is a major contributor in the pathogenesis of Lewy body diseases (Pan, T. et al., 2008 *Brain*). The GBA1 gene encodes a lysosomal hydrolase, glucocerebrosidase (GCase), which is deleted in Gaucher disease, the most common lysosomal storage disease. Moreover, mutations in GBA1 are strong genetic risk factors in PD and in dementia with Lewy bodies, although the mechanism by which mutations in GBA1 increase the risk of PD remains unclear (Sidransky, E. et al. 2009 *N Engl J Med* 361, 1651-1661; Nalls, M. A. et al. 2013 *JAMA neurology* 70, 727-735). α-synuclein aggregates that are transferred from cell to cell are transported through the endolysosomal pathway and are degraded in lysosomes (Lee, H. J. et al. 2008 *Int J Biochem Cell Biol* 40, 1835-1849). The present inventors hypothesized that GBA1 deficiency causes lysosomal dysfunction, thereby increasing the efficiency of aggregate transmission.

The present inventors found, in the studies of the mechanism of perpetual transmission of α-synuclein aggregates through continuous cell-to-cell transmission, association of formation and transmission of α-synuclein aggregates with lysosomal function and aging in cells, that bimolecular fluorescence complementation (BiFC) system can facilitate measuring cell-to-cell transmission of α-synuclein aggregates, and developed the present invention.

BiFC is a technique of applying already known complementation of protein fragments to fluorescent proteins, fragmenting the fluorescent proteins into N-terminal fragments and C-terminal fragments and expressing these fragments, respectively, with two proteins between which interaction is to be studied, and analyzing fluorescence of whole fluorescent proteins occurring when the two fragments of the fluorescent proteins are linked to each other, while the two proteins are close to each other for interaction. Hu et al. reported that it is possible to analyze protein-protein interactions in higher animal cells using BiFC (Hu et al., Mol. Cell 2002, 9:789-798). Additionally, in recent years, many results of protein-protein interaction analysis results using BiFC are reported.

SUMMARY

The present disclosure provides a method for measuring continuous transmission of α-synuclein aggregates for analyzing cell-to-cell transfer and co-aggregation of α-synuclein aggregates, occurring between adjacent cells.

The present disclosure also provides a method for screening a substance for preventing or treating a neurodegenerative disease associated with α-synuclein aggregation, using the above measuring method.

To this end, there is provided a method for measuring cell-to-cell transmission of α-synuclein aggregate using a cell or animal model system including a first cell expressing a first fusion protein where an N-terminal fragment of a fluorescent protein and α-synuclein are fused; and a second cell expressing a second fusion protein where a C-terminal fragment of the fluorescent protein and α-synuclein are fused.

According to an aspect of the present disclosure, there is provided an animal model system for measuring transmission of protein aggregates, including a first cell expressing a first fusion protein where an N-terminal fragment of a fluorescent protein and a brain disease-associated protein are fused; and a second cell expressing a second fusion protein where a C-terminal fragment of the fluorescent protein and the brain disease-associated protein are fused. According to an example of the present disclosure, the animal model is a transgenic *Caenorhabditis elegans* model constructed to specifically express the first fusion protein in a pharynx muscle and specifically express the second fusion protein in a neuron linked to the pharynx. According to an embodiment of the present disclosure, the first fusion protein may be linked to myo-2 promoter and specifically expressed in the pharynx muscle of *C. elegans*, and the second fusion protein may be linked to flp-21 promoter and specifically expressed in the neuron linked to the pharynx. According to an embodiment of the present disclosure, the second fusion protein may further include a marker for flp-21 promoter activity. The marker indicates the second fusion protein specifically expressed in a pharyngeal neuron. Cell-to-cell transfer and co-aggregation of α-synuclein proteins derived from each adjacent cell can be confirmed by co-expressing the first fusion protein and the second fusion protein in the pharynx muscle (first cell) and the pharyngeal neuron (second cell), adjacent to each other, respectively, through culture of the *C. elegans* model, and then analyzing the strength, expression patterns, sites, and the like of a BiFC fluorescent signal produced from the linkage of the N-terminal fragment and the C-terminal fragment of the fluorescent protein.

According to an aspect of the present disclosure, there is provided a dual-cell model system for measuring cell-to-cell transmission of protein aggregates, including a first cell (donor cell) expressing a first fusion protein where an N-terminal fragment of a fluorescent protein and a brain disease-associated protein are fused; and a second cell (recipient cell) expressing a second fusion protein where a C-terminal fragment of the fluorescent protein and the brain disease-associated protein are fused. The dual-cell system measures, through co-culture of the first cell and the second cell, protein aggregates formed by co-aggregation of a brain disease-associated protein aggregate, acting as a seed, transferred from the first cell to the second cell by a primary release, and an endogenous brain disease-associated protein, or measures a secondary release thereof from the second cell. According to an example of the present disclosure, the dual-cell model system may include a neuroblastoma cell line (KCLRF-BP-00322) transformed with a polynucleotide having a nucleotide sequence represented by SEQ ID NO: 4 encoding a fusion protein (Venus1-αSyn, V1S) of an N-terminal fragment of Venus and α-synuclein; and a neuroblastoma cell line (KCLRF-BP-00323) transformed with a polynucleotide having a nucleotide sequence represented by SEQ ID NO: 5 encoding a fusion protein (αSyn-Venus2, SV2) of a C-terminal fragment of Venus and α-synuclein. The cell lines, which are cells used in the dual-cell model system of the present disclosure, are cell lines stably expressing fusion proteins of fragments of Venus and α-synuclein. These cell lines were first produced by the present inventors, deposited in the Korean Cell Line Bank (KCLB) on Aug. 26, 2014, and given Accession Nos. KCLRF-BP-00322 and KCLRF-BP-00323, respectively.

As used herein, the term "secondary release" of protein aggregates, which differs from simple cell-to-cell transmission of protein molecules themselves or protein aggregates, include all types of secondary transmission of protein aggregates formed by co-aggregation of the protein molecules or aggregates, acting as a seed, primarily transferred from a donor cell, and endogenous proteins of a recipient cell. The term "secondary release" (or secondary transmission) is used herein to explain continuous neuron-to-neuron transmission of protein aggregates, which is a contrast to temporary and discontinuous neuron-to-neuron transmission of protein molecules. Thus, the secondary release does not mean a simple second release, but covers all types of transmission of protein aggregates formed by a seeding mechanism.

In the present disclosure, the florescent protein is a florescent protein that can be used in a BiFC analysis for analyzing protein-protein interactions and dimerization or oligomerization in cells. The fluorescent protein is not specifically limited to a specific type, as long as it can be introduced into a cell and measure florescence. Preferably, the fluorescent protein may be selected from the group consisting of Venus, a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed, or mCherry.

According to an example of the present disclosure, the N-terminal fragment of the fluorescent protein is amino acids of 1-158 of Venus represented by SEQ ID NO:1, and the C-terminal fragment of the fluorescent protein is amino acids of 159-239 of Venus represented by SEQ ID NO:2. The fragments of the fluorescent protein may be designed in various sizes based on the types, characteristics, stability, and fluorescence intensity of the protein.

As used herein, the term "brain disease-associated protein" refers to proteins specifically detected in brain diseases, such as Parkinson's disease, Alzheimer's disease, or dementia with Lewy bodies. α-synuclein, tau proteins, β-amyloid, polyglutamine proteins, superoxide dismutase 1 (SOD1), prion proteins, FUS proteins, TDP-43 proteins, and the like may be used as a brain disease-associated protein of the present disclosure.

The function and sequence information of the brain disease-associated proteins that may be used in the present disclosure are already known and can be readily retrieved from database, such as NCBI. Origin of these proteins is not specifically limited, and preferably, these proteins may be derived from mammals. For example, α-synuclein may include the amino acid sequence represented by SEQ ID NO: 3 (GenBank Accession No. AAI08276) derived from humans.

According to an embodiment of the present disclosure, cell-to-cell transmission of the protein aggregates is measured through detection of a BiFC signal occurring when the N-terminal fragment of the fluorescent protein, which is expressed in the first cell and then transferred to the second cell, is linked to the C-terminal fragment of the fluorescent protein, or when the C-terminal fragment of the fluorescent protein, which is expressed in the second cell and then transferred to the first cell, is linked to the N-terminal fragment of the fluorescent protein. As used herein, the terms "N-terminal fragment" and "C-terminal fragment" refer to bimolecular fragments of a fluorescent protein fragmented in N-terminal and C-terminal directions, respectively.

The BiFC analysis is a technique of applying protein fragment complementation to a fluorescent protein, including fragmenting the fluorescent protein into a N-terminal fragment and a C-terminal fragment, so as to be expressed, respectively, with two proteins between which interaction is to be studied, and analyzing fluorescence of a whole fluorescent protein occurring when the two fragments of the fluorescent protein are linked to each other, while the two proteins are close to each other for interaction. The present inventors first introduced the BiFC technique into a cell model for confirming neuron-to-neuron transmission of protein aggregates.

According to an example of the present disclosure, two stable cell lines were produced expressing α-synuclein fused with the N-terminus (V1S) fragment or the C-terminus (SV2) fragment of Venus, a variant of yellow fluorescent protein (see FIG. 1a). Neither V1S-expressing cells nor SV2-expressing cells fluoresced in individual culture (see FIGS. 1d and 1e). When the cell lines were co-cultured, however, fluorescence resulting from dimerization or oligomerization of V1S and SV2 fusion proteins during cell-to-cell transfer of α-synuclein was visualized using BiFC (see FIGS. 1a, 1d, and 1e).

According to an aspect of the present disclosure, there is provided a method for measuring continuous transmission of brain disease-associated protein aggregates over the generation of cells, including a) preparing a first neuron (donor cell) having a first polynucleotide encoding a first fusion protein where an N-terminal fragment of a fluorescent protein and a brain disease-associated protein are fused; b) preparing a second neuron (recipient cell) having a second polynucleotide encoding a second fusion protein where a C-terminal fragment of the fluorescent protein and the brain disease-associated protein are fused; c) mixing the first neuron and the second neuron in a culture medium and subculturing the mixture; and d) measuring the percentage of BiFC-positive cells in the subculture.

Measuring the continuous transmission of the protein aggregates is significantly important for understanding the progression of a brain disease by pathological aggregate spreading in the central nervous system (CNS). Thus, the dual-cell BiFC system of the present disclosure may be useful for measuring continuous neuron-to-neuron transmission of co-aggregated protein aggregates produced in a first round of transmission, not a single, discontinuous transmission process.

According to an example of the present disclosure, the first polynucleotide has a nucleotide sequence represented by SEQ ID NO: 4 and encodes the fusion protein of the N-terminal fragment of Venus and the brain disease-associated protein. The second polynucleotide has a nucleotide sequence represented by SEQ ID NO: 5 and encodes the fusion protein of the C-terminal fragment of Venus and the brain disease-associated protein.

Also, the present disclosure provides a method for screening a substance for preventing or treating a neurodegenerative disease associated with α-synuclein aggregation, using the method for measuring cell-to-cell transmission of α-synuclein aggregates using the cell or animal model system including the first cell expressing the first fusion protein where the N-terminal fragment of the fluorescent protein and α-synuclein are fused; and the second cell expressing the second fusion protein where the C-terminal fragment of the fluorescent protein and α-synuclein are fused.

According to an aspect of the present disclosure, the substance for preventing or treating the neurodegenerative disease associated with α-synuclein aggregation may be a gene. In this case, the screening method includes increasing or decreasing an expression level of a candidate gene which is expressed in the first cell and the second cell of the cell or animal model system; and measuring a change in the BiFC fluorescent signal according to the change in the expression level of the candidate gene, to analyze association between the candidate gene and cell-to-cell transmission of α-synuclein aggregates.

According to an embodiment of the present disclosure, the screening method provides a method for detecting a gene controlling continuous transmission of brain disease-associated protein aggregates, including 1) preparing a first neuron (donor cell) having a first polynucleotide encoding a first fusion protein where an N-terminal fragment of a fluorescent protein and a brain disease-associated protein are fused; 2) preparing a second neuron (recipient cell) having a second polynucleotide encoding a second fusion protein where a C-terminal fragment of the fluorescent protein and the brain disease-associated protein are fused, and the second neuron inhibiting the expression of a candidate gene; 3) mixing the first neuron and the second neuron in a culture medium and subculturing the mixture; 4) measuring the percentage of BiFC-positive cells in the subculture; and 5) when the percentage of the BiFC-positive cells increases during subculture, determining that the candidate gene deficiency increases the transmission of the protein aggregates.

The gene detection method may be used in the studies of genes controlling neuron-to-neuron spreading of protein aggregates. According to an example of the present disclosure, in an experimental method of using the cell model system of the present disclosure, it was found that the deletion of a specific gene (GBA1) causes lysosomal dysfunction, thereby allowing continuous transmission of protein aggregates (see FIGS. 4a to 4e, FIGS. 6a to 6g, and FIGS. 7a to 7g). Further, as experimental results of a transgenic animal model according to an embodiment of the present disclosure, when the fusion proteins (V1S+SV2) of the present disclosure were introduced into dynamin mutants, dyn-1(ky51), BiFC fluorescence was significantly reduced compared to that in wild-type (FIGS. 27a and 27b), and when the fusion proteins (V1S+SV2) were introduced into asp-4(ok2693) and asp-1(tm666) mutants, mutations in cathepsin genes, BiFC fluorescence was significantly increased in both mutants, often in the form of inclusion bodies (FIGS. 27c, 27d, and 27e; and "D" and "E" of FIG. 31). These results suggest that lysosomal responses are crucial for protecting the animals from age-dependent aggregate propagation. According to an embodiment of the present disclosure, the candidate gene may be a gene associated with aging. To examine the effects of changes in aging rates on aggregate transmission and the degenerative phenotypes, the present inventors introduced the BiFC α-synuclein constructs into daf-2(e1370) mutant showing slower aging rate and extended life span and daf-16(mu86) mutants aging faster than wild-type and having a shortened life span ("A" and "B" of FIG. 29). As a result, the daf-2(e1370); V1S+SV2 animals showed reduced BiFC signal (FIGS. 24a and 24b; "D" of FIG. 29), smaller number of inclusion bodies (FIGS. 24c and 24d; "E" of FIG. 29), less nerve degeneration (FIGS. 24e and 24f; "F" and "G" of FIG. 29), improved pumping behavior (FIG. 24g; "H" of FIG. 29), and extended life span than the V1S+SV2 line (FIG. 24h; "I" of FIG. 29). On the other hand, in the daf-16(mu86); V1S+SV2 animals, BiFC-positive inclusion bodies appeared much earlier than in the V1S+SV2 animals; as early as 2-days post the L4-stage (FIGS. 24c and 24d; "E" of FIG. 29). These results indicate that aging is the major factor regulating the rate of cell-to-cell transmission of α-synuclein aggregates and the associated degenerative phenotypes in vivo. Also, to detect a gene associated with lysosome affecting transmission of protein aggregate, the present inventors prepared the daf-16 (mu86); V1S+SV2 transgenic lines overexpressing hlh-30, an ortholog of TFEB, the master control transcription factor for lysosome biogenesis (Example 2-6). As experimental results of using the transgenic animals, it was demonstrated that the hlh-30 transgenic lines represent reduced BiFC signal (hence, reduced aggregate transmission), decreased nerve degeneration, increased pumping rates, and increased life-span (FIGS. 27k, 27l, 27m, 27n, 27o, 27p, 27q, and 27r; "L" to "O" of FIG. 32). Accordingly, the gene detection method of the present disclosure can effectively detect a gene that may be a therapeutic target of a neurodegenerative disease or a brain disease, and restoring the activity of the thus-detected gene or the expression protein can facilitate a therapeutic approach to a brain disease caused by accumulation of protein aggregates.

According to an aspect of the present disclosure, there is provided a method for screening a substance for preventing or treating a neurodegenerative disease associated with α-synuclein aggregation, using the method of the present disclosure for measuring cell-to-cell transmission of α-synuclein aggregates using the cell or animal model system of the present disclosure. The screening method includes treating a test substance in the cell or animal model; measuring a change in a BiFC fluorescent signal according to the treatment of the test substance; and when the BiFC fluorescent signal is reduced, determining the test substance as a substance for preventing or treating the neurodegenerative disease.

According to an embodiment of the present disclosure, the measuring of the change in the BiFC fluorescent signal according to the treatment of the test substance may include measuring a change in the BiFC fluorescent signal according to aging of the cell or animal model. According to an embodiment of the present disclosure, the cell or animal model may be completely or partially absent from lysosomal function. According to an embodiment of the present disclosure, the test substance may have an anti-aging activity. In an experiment using a transgenic animal model according to an embodiment of the present disclosure, when N-acetylglucosamine (GlcNAc), known as having an anti-aging activity, was administered to the V1S+SV2 and daf-16 (mu86); V1S+SV2 animals, both animals showed reduced formation of BiFC-positive inclusion bodies (FIGS. 25a and 25b), significantly alleviated phenotypes for nerve degeneration (FIGS. 25c, 25d, 25e, and 25f), increased pumping behavior (FIG. 25g), and extended life span (FIG. 25h). These results suggest that anti-aging treatments can slow the progress of synucleinopathy. Thus, the screening method of the present disclosure can be used for effectively detecting a substance (compound) that can be used as a therapeutic agent for a neurodegenerative disease or a brain disease associated with accumulation of protein aggregates.

According to an embodiment of the present disclosure, the neurodegenerative disease associated with α-synuclein aggregation may be Parkinson's disease.

Also, the present disclosure provides an agent for preventing or treating a neurodegenerative disease, including N-acetylglucosamine as an effective ingredient detected by the screening method. According to an embodiment of the present disclosure, N-acetylglucosamine showed the effects of inhibiting transmission of α-synuclein aggregates in the BiFC experimental animal model (see Experimental result 2-3). Thus, N-acetylglucosamine may be used as a pharmaceutical composition for preventing or treating a neurodegenerative disease associated with transmission of α-synuclein aggregates, particularly Parkinson's disease.

An N-acetylglucosamine compound according to the present disclosure may be used in the form of a salt, and preferably a pharmaceutically acceptable salt. Examples of the salt may include a pharmaceutically acceptable acid addition salt prepared from free acid, and for the free acid, an organic acid and an inorganic acid may be used. Also, the pharmaceutical composition may include N-acetylglucosamine alone in a pharmaceutically effective amount or include at least one pharmaceutically acceptable carrier, excipient, or diluent. As used herein, the term "pharmaceutically effective amount" refers to an amount sufficient to prevent, improve or treat symptoms of a neurodegenerative disease, and may properly vary depending on degree of the symptoms; age, weight, health condition, and gender of a patient, administration path, treatment duration, and the like. Also, as used herein, the term "pharmaceutically acceptable" means what is physiologically acceptable and, when administered to human, generally does not cause allergic reactions, such as gastrointestinal disorder and dizziness, or similar reactions thereto. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate, mineral oil, and the like. Also, they may further include a filler, an anti-aggregating agent, a lubricant, a humactant, a fragrance agent, an emulsifier, a preservative, and the like.

Also, the pharmaceutical composition may be formulated using a process known in the art, so as to provide immediate, sustained, or delayed release of an active ingredient after administered to mammals. Examples of the formulation may include, but is not limited to, a powder, a granule, a tablet, emulsion, syrup, an aerosol, a soft or hard gelatin capsule, a sterile injection solution, a sterile injection powder, and the like. The pharmaceutical composition according to the present disclosure may be administered in various paths, such as orally, percutaneously, subcutaneously, intravenously, and intramuscularly, and the administration amount of the active ingredient may be properly determined depending on various factors, such as administration path; age, gender, weight of a patient; severity of a patient; and the like. Also, the pharmaceutical composition may be administered in combination with known compounds having the effects of preventing, improving, or treating a neurodegenerative disease.

Hereinafter, the seeding mechanism of α-synuclein aggregate as a brain disease-associated protein according to the present disclosure, the transmission mechanism of the aggregate, the pathological association, and the method for measuring continuous transmission of the aggregate will be described in detail.

The present inventors found that cell-to-cell transmission of α-synuclein aggregates is mediated by a seeding mechanism and that secondary secretion of the resulting seeded aggregates mediates contiguous spreading of α-synuclein aggregates. In addition, the contiguous spreading of aggregates is significantly promoted by lysosomal dysfunction secondary to loss of GBA1 function. In PD patients with heterozygous mutations of GBA1, GCase activities and protein levels were reduced (Gegg, M. E, et al. 2012 *Ann Neurol* 72, 455-463), and this indicates pathological consequences of GBA1 heteroinsufficiency. Moreover, GBA1 mutation carriers have twice the number of cortical Lewy bodies than those of non-carriers (Clark, L. N. et al. *Arch Neurol* 66, 578-583). In addition, heterozygous mutations of GBA1 are associated with increased risk of cognitive impairment (Alcalay, R. N. et al. 2012 *Neurology* 78, 1434-1440) and more rapid disease progression (Winder-Rhodes, S. E. et al. 2013 *Brain* 136, 392-399), which support the hypothesis that the rate of spreading of Lewy pathology determines the rate of clinical progression.

The present disclosure provides evidence that α-synuclein transmission is not a single, discontinuous event, but a perpetual one. First, continuous subculture of V1S/SV2 co-culture showed increased BiFC-positive cell population, instead of its decrease. This observation that there is no dilution effect of BiFC-positive cells as the cell population grows suggests perpetual spreading of α-synuclein aggregates. Second, the present inventors found the release of BiFC-positive species from V1S/SV2 co-culture, and this can only be explained by the secondary release of these species after co-aggregation of transferred and resident α-synuclein in recipient cells. This secondary release of aggregates is a pre-requisite for perpetual spreading of aggregates. Third, ectopic introduction of V1S protein, released from V1S cells, rapidly resulted in BiFC-positive punctates in SV2 cells, and BiFC-positive aggregate species were gradually released from SV2 cells, as intracellular BiFC species gradually decreased. These results collectively support the idea that α-synuclein aggregates perpetually spread through the continuous cycle of exocytosis, endocytosis, seeded aggregation, and secondary exocytosis.

After several passage of the co-culture, the BiFC-positive population reached a steady state, the balance between aggregate production/spreading and degradation as well as cell proliferation rate, which will determine the rate of aggregate dilution. The dilution effect due to cell proliferation will not be a factor in vivo, since neurons are post-mitotic. The present disclosure suggests that lysosomal degradation is a main force behind the limited increase in BiFC-positive population during successive passages. Increased steady state levels of BiFC-positive cell population with GBA1−/− cells support this idea.

Cell-to-cell transmission the present inventors analyzed with the new dual-cell BiFC system is a relatively infrequent event. Typically, 2 to 5% cells with BiFC-positive puncta are observed, though the number varies depending on the culture conditions, such as cell density. The BiFC fluorescence observed in this system is not an artefact, because one cell line alone rarely shows a BiFC signal. Neuroblastoma cells used in the present disclosure produce catecholamines, such as dopamine, which are vulnerable to oxidation. Occasional occurrence of BiFC-positive cells in each cell line is probably due to autofluorescence generated by oxidation of catechols. Although the present inventors used extreme caution in handling these cell lines (only 2-week to 2-month old cells were used), some cells generated this non-specific background, usually in less than 0.5% of cells.

In the dual cell BiFC system of the present disclosure, since V1S cells secrete α-synuclein much more than SV2 cells (see FIGS. 1a to 1g), the present inventors considered that V1S cells are predominant donor cells at least in the initial transfer. In the present disclosure, the role of GCase 1 in the recipient cells was investigated, because the primary goal was to assess the role of lysosomal function in clearance of transferred α-synuclein and its consequence to aggregates spreading. For this reason, SV2GBA1−/− was used in the present disclosure.

Although the present disclosure suggests that loss of GBA1 function plays a role in synucleinopathies, this does not necessarily rule out the pathological consequences of gain of GBA1 function mutations. For example, previous studies associated mutant GBA1 with impaired endoplasmic reticulum-associated degradation (Ron, I. et al. 2005 *Hum Mol Genet* 14, 2387-2398) and physical interaction between α-synuclein and GCase was demonstrated under acidic conditions (Yap, T. L. et al. 2011 *J Biol Chem* 286, 28080-28088). These studies support a potential role for gain-of-function GBA1 mutations, and stress the point that GBA1 mutations may exert their pathogenic actions via multiple mechanisms. That said, the present disclosure demonstrates that ectopic expression of wild type GBA1, not an activity-deficient GBA1 mutant, reversed the effects of GBA1 deletion on spreading of α-synuclein aggregates, presenting an attractive therapeutic opportunity for idiopathic PD. These results are in good agreement with previous studies demonstrating amelioration of synucleinopathy lesions in the brains of the GD mouse model (D409V/D409V) by viral-mediated expression of GBA1 (Sardi, S. P. et al. 2011 *Proc Natl Acad Sci USA* 108, 12101-12106). Taken together, the present disclosure implicates GCase as a disease-modifying therapeutic target, and suggests that restoring the activity of this protein may retard the spread of Lewy pathology, thereby halting the progression of PD.

Meanwhile, the association between aging and neurodegenerative diseases was reported. However, the role of aging in development and progression of neurodegenerative diseases was not specifically revealed. Here, the present inventors use the *C. elegans* model of the present disclosure to demonstrate that aging accelerates cell-to-cell transmission of α-synuclein aggregates, characteristics of Parkinson's disease, and the progression of disease symptoms, such as nerve degeneration, behavioral deficits, and reduced lifespan. It was found, however, that genetic and pharmacological anti-aging treatment slowed the spreading of the aggregates and associated symptoms. Lysosomal degradation was significantly impaired in aging animal models, while anti-aging treatments reduced the impairment. hlh-30p::hlh-30, the master controller of lysosomal biogenesis, reduced cell-to-cell transmission of protein aggregates in the aging animal models. These results demonstrate that aging controls the transmission of protein aggregates and that anti-aging treatment can slow the spreading of aggregates and the progression of associated diseases by restoring lysosomal function.

The regulation on transmission of α-synuclein aggregates and their associated symptoms by GBA1 gene can be confirmed from experiments using a dual-cell model of the present disclosure including cells expressing fusion proteins of N-terminus or C-terminus of the fluorescent protein with α-synuclein. Further, continuous transmission of protein aggregates between adjacent cells can be effectively measured through experiments using a BiFC animal model system of the present disclosure, and also the regulation thereon by genes, such as daf-2, daf-16, dyn-1, asp-1, asp-4, or hlh-30, and GlcNAc compounds, can be confirmed. Thus, the present disclosure may be used for screening a substance for preventing or treating a neurodegenerative disease associated with protein aggregation.

BRIEF DESCRIPTION OF THE DRAWINGS

FIG. 1a is a schematic diagram of a dual-cell BiFC system. FIG. 1b illustrates western blot analysis of V1S and SV2 stable cell lines. Primary antibodies used were Ab274 (against human α-synuclein; left panel), anti-GFP C-terminus (middle panel), and anti-GFP N-terminus (right panel). FIG. 1c illustrates western analysis of α-synuclein secreted in culture media. SgII: secretogranin II, a loading control for secreted proteins. FIGS. 1d and 1e show that individual cultures and co-cultures of V1S and SV2 cell lines were immunostained for α-synuclein and one of N-terminal (FIG. 1d) or C-terminal (FIG. 1e) fragment of Venus. BiFC signal (green) emerged from these immunostains. The broken lines in inserts represent cell boundaries. Scale bars: 20 μm. FIG. 1f shows that BiFC signal (green) emerged with phospho-α-synuclein (top panels) and ubiquitin (bottom panels). The boxed regions are magnified in the inserts. The broken lines in the inserts represent cell boundaries. Blue: nuclei. Scale bars: 20 μm. FIG. 1g illustrates a three-dimensional reconstruction of cells containing BiFC fluorescence. Scale bars: 5 μm.

FIG. 2a illustrates size exclusion chromatography of V1S CM and V1S CM-FT (flow-through fraction of 100 kDa cutoff filtration). Blue: V1S CM, Red: V1S CM-FT. FIG. 2b is a western blotting image of the indicated fractions in FIG. 2a. FIG. 2c illustrates quantification of the western blotting image in FIG. 2b. FIG. 2d illustrates a BiFC fluorescence image in SV2 cells treated with V1S CM or V1S CM-FT. Scale bars: 20 μm. FIG. 2e illustrates the percentage of BiFC-positive cells in FIG. 2d. 500 cells were analyzed in each of three independent experiments. **: $p < 0.01$.

FIG. 3a illustrates subcultures of a dual-cell BiFC system. BiFC-positive inclusions are indicated with arrowheads. Bottom panels are magnified image of the boxed regions. Scale bars: 20 μm. FIG. 3b illustrates quantification of BiFC-positive cells in FIG. 3a. n=4, 1000 cells per each experiment, *: $p<0.05$, : $p<0.01$. FIG. 3c illustrates BiFC fluorescence in media in the indicated subcultures. : $p<0.01$. FIG. 3d illustrates ELISA specific for α-synuclein multimer in the media of each subculture. **: $p<0.01$. FIGS. 3e and 3g illustrate effects of media wash (FIG. 3e) and Ab274 (FIG. 3g) on percentage of BiFC-positive cells in the indicated subcultures. n=3, 1000 cells per each experiment, *: $p<0.05$, **: $p<0.01$. FIGS. 3f and 3h illustrate BiFC fluorescence in the media of cultures identified in FIGS. 3e and 3g, respectively. FIGS. 3i, 3j, and 3k show that conditioned medium of V1S culture was added to SV2 cells for 10 min, and then V1S medium was removed. FIG. 3i shows that time-dependence of decay in intracellular BiFC fluorescence was analyzed in SV2 cells. FIG. 3j illustrates time courses of secondary release of BiFC-positive aggregates. FIG. 3k shows that multimeric α-synuclein was analyzed in culture media.

FIG. 4a shows frame-shift mutations in two alleles of GBA1 gene in SV2 cells. FIG. 4b is western blot showing reduced GCase1 expression in SV2GBA1−/− cells. FIG. 4c shows reduction of a total GCase activity. n=3, ** $p<0.0001$. FIG. 4d shows specific reduction of GCase1 activity. n=3,  $p<0.0001$. FIG. 4e shows an increased ratio of glucocerebroside (GL1) to galactocerebroside (GalCer) in SV2GBA1−/− cells. n=3, ** $p<0.0001$.

FIG. 5a illustrates levels of p62 in Triton-soluble fractions; n=3, * $p<0.05$. FIG. 5b illustrates levels of polyubiquitinated proteins. Quantified regions in the blots are indicated with lines on the right; n=4, * $p<0.05$. FIG. 5c illustrates accumulation of acidic compartments. 500 cells were analyzed in each of four independent experiments. Scale bars: 20 □μm. n=4, * $p<0.05$. FIG. 5d illustrates internalized dextran-fluorescein isothiocyanate; Scale bars: 20 μm. n=4, 100 cells per each experiment, * $p<0.05$. FIG. 5e illustrates accumulation of endosomal structures. One hundred cells were analyzed. Scale bars: 5 μm (left panels), 2 μm (right panels), ** $p<0.01$.

FIG. 6a illustrates cell-to-cell α-synuclein transmission in a dual-cell BiFC system. BiFC-positive aggregates are indicated with arrowheads; n=4, 500 cells per each experiment, * $p<0.05$. FIG. 6b illustrates accumulation of ectopically introduced α-synuclein aggregates (sonicated fibrils). Fluorescence was measured in 500 cells in each of four independent experiments. * $p<0.05$. FIG. 6c illustrates subcultures of a dual-cell BiFC system. FIG. 6d illustrates quantification of BiFC-positive cells shown in FIG. 6c. n=3, 500 cells per each experiment, * $p<0.05$, * $p<0.005$, ** $p<0.0001$. FIG. 6e illustrates multimeric α-synuclein ELISA analysis of culture media from the indicated subcultures. n=3, * $p<0.05$, *** $p<0.005$. FIGS. 6f and 6g illustrate reversal of GBA1 knockout phenotype by expression of wild type GBA1, not activity-deficient E235K GBA1 mutations; n=4, 1000 cells per each experiment, * $p<0.05$, #$p<0.05$.

FIG. 7a illustrates immunohistochemistry of α-synuclein with three different antibodies. The boxed regions in top panels are magnified in lower panels. Engrafted cells are indicated with arrowheads. Scale bars: top panel, 250 μm; lower panels, 20 μm. FIGS. 7b and 7c illustrate α-synucleinimmuno reactivity quantified and expressed as the percentage of the grafted region; n=8, * $p<0.01$ by t-test. FIGS. 7d and 7e illustrate co-immunofluorescence analysis of engrafted cells (arrowheads). Pixel intensities of α-synuclein level measured in 40 cells per animal (n=8). Scale bar: 5 μm. FIGS. 7f and 7g illustrate co-immunofluorescence analysis of engrafted cells stained for TH (arrowheads). Pixel intensities of α-synuclein labels measured in 40 cells per animal (n=6). Scale bar: 5 μm.

To exclude the possibility of non-specific fluorescence due to interaction between Venus fragments, cells transfected with an N-terminal fragment of Venus without α-synuclein were co-cultured with SV2 cells (V1+SV2). Likewise, V1S cells were co-cultured with cells transfected with a C-terminal fragment of Venus without α-synuclein (V1S+V2). There was no BiFC fluorescence in the V1+SV2 co-culture and V1S+V2 co-culture. Scale bars: 20 μm.

Figure 1A:
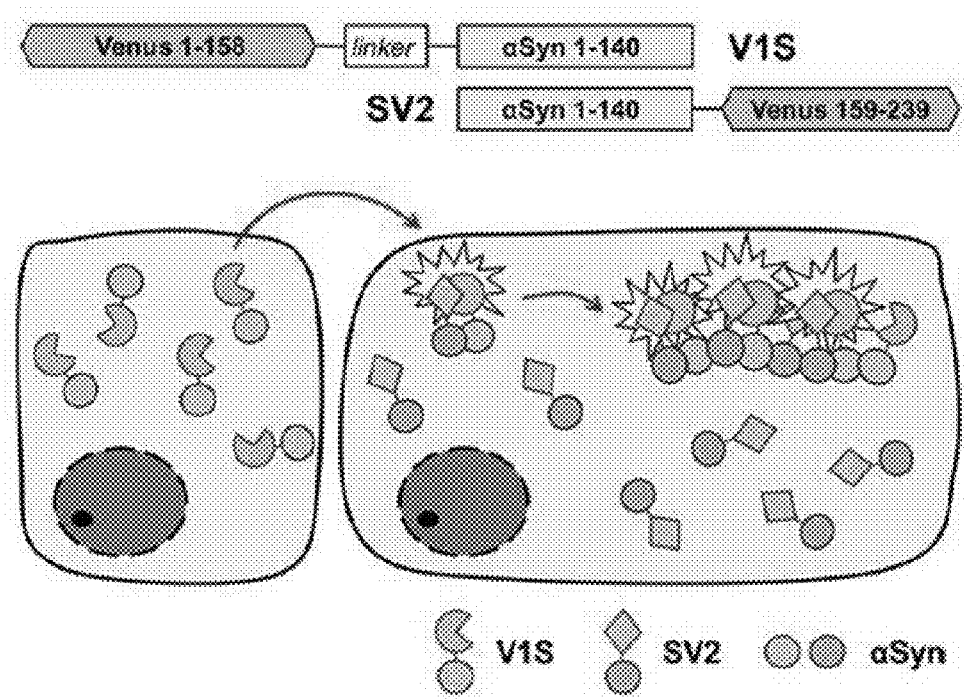
FIGS. 1a to 1g illustrates a process for producing a dual-cell BiFC system according to the present disclosure.
Figure 1B:
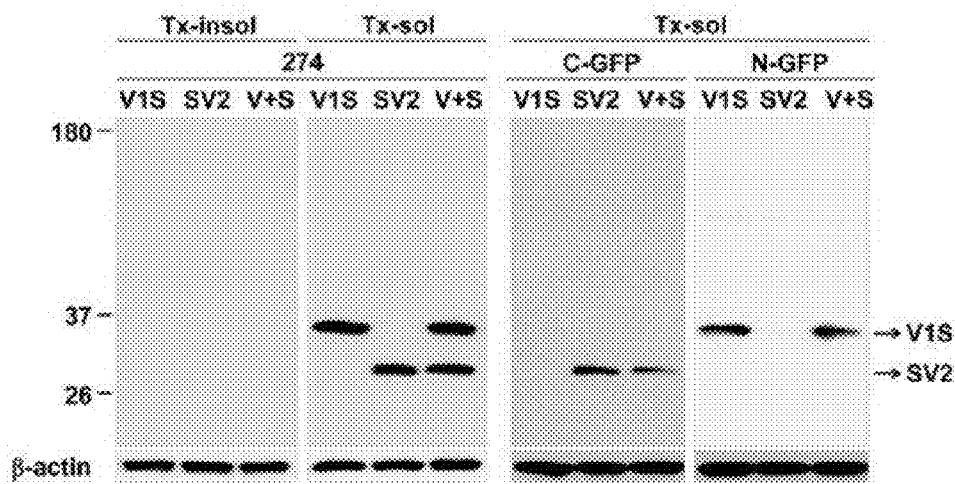
Figure 1C:
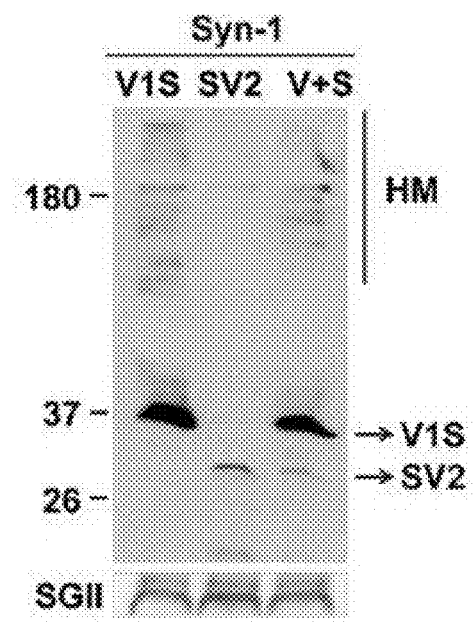
Figure 1D:
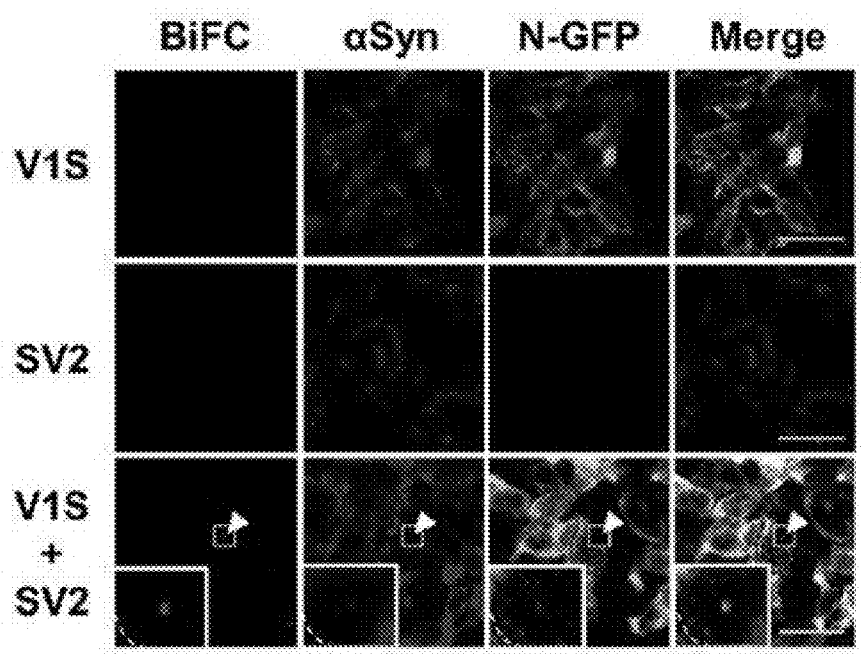
Figure 9:
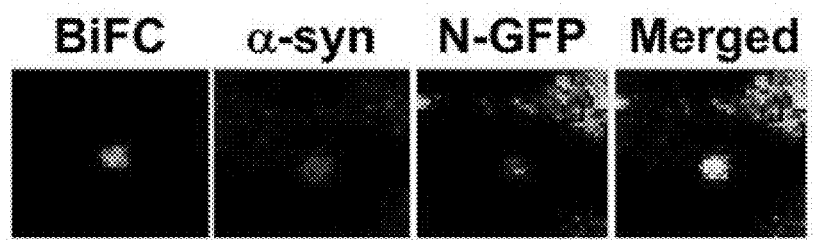

FIG. 9 is a magnified image of the boxed region in FIG. 1d.

Figure 1E:
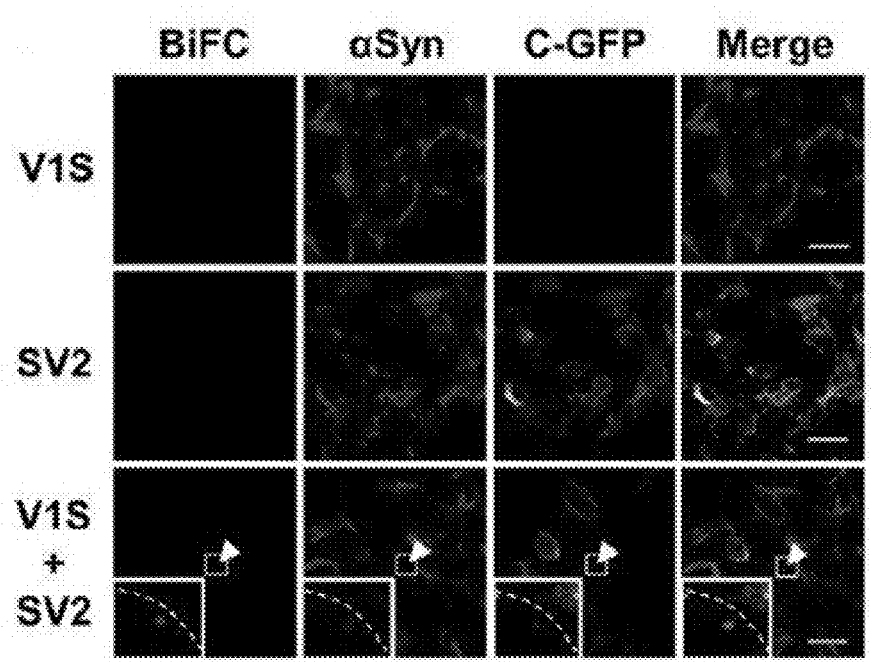
Figure 10:
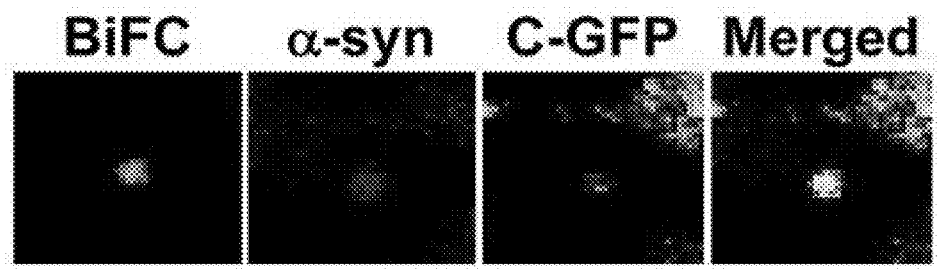

FIG. 10 is a magnified image of the boxed region in FIG. 1e.

Figure 1F:
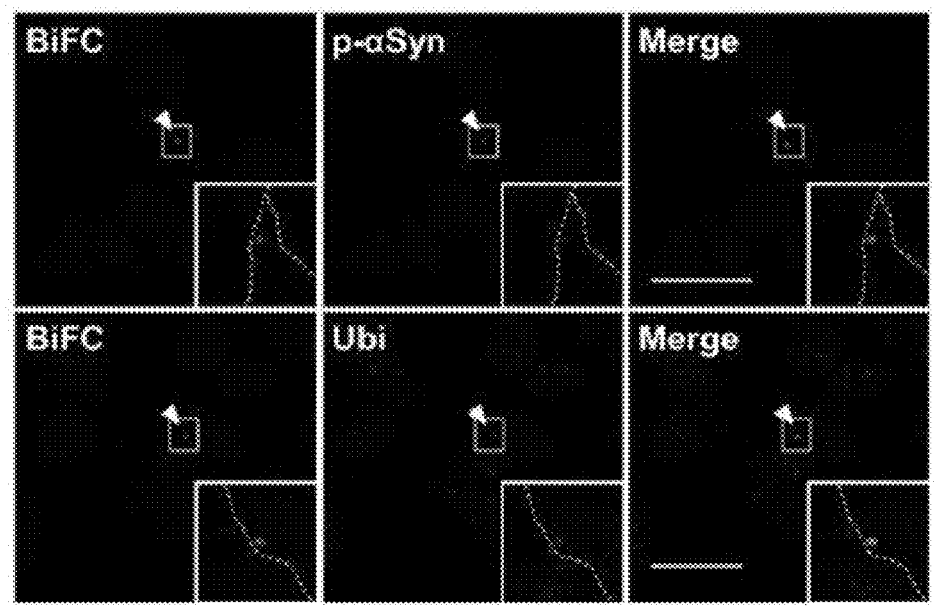
Figure 11:
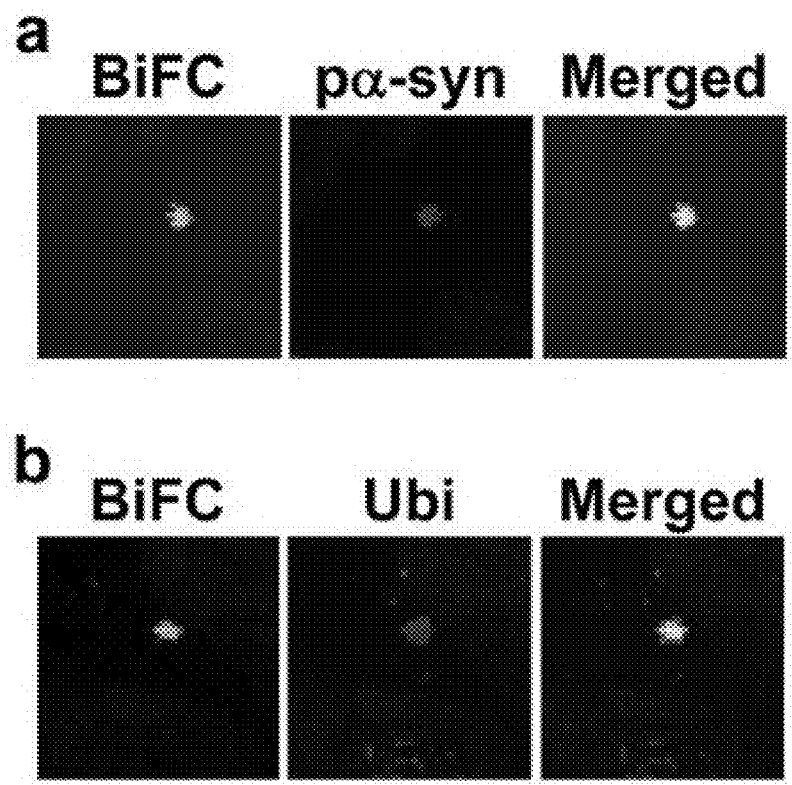

FIG. 11 is a magnified image of the boxed region in FIG. 1f.

Figure 12:
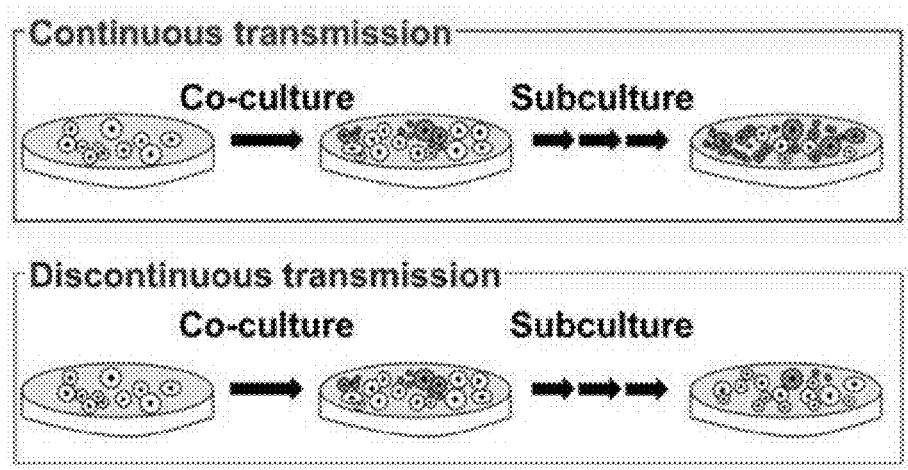

FIG. 12 illustrates projected outcomes of several passages of subcultures of a dual-cell BiFC system.

Figure 13:
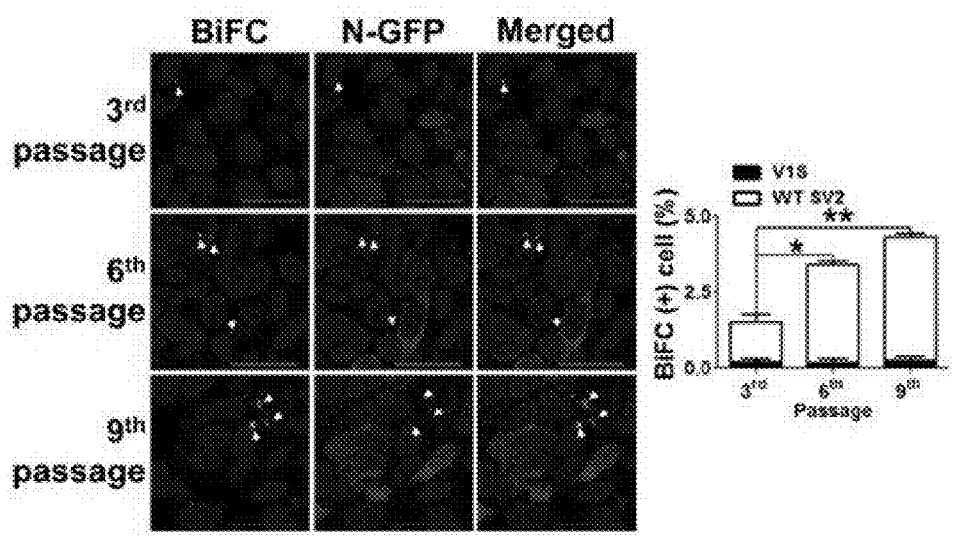

FIG. 13 illustrates distribution of BiFC fluorescence in V1S and SV2 cells.

Red fluorescence indicates the N-terminal fragment of Venus, thus V1S cells. The graphs on the right show BiFC fluorescence in V1S (white) and SV2 (black) cells. Distribution of BiFC fluorescence between V1S and SV2 cells was not changed. Scale bars: 20 μm, n=3, 1000 cells per each experiment, * $p<0.05$, ** $p<0.01$.

Figure 14:
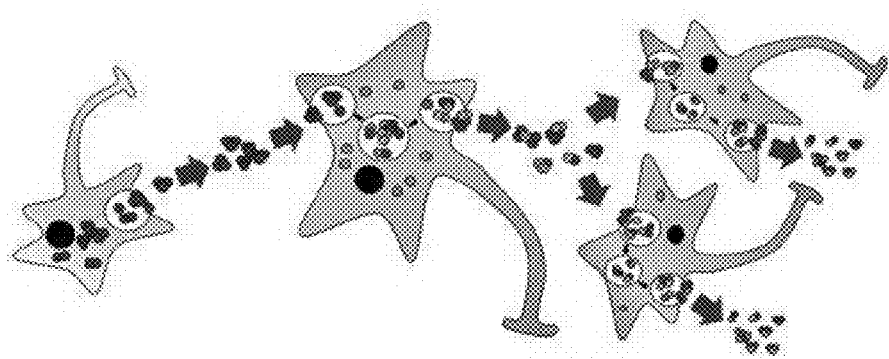

FIG. 14 illustrates a proposed model for contiguous transmission of α-synuclein aggregates.

Figure 15:
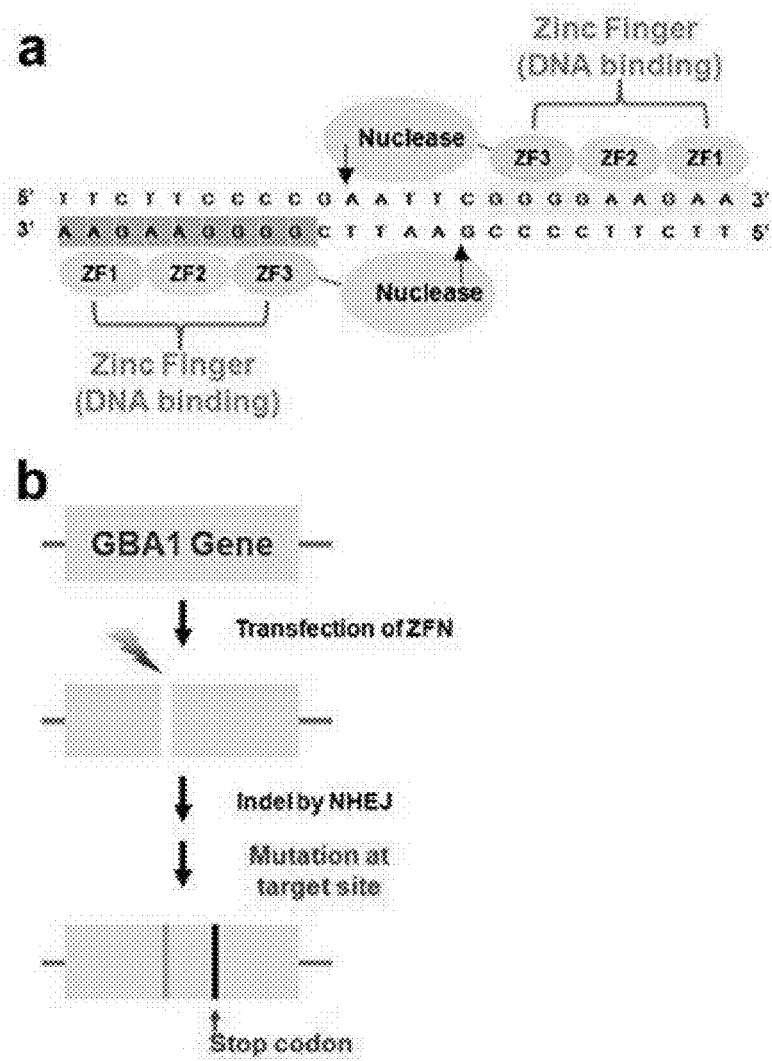

FIG. 15 illustrates targeted mutagenesis using zinc finger nuclease (ZFN). "a" of FIG. 15 shows that a pair of ZFNs, each of which recognizes a specific sequence in a target gene, is designed to cleave two strands of DNA. "b" of FIG. 15 shows that Nicks generated by ZFN are repaired by Non-Homologous End Joining (NHEJ), during which various mutations are introduced. Frame-shift mutations generate stop codons downstream of the ZFN target site.

Figure 16:
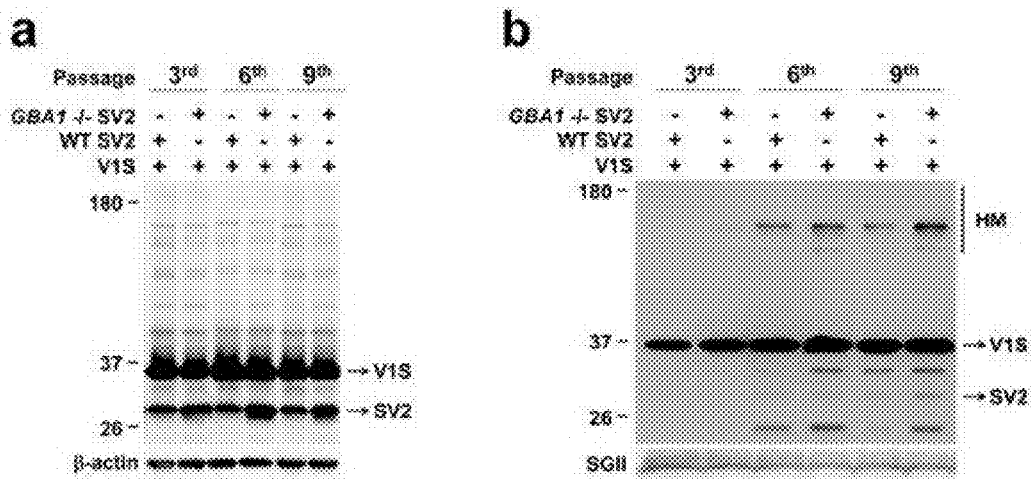

FIG. 16 shows that secretion of α-synuclein increased during successive subcultures of a dual-cell BiFC system.

The levels of secreted α-synuclein were analyzed by western blotting. FIG. 16(a) illustrates cell lysates. Intracellular levels of α-synuclein were not changed significantly. FIG. 16(b) illustrates culture media. Secretion of high molecular α-synuclein (HM) increased during successive subcultures of the dual-cell BiFC system.

Figure 17:
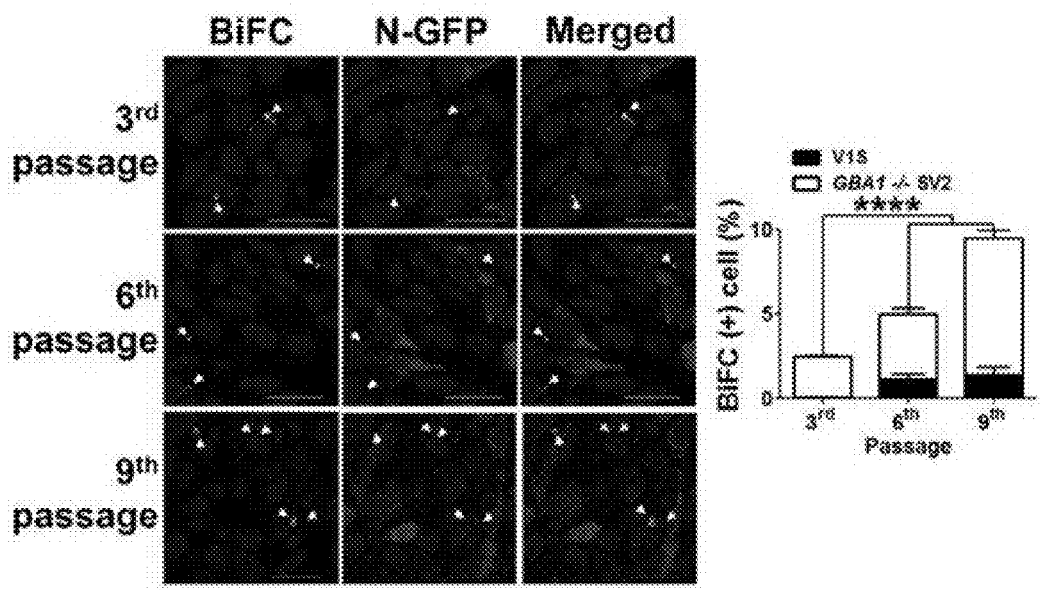

FIG. 17 illustrates distribution of BiFC fluorescence in V1S and SV2 GBA1−/− cells.

Red fluorescence indicates an N-terminal fragment of Venus, thus V1S cells. The graphs on the right show BiFC fluorescence in V1S (white) and GBA1−/−SV2 (black) cells. Distribution of BiFC fluorescence between V1S and GBA1−/−SV2 cells was not changed significantly during successive subcultures. Scale bars: 20 μm, n=3, 1000 cells per each experiment, * p<0.05, ** p<0.001.

Figure 18:
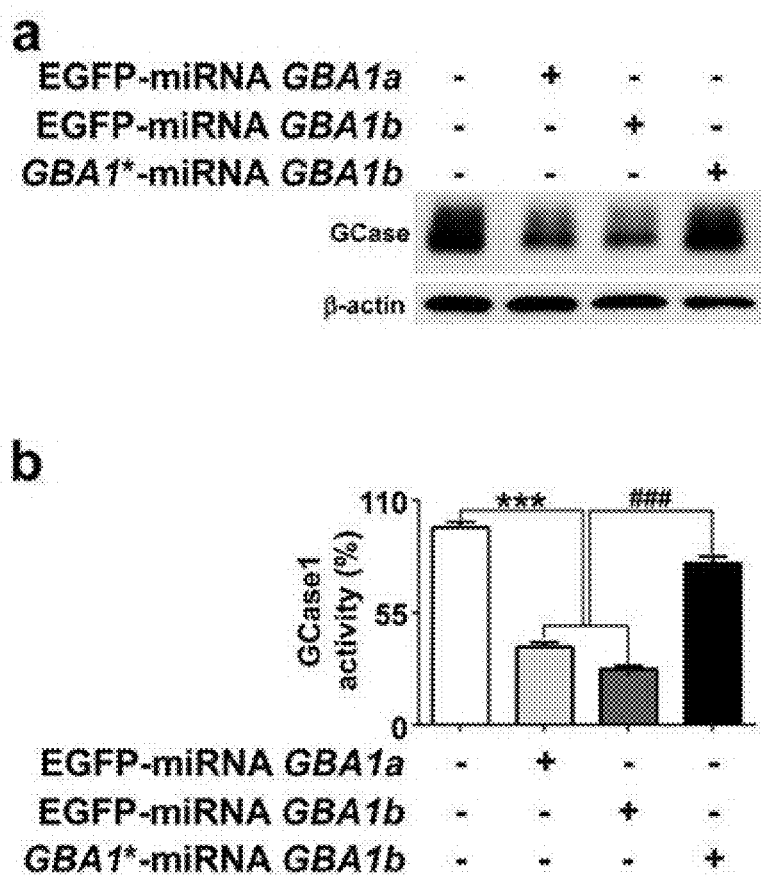

FIG. 18 illustrates efficiency of GBA1 knockdown. "a" of FIG. 18 shows that efficiency of GBA1 knockdown was analyzed by western blotting. "b" of FIG. 18 shows that efficiency of GBA1 knockdown was analyzed by GCase1 activity analysis. n=3, ***p<0.005, ### p<0.005.

Figure 19:
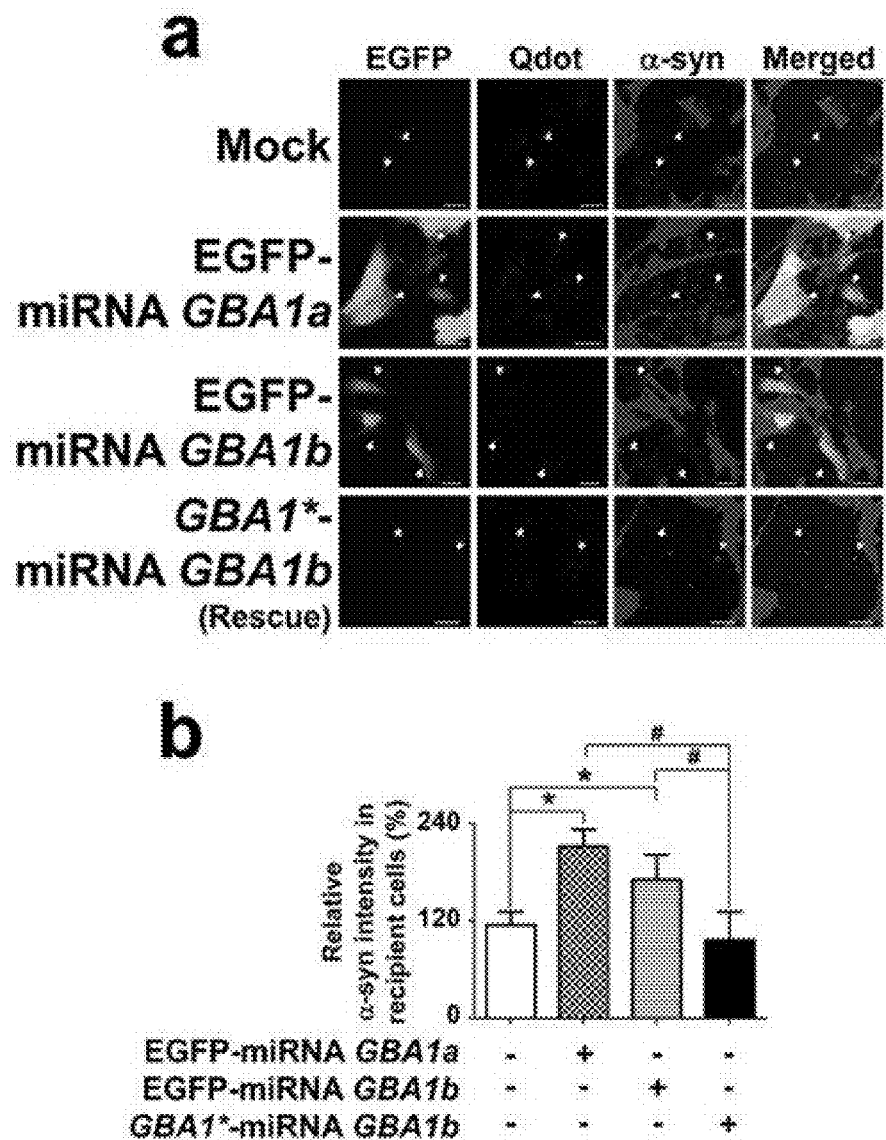

FIG. 19 illustrates effects of GBA1 knockdown on cell-to-cell transmission of α-synuclein. "a" of FIG. 19 shows that differentiated SH-SY5Y cells (donor) expressing α-synuclein were co-cultured with cells (recipient) expressing shRNAs for GBA1 knockdown. Vectors for shRNAs also contained GFP to label transfected cells. To rescue the effects of shRNAs, a separate vector was constructed in which GFP gene was replaced with GBA1 gene. Recipient cells were also labeled with Qdot. Recipient cells with transferred α-synuclein are indicated with arrowheads. Scale bars: 20 μm. "b" of FIG. 19 shows that α-synuclein immunofluorescence was measured in recipient cells; n=4, 500 cells per each experiment, *p<0.05, # p<0.05.

Figure 20:
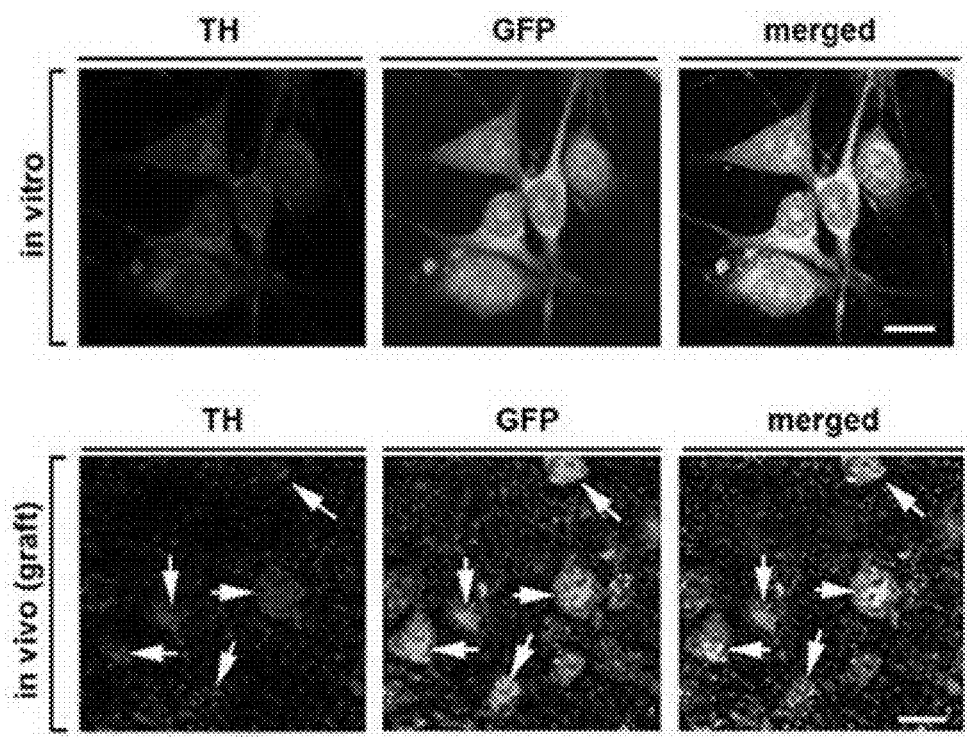

FIG. 20 illustrates assessment of grafted SH-SY5Y cells in a transplantation experiment.

To assess the grafted cells in the transplanted mouse brain tissues, differentiated SH-SY5Y cells were infected with GFP lentivirus prior to the transplantation. In in vitro experiments, 95% of GFP-positive cells were TH-positive. In the mouse hippocampus grafted with SH-SY5Y cells overexpressing GFP, about 80% of the grafted SH-SY5Y cells were TH-positive.

Figure 21:
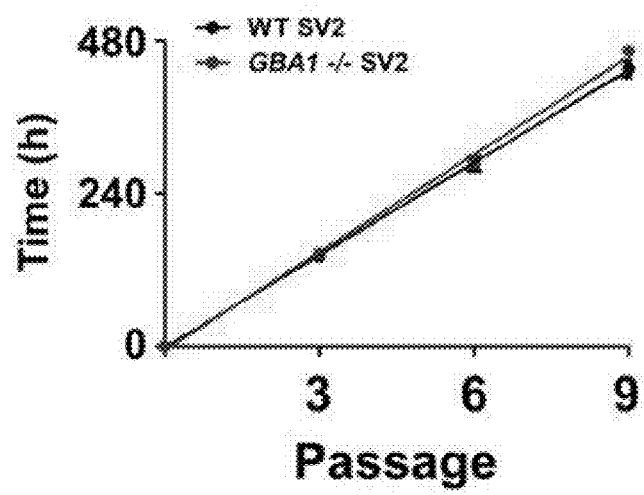

FIG. 21 illustrates proliferation rates of SV2 and GBA1-/-SV2 cells.

FIG. 22 illustrates construction of nucleotide sequence of fusion proteins V1S (Venus1-αSyn) and SV2 (αSyn-Venus2).

FIGS. 23*a* to 23*m* illustrate preparation and characterization of *C. elegans* model of the present disclosure for transmission of synucleinopathy.

Figure 24A:
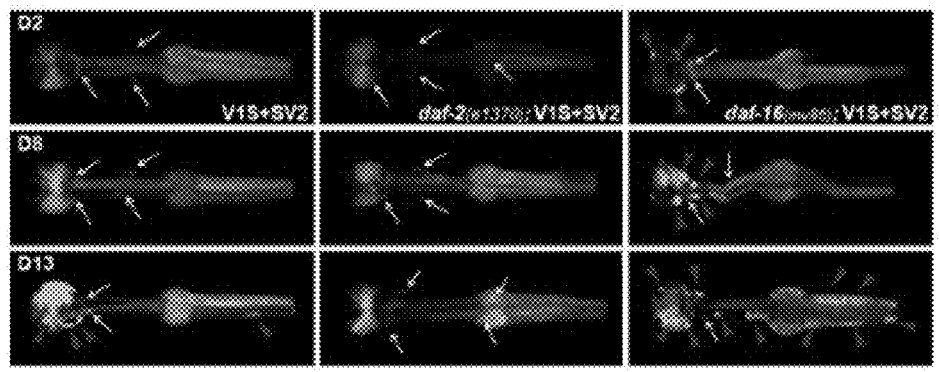
Figure 24B:
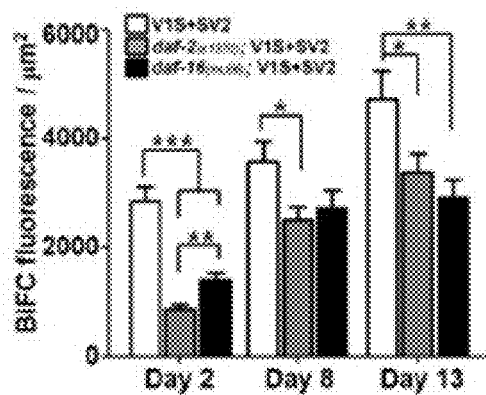
Figure 24C:
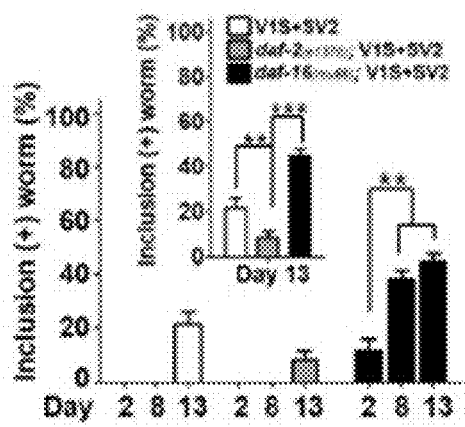
Figure 24D:
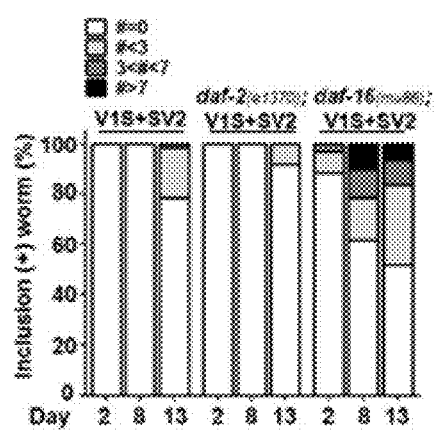
Figure 24E:
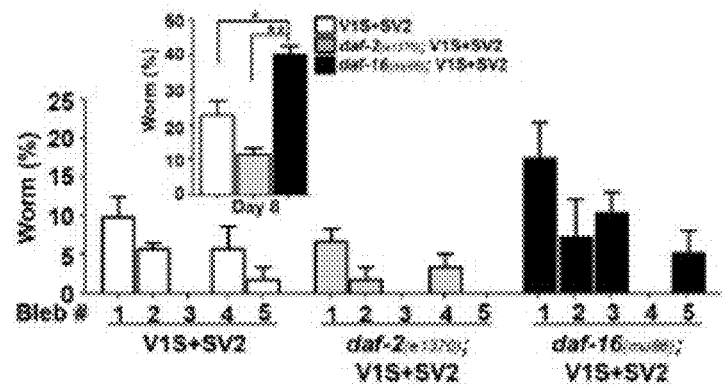
Figure 24F:
Figure 24G:
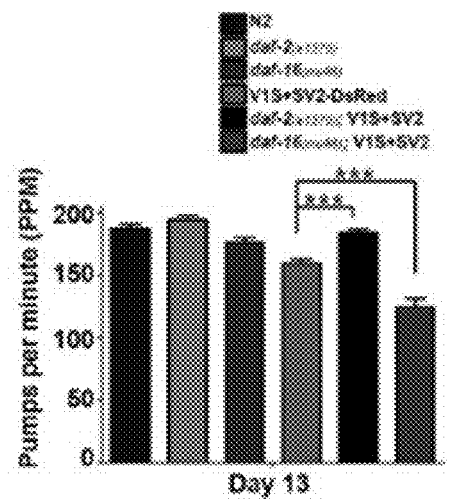
Figure 24H:
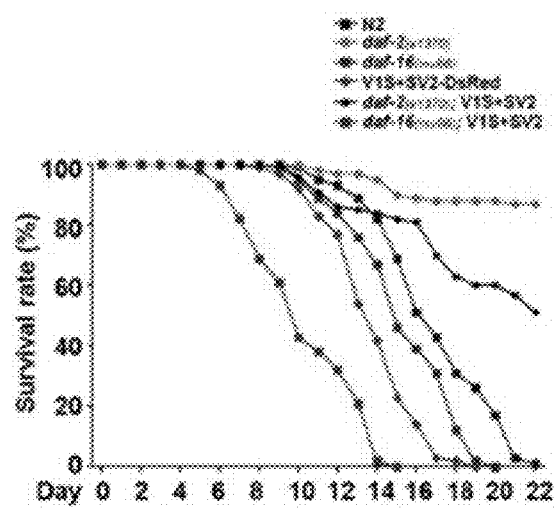

FIGS. 24*a* to 24 *h* are experimental results showing effect of daf-2, daf-16 mutations on cell-to-cell transmission of α-synuclein.

Figure 25A:
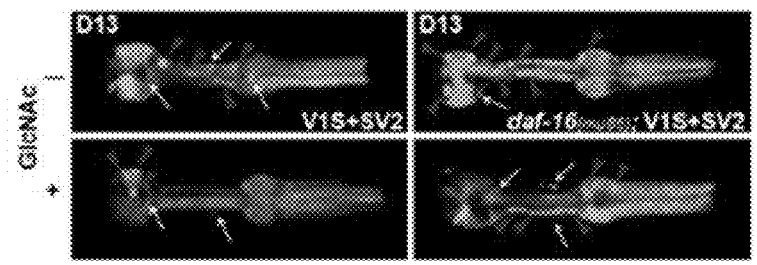
Figure 25B:
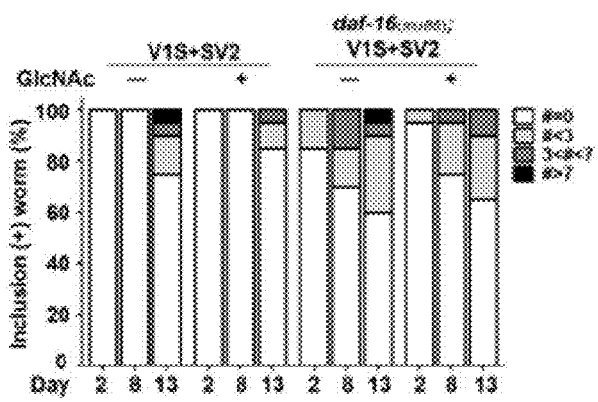
Figure 25C:
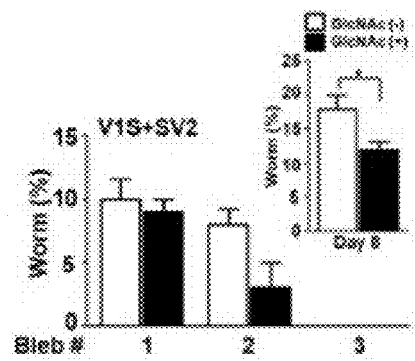
Figure 25D:
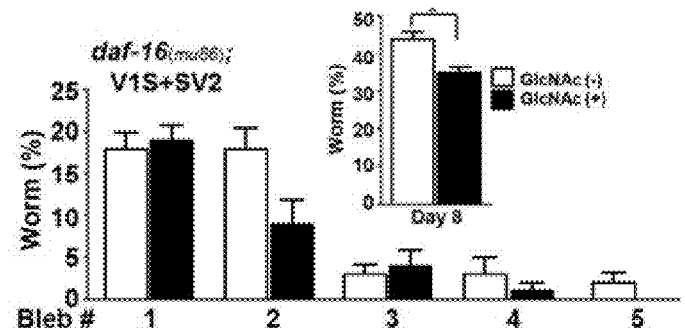
Figure 25E:
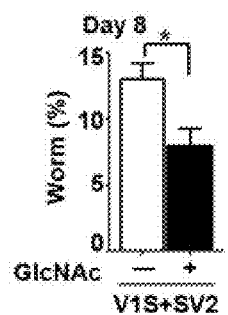
Figure 25F:
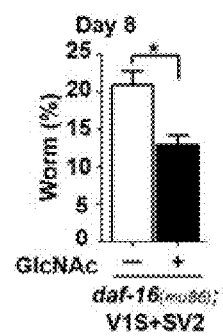
Figure 25G:
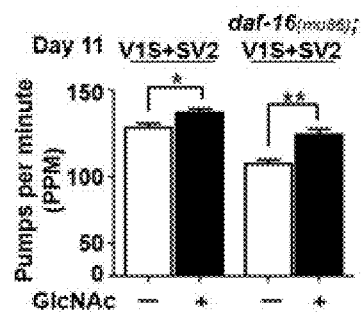

FIGS. 25*a* to 25 *h* are experimental results showing effects of GlcNAc on cell-to-cell transmission of α-synuclein.

FIGS. 26*a* to 26*h* are experimental results showing changes in steady-state levels of polyubiquitinated proteins by anti-aging treatment.

Figure 27A:
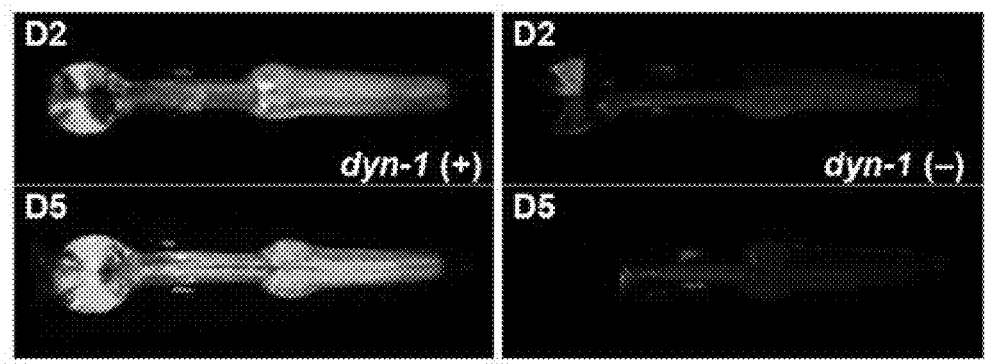
Figure 27B:
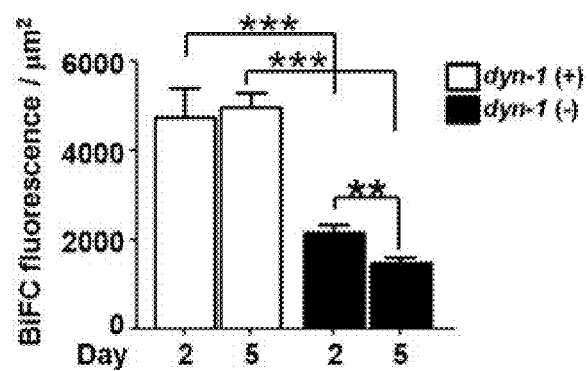
Figure 27C:
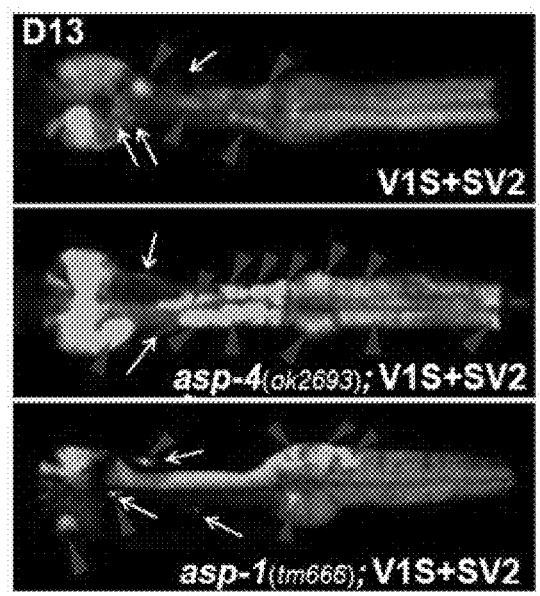
Figure 27D:
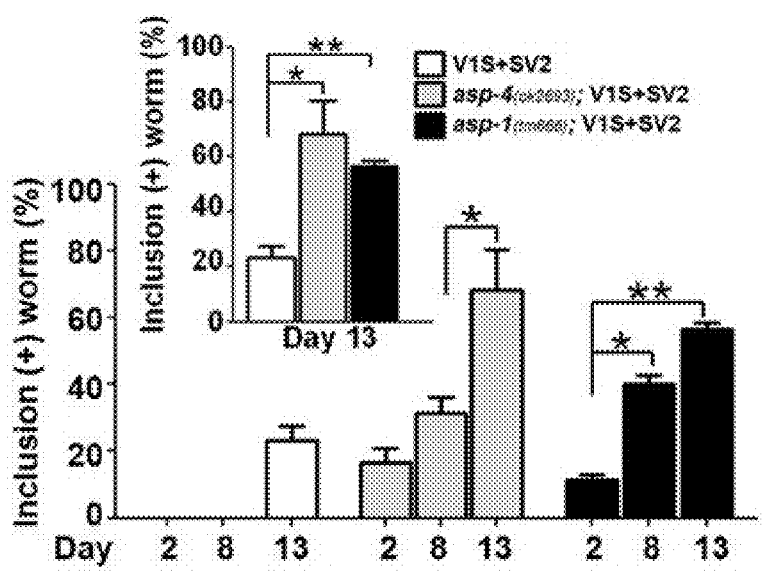
Figure 27E:
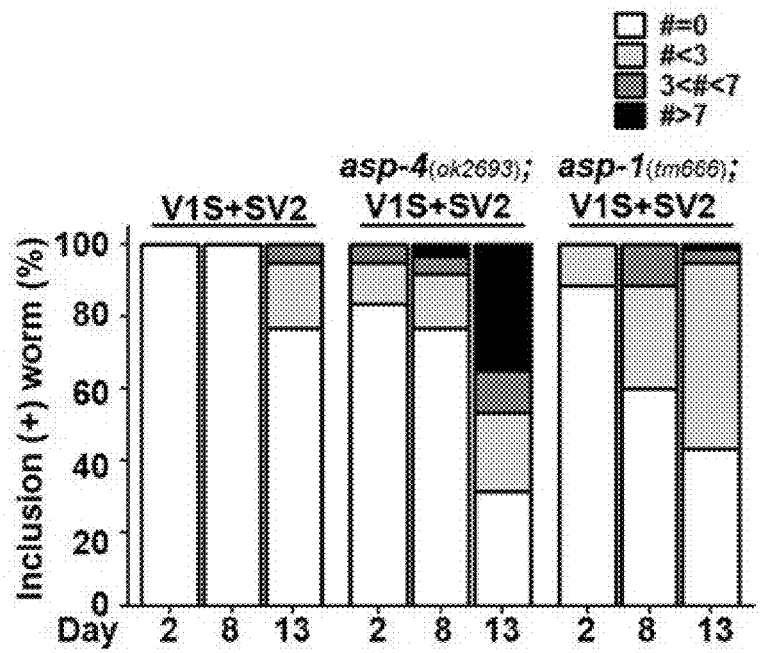
Figure 27F:
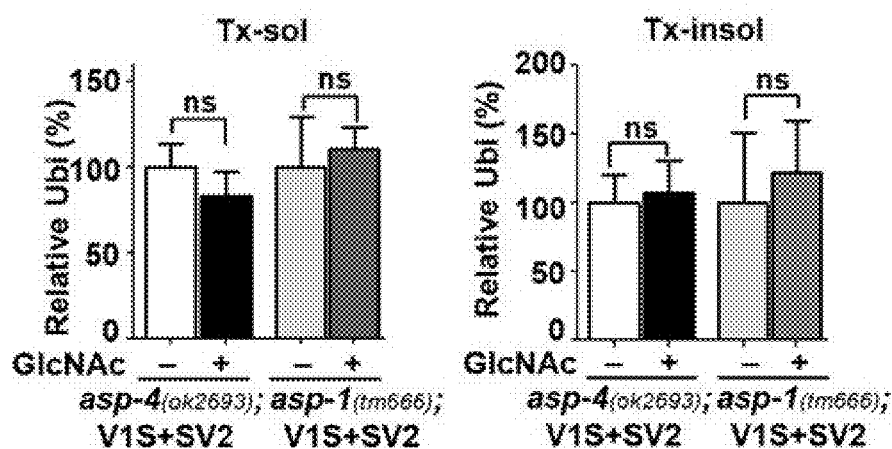
Figure 27G:
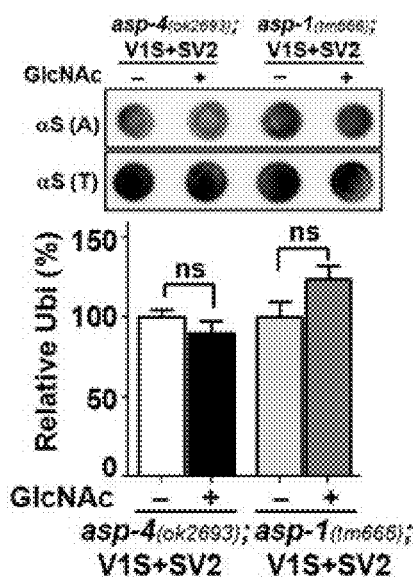
Figure 27H:
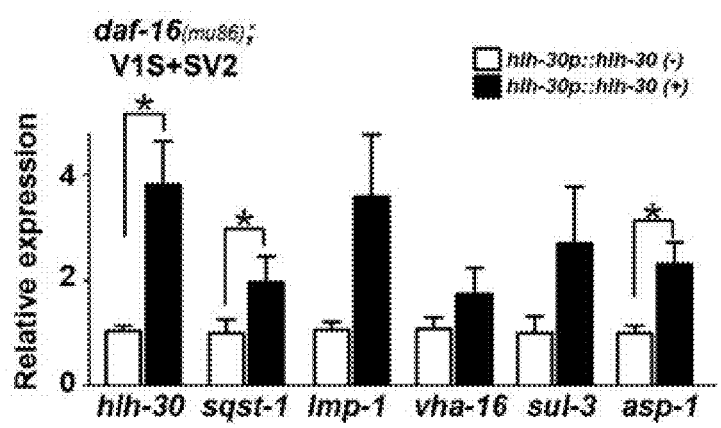
Figure 27I:
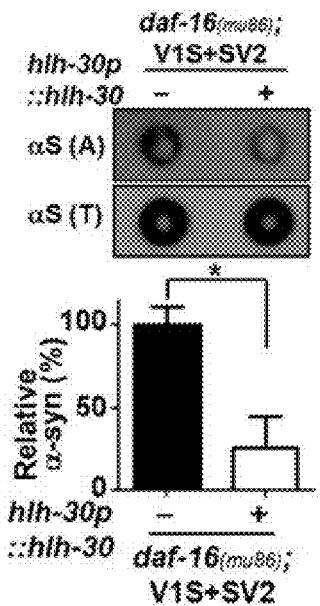
Figure 27J:
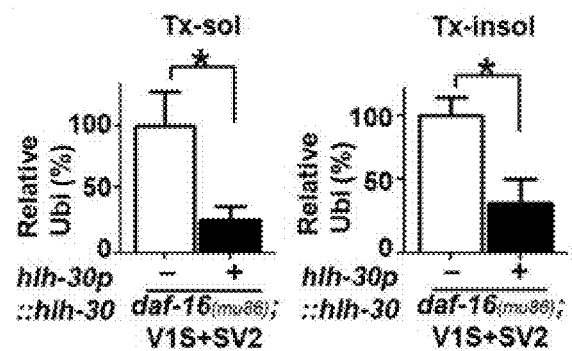
Figure 27K:
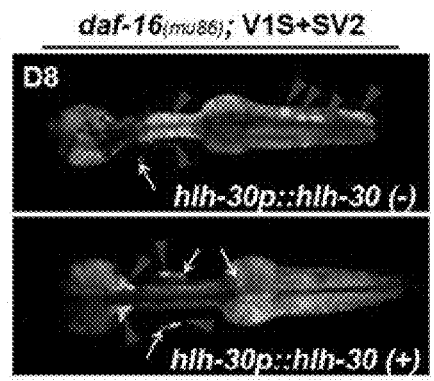
Figure 27L:
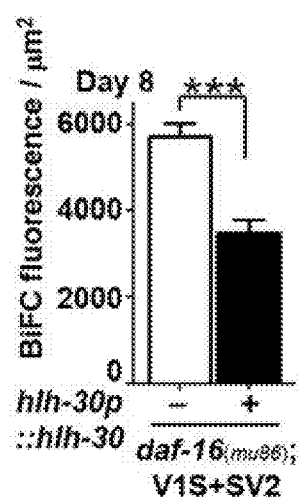
Figure 27M:
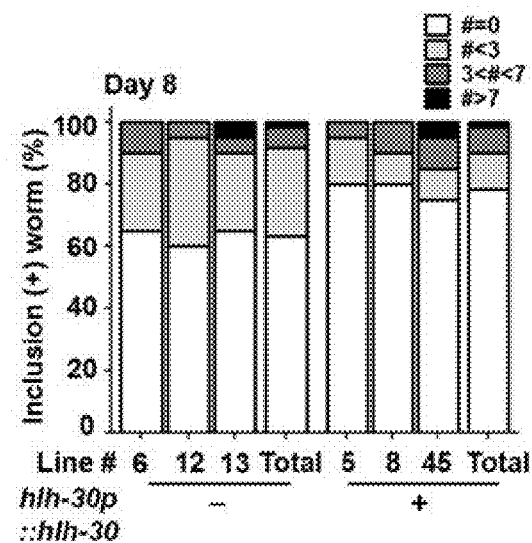
Figure 27N:
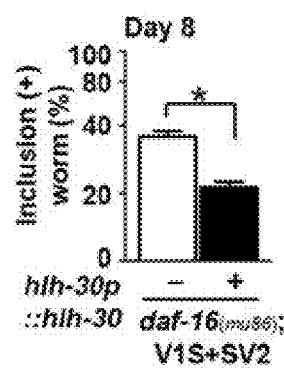
Figure 27O:
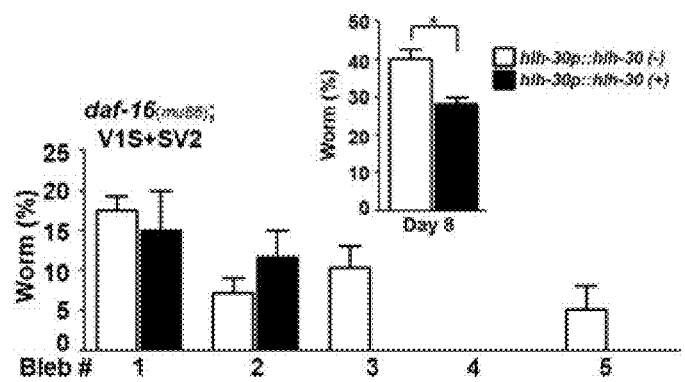
Figure 27P:
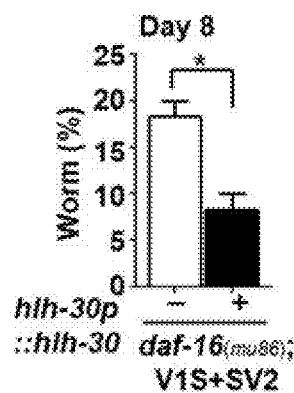
Figure 27Q:
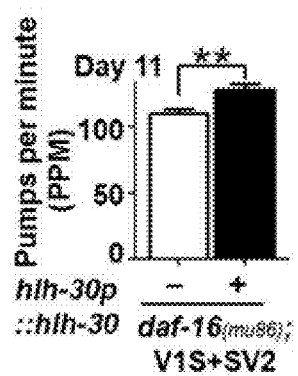
Figure 27R:
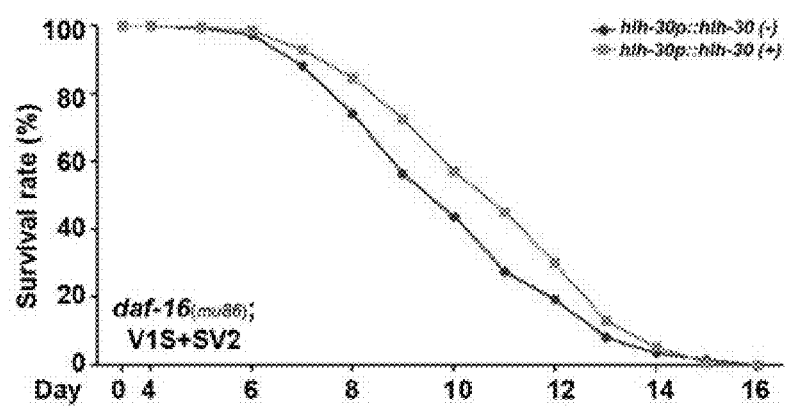

FIGS. 27*a* to 27*r* are experimental results showing that effects of anti-aging treatments on aggregate transmission are associated with enhanced lysosomal function.

Figure 28:
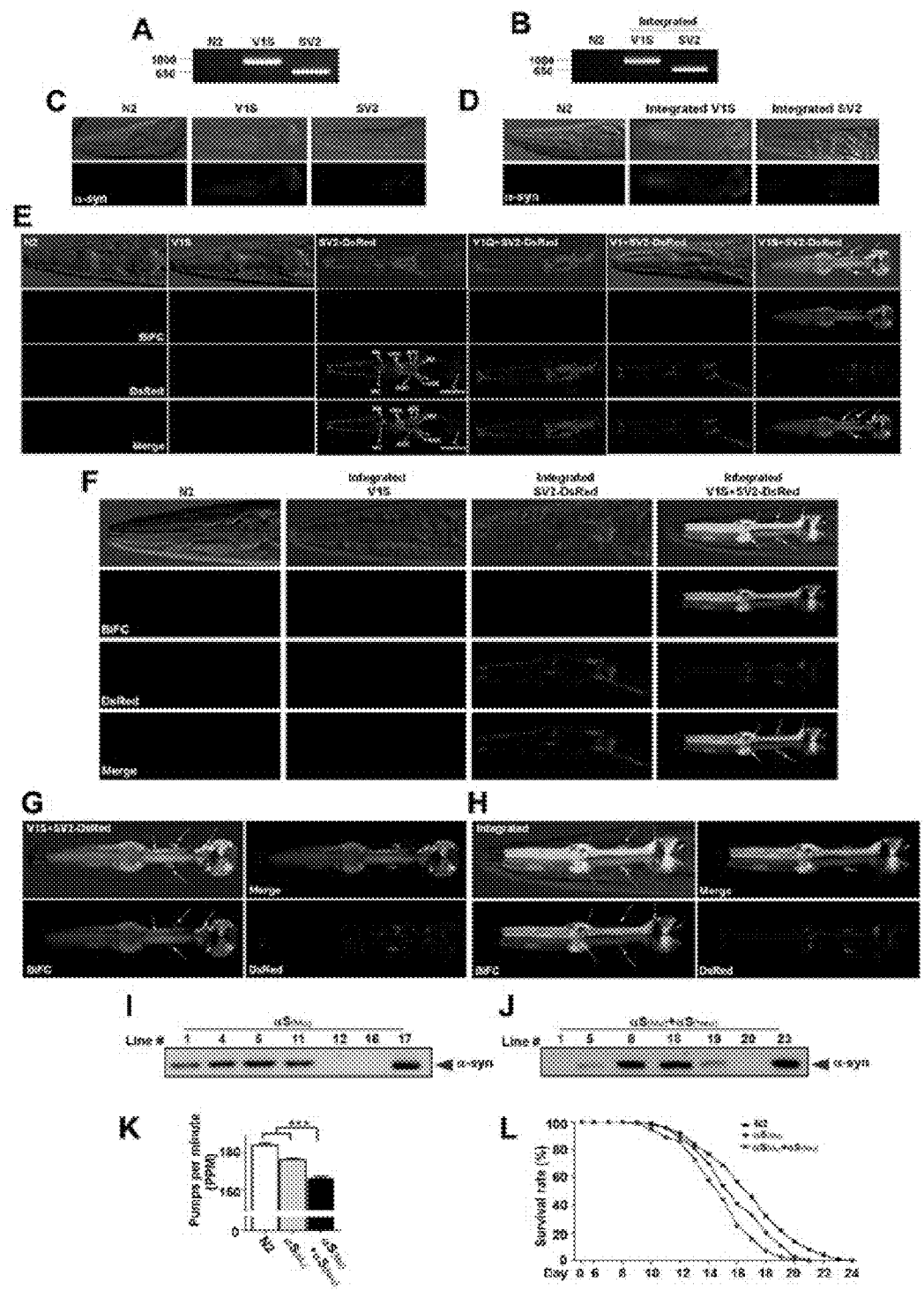

FIG. 28 is experimental results showing preparation and characterization of BiFC model in *C. elegans*.

Figure 29:
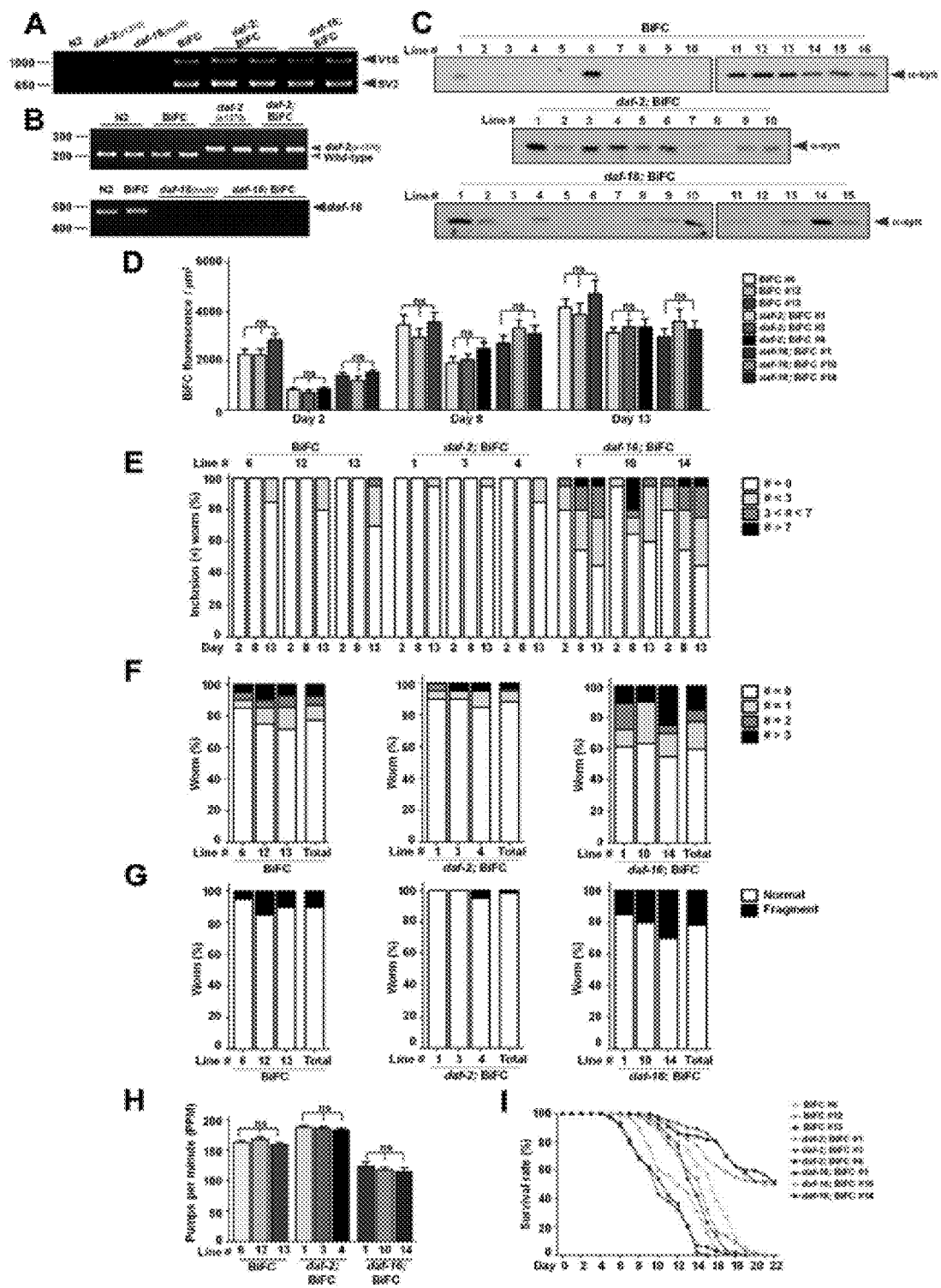

FIG. 29 is experimental results showing preparation and characterization of BiFC models in aging mutant *C. elegans*.

Figure 30:
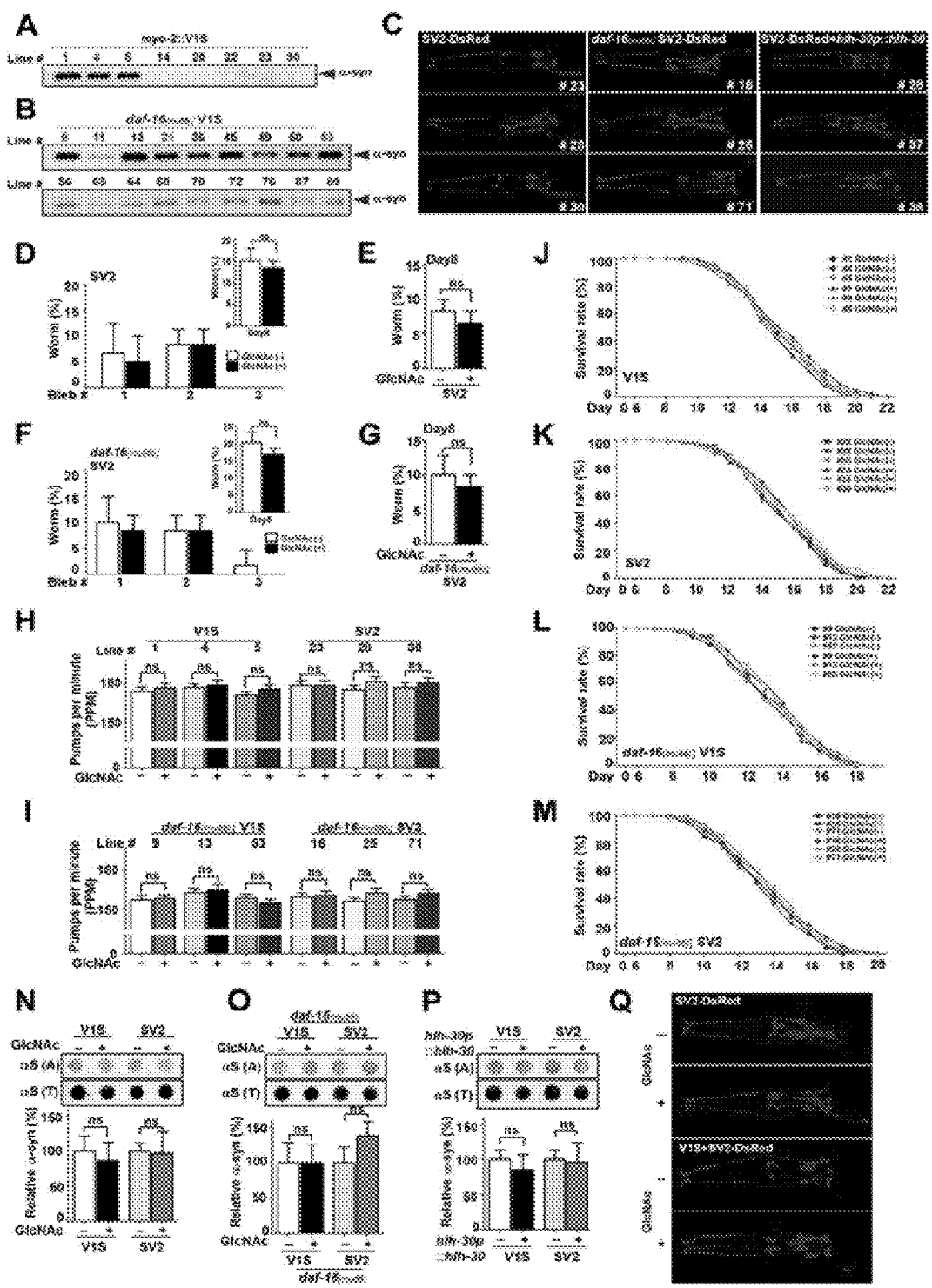

FIG. 30 is experimental results showing effect of GlcNAc in single tissue expression lines according to an embodiment of the present disclosure.

Figure 31:
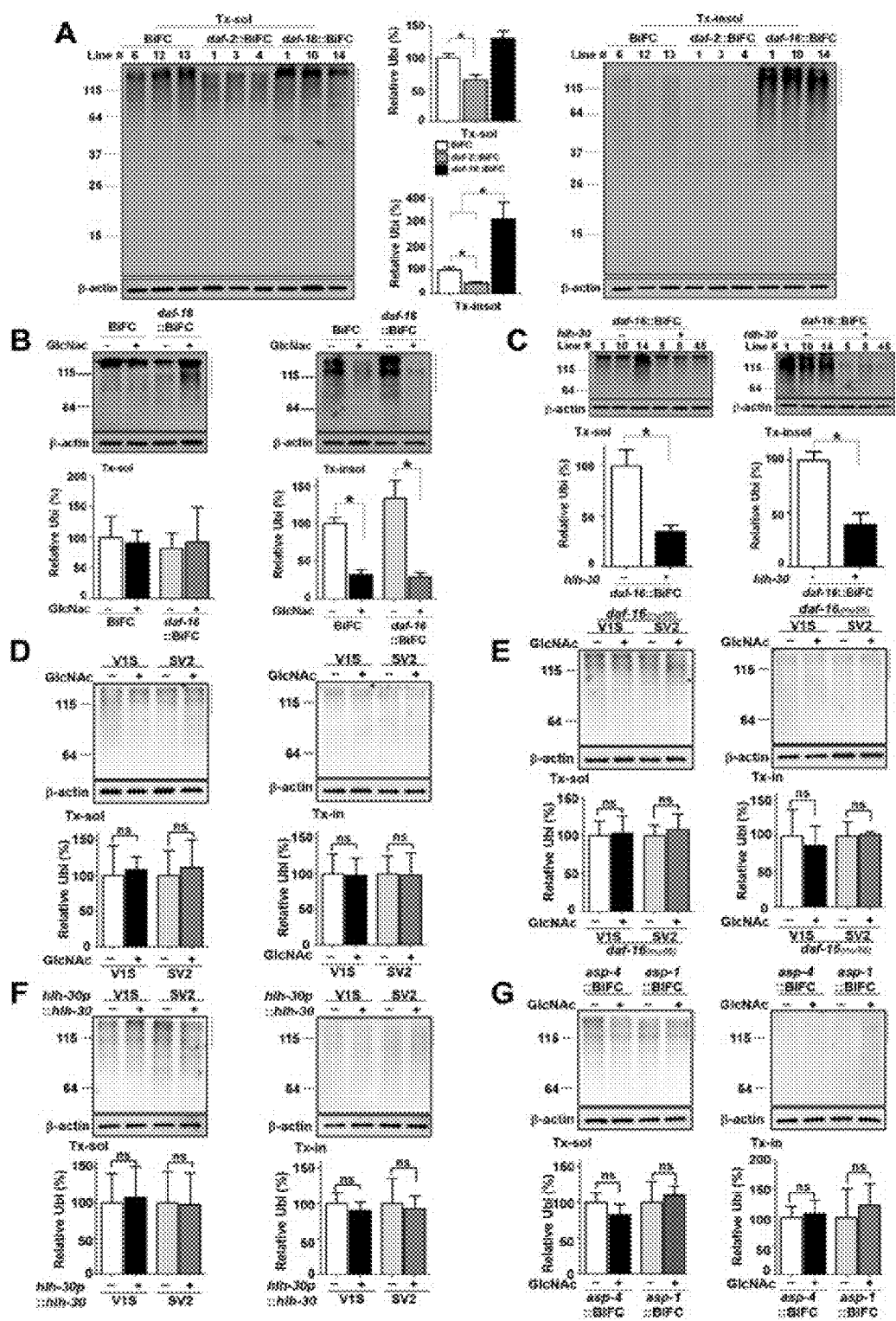

FIG. 31 is experimental results showing changes in steady-state levels of polyubiquitinated proteins, related to FIG. 26.

Figure 32:
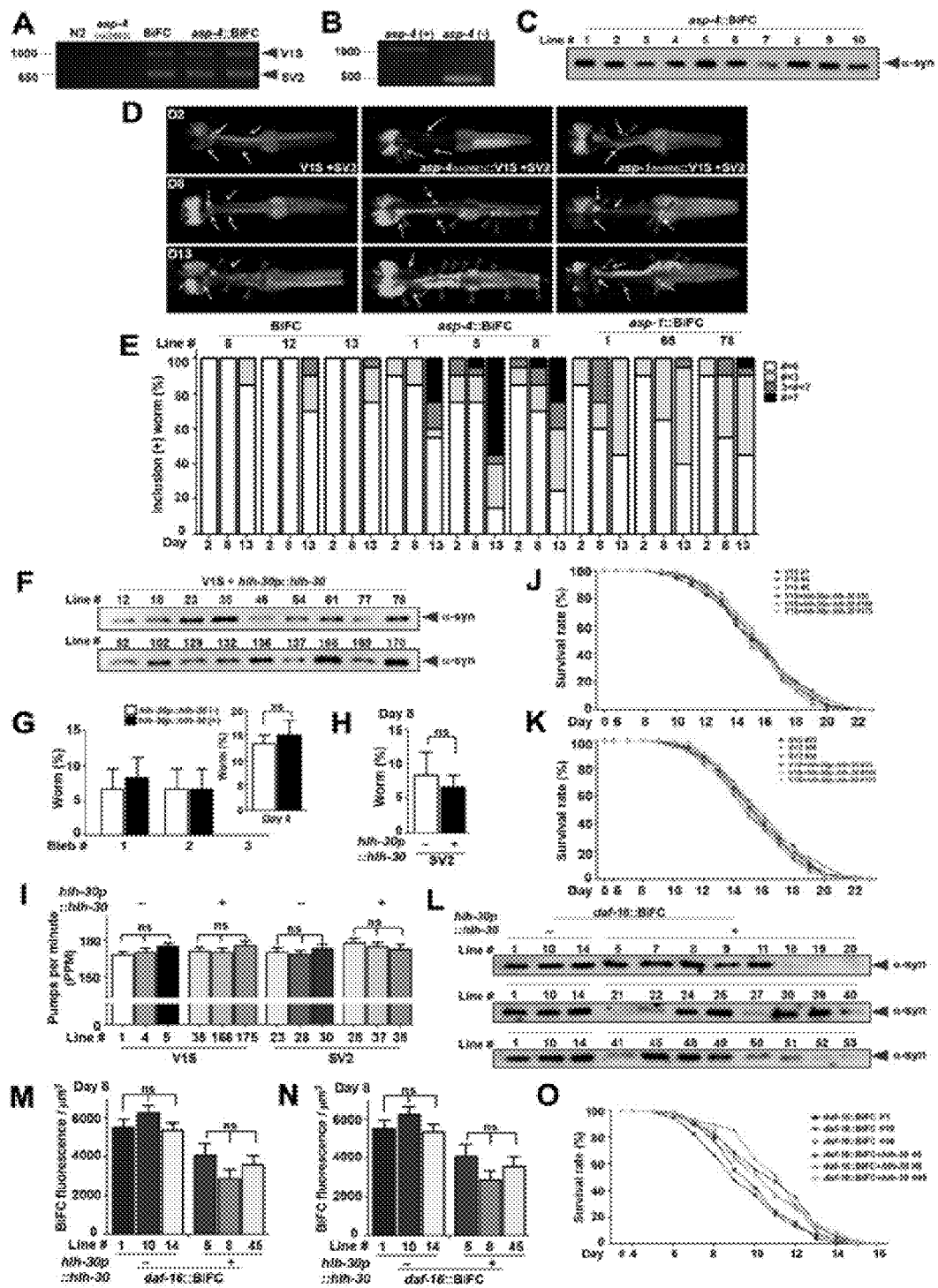

FIG. 32 is analysis results of endolysosomal functions of transgenic lines according to an embodiment of the present disclosure, related to FIG. 27.

DETAILED DESCRIPTION

Hereinafter, the present disclosure is described with reference to examples in detail. It should be understood, however, that the examples are provided only to specifically explain the present disclosure, and that the scope of the present disclosure is not limited to these examples.

EXAMPLE 1

Preparation of Dual-Cell Model and Measurement of Cell-to-Cell Transmission of α-Synuclein Using the Same Experimental Materials and Processes The following antibodies were used in the present disclosure: ☐☐-synuclein monoclonal antibody (BD Biosciences; #610787, San Diego, Calif.), ☐☐-synuclein monoclonal antibody #274, phosphorylated ☐-synuclein polyclonal antibody (Abcam, ab59264; Cambridge, Mass.), GFP (c-terminus) polyclonal antibody (IMGENEX, #5127A; San Diego, Calif.), GFP (N-terminus) polyclonal antibody (Cell signaling Technology, #2555; Beverly, Mass.), GFP (N-terminus) monoclonal antibody (Abcam, ab127417), GCase monoclonal antibody 8E4 (from J. Barranger, University of Pittsburgh), GCase polyclonal antibody (Sigma, G4171; St. Louis, Mo.), p62 monoclonal antibody (BD Transduction laboratories, #c2384-0B; Swampscott, Mass.), ubiquitin polyclonal antibodies (Dako; Glostrup, Denmark and Chemicon; Temecula, Calif.), and β-actin monoclonal antibody (Sigma). Fluorescence dye-conjugated goat anti-rabbit IgG was purchased from Jackson Immunoresearch Laboratories (West Grove, Pa.). The Q tracker 858 cell labeling kit was purchased from Invitrogen (Carlsbad, Calif.).

Example 1-1. Construction of Stable Cell Lines

To prepare stable cell lines, SH-SY5Y human neuroblastoma cells were transfected with Venus1-αSyn (V1S) or ☐Syn-Venus2 (SV2) (obtained from Dr. Pamela McLean, Massachusetts General Hospital, Charlestown, Mass.) using electroporation. Transfected cells were selected with 600 mg/mL G418 (Invitrogen) for 2-3 weeks until colonies emerged. The stable cell lines were maintained with 200 g/mL G418.

Example 1-2. Preparation of GBA1 Knockout (KO) Cell Lines

SH-SY5Y cells were transfected with plasmids encoding ZFN and a magnetic reporter (ToolGen; Seoul, Korea) using electroporation. After incubation for 48 h, the cells were subjected to magnetic separation. After trypsinization, the cells were mixed with magnetic bead-conjugated antibody against H-2K$^k$ (MACSelectKkmicrobeads; Miltenyi Biotech; Germany) and the mixture was applied to a MACS LS column (Miltenyi Biotech). Single cells obtained from the eluates were maintained until the clonal colony was picked from the culture dish. Nonsense mutations in the GBA1 gene were confirmed using DNA sequencing.

Example 1-3. Cell Culture

SH-SY5Y human neuroblastoma cell lines were maintained as described previously (Lee, H. J. et al. 2004 J. Neurosci. 24, 1888-1896). For co-culture, V1S and SV2 (or SV2GBA1-/-) stable cells (180,000 cells each) were mixed in a coverslip and cultured for 3 days. In order to determine the continuous transmission of α-synuclein, the mixture of V1S and SV2 (or SV2GBA1-/-) cells was subcultured every 2 days (48 h). Growth rates of SV2 and SV2GBA1−/− were not significantly different during the passage experiment (FIG. 21).

To determine the effects of media washing on transmission, the V1S/SV2 co-culture was washed with Dulbecco's modified Eagle medium (DMEM) and incubated with fresh growth media the day prior to assay. To determine the effects of antibodies on the transmission of α-synuclein, 5 µg/mL of control IgG or Ab274 was added to V1S/SV2 co-culture the day prior to the assay.

Example 1-4. Preparation of α-Synuclein Conditioned Media

The α-synuclein conditioned media were obtained from 20 dishes of 100 mm. When V1S cells are 90% confluent, the media were replaced with serum free DMEM after washing three times with DMEM. Cells were incubated at 37° C. for 18 h. Conditioned media (100 mL) was collected from 20 dishes of V1S cells. After centrifugation at 1,000×g for 10 min, supernatant was centrifuged at 10,000 for 20 min to remove the cell debris. The supernatant was concentrated to 300 fold using Amicon 10K MWKO filter (Millipore, Billerica, Mass.).

Example 1-5. Size Exclusion Chromatography

Size exclusion chromatography was performed using AKTA purifier (GE Healthcare Life Science, Piscataway, N.J.). Samples were applied to Superdex 200 HR 10/30 column (GE Healthcare Life Science) equilibrated with phosphate buffer (20 mM sodium phosphate, pH 7.4, 0.15 M NaCl) and eluted at a flow rate of 0.5 mL/minute.

Example 1-6. Quantification of GCase Activity and Glycosphingolipid Levels

Cellular GCase activity was measured as described previously using 4-methylumbelliferyl (4-MU)-β-D-glucoside as an artificial substrate (Sardi, S. P. et al. 2011 *Proc Natl Acad Sci USA* 108, 12101-12106). All measurements were done without taurocholate, a detergent that activates the GCase enzymatic activity. GCase2 specific activity was measured in the presence of the GCase1 inhibitor, conduritol-B-epoxide (100 µM). GCase1 activity was obtained by subtracting the GCase2 activity levels from the total GCase activity. Cellular GlcCer and GalCer levels were measured using mass spectrometry as previously described (Sardi, S. P. et al. 2011 *Proc Natl Acad Sci USA* 108, 12101-12106). Briefly, organic cellular extracts were injected onto an Atlantis HILIC silica column (Waters Corp.; Milford, Mass.) for separation of GlcCer and GalCer, which were detected using an AB Sciex API-5000 mass spectrometer.

Example 1-7. Infection with Adeno-Associated Virus (AAV) Vectors

After passage, cells were co-infected with Ad-TS129 (3 M.O.I.) and various AAV (5e6 M.O.I.). The cells were incubated at 39° C. for 24 h for activation of the temperature-sensitive helper adenovirus. Several AAV vectors were designed for knockdown of GBA1 (GFP-miRNAGBA1a and b) and a rescue vector expressing a miRNA-resistant GBA1* (GBA1*-miRNAGBA1b).

Example 1-8. Quantification of Secreted α-Synuclein Aggregates

To measure the level of secreted α-synuclein co-aggregates, culture medium obtained from V1S/SV2 co-culture was centrifuged at 10,000×g for 10 min. The supernatant obtained from culture media was transferred to a 96-well black plate (Corning Inc.; Corning, N.Y.) and subjected to fluorescence analysis using a fluorescence microplate reader (SpectraMax Gemini EM; Molecular Devices, Sunnyvale, Calif.). The procedure for ELISA was performed as described previously (Lee, H. J. et al. 2011 *J Neurosci Methods* 199, 249-257). Briefly, 1 µg/mL of the capture antibody #62 in 50 mM carbonate buffer (pH 9.6) was coated on a 96-well ELISA plate (Maxisorp, Nunc; Rochester, N.Y.) overnight at 4° C. After washing with phosphate-buffered saline (PBS) containing 0.05% Tween 20 (PBST), SuperBlock T20 PBS blocking buffer (Pierce; Rockford, Ill.) was added for 1 h at room temperature (RT) with shaking. After washing with PBST, α-synuclein aggregates obtained from the standard and culture media were incubated at RT for 2.5 h with shaking. Plates were washed again with PBST, after which 1 µg/mL of biotinylated reporter antibody #62 was added and incubated at RT for 1.5 h. After washing with PBST, avidin-conjugated peroxidase (ExtrAvidin; Sigma; St. Louis, Mo.) was added to the plate. The plate was then incubated with 3,3',5,5'-tetramethylbenzidine solution (Sigma). After addition of 2N $H_2SO_4$, absorbance was measured at 490 nm using a SpectraMax 190 spectrophotometer (Molecular Devices).

Example 1-9. Preparation of Cell Extracts

After washing with ice-cold PBS, cells were lysed in extraction buffer (1% Triton X-100, 1% (v/v) protease inhibitor cocktail (Sigma) in PBS). Cell lysates were incubated on ice for 10 min and centrifuged at 16,000×g for 10 min. The Triton X-100 soluble fraction was resuspended in 1× Laemmli sample buffer and sonicated briefly.

Example 1-10. Western Blotting

Western blotting was performed as previously described (Lee, H. J. et al. 2002 *J Biol Chem* 277, 48976-48983). Images were obtained and quantified using the FUJIFILM Luminescent Image Analyzer LAS-3000 and Multi Gauge (v3.0) software (FUJIFILM; Tokyo, Japan).

Example 1-11. Immunofluorescence Staining

The procedure for immunofluorescence staining was performed as previously described (Lee, H. J. et al. 2002 *J Biol Chem* 277, 48976-48983). Briefly, cells grown on poly-L-Lysine-coated coverslips were fixed in 4% paraformaldehyde in PBS and permeabilized in 0.1% Triton X-100 in PBS. After incubation in blocking solution (5% bovine serum albumin/3% goat serum in PBS), primary antibodies diluted in the blocking solution were added to cells. After washing, the cells were incubated with fluorescent dye-conjugated secondary antibodies. Nuclei were stained with TOPRO-3 iodide (Invitrogen). Cells were mounted onto slide glasses in the presence of Prolong GoldAntifade Reagent (Invitrogen). Olympus FV1000 confocal laser scanning microscopy was used for observation of cells.

Example 1-12. Characterization of Lysosomal Dysfunction

For imaging of the lysotracker-positive compartment, SH-SY5Y cells were stained with 75 nM lysotracker solution in dimethyl sulfoxide (Lysotracker Red DND-99; Invitrogen) diluted in growth media, and incubated for 1 h at 37°

C. in a CO2 incubator. After washing with ice-cold PBS, cells were fixed in a 4% paraformaldehyde (PFA) solution. In order to determine the degradation ratio of internalized dextran, cells were incubated with 20 µg/mL of fluorescein isothiocyanate (FITC)-labeled dextran (Invitrogen) for 2 h. After washing with DMEM, the cells were incubated with fresh growth media for 30 min and fixed with a 4% PFA solution. The fluorescence intensity was measured using Olympus FV1000 software.

Example 1-13. Electron Microscopy

Cells were grown in 100-mm dishes and fixed in the Karnovsky's fixative solution (2% glutaraldehyde, 2% paraformaldehyde, 0.5% $CaCl_2$). After immersing in 1% osmium tetraoxide for 1.5 h, cells were dehydrated with 50%, 60%, 70%, 80%, 90%, 95%, and 100% of ethanol. Cells were infiltrated with propylene oxide and EPON mixture (EPON 812, MNA, DDSA, DMP30) for 10 min prior to embedding EPON mixture. After embedding, the cells were sectioned with LEICA EM UC-7 Ultra-microtome (Leica Microsystems, Austria), then stained with 6% uranyl acetate and lead citrate. The grids were observed using transmission electron microscopy JEM-1011 (JEOL; Japan) and analyzed using Megaview III software (Soft imaging system, Germany). For morphometric analysis, 15 cells were analyzed for each experiment.

Example 1-14. Analysis of Externally Added Recombinant α-Synuclein Aggregates in Cells Cells were incubated with 0.2 µM of α-synuclein fibrils for 1 day and fixed with 4% PFA. After immunofluorescence staining, the intensity of α-synuclein in a single cell was measured using Olympus FV1000 software.

Example 1-15. Animals

For this study, heterozygous transgenic mice (Line 61) expressing wild type human α-synuclein were used under the control of the mThy1 promoter (Rockenstein, E. et al. 2002 *J Neurosci Res* 68, 568-578). These mice were selected since they display extensive neuronal and synaptic accumulation of α-synuclein aggregates throughout the neocortex, limbic system, and striato-nigral system, accompanied by motor and non-motor deficits similar to those observed in patients with PD and dementia with Lewy-Bodies (Fleming, S. M. et al. 2004 *J Neurosci* 24, 9434-9440).

Example 1-16. Stereotaxic Delivery of SH-SY5YGBA1-/- Cells into α-Synuclein Transgenic Mice α-synuclein transgenic mice and their non-transgenic litter mates (n=8 per group, 10-months-old, total 4 groups, 32 mice) received unilateral stereotaxic injections of a 2 µL suspension of wild type or GBA1-/- cell preparation (1.2 million cells) into hippocampus as previously described (Desplats, P. et al. 2009 *Proc Natl Acad Sci USA* 106, 13010-13015). Mice were anesthetized and placed on a Koft stereotaxic apparatus. Utilizing an electronic delivery pump system, SH-SY5Y or SH-SY5YGBA-/- cell preparations were injected using a Hamilton syringe. Coordinates for the hippocampus were as follows: AP -2.0 mm, lateral 1.5 mm, depth 1.3 mm. Mice survived for four weeks after the graft injection. Mice were anesthetized with chloral hydrate and flush-perfused transcardially with 0.9% saline. Brains were removed and fixed in phosphate-buffered 4% PFA (pH 7.4) at 4° C. for 48 h for neuropathological analysis.

Example 1-17. Immunocytochemical Analysis and Laser Scanning Confocal Microscopy Brains were serially sectioned at 40 µm using a vibratome (Leica; Deerfield, Ill., USA). Serial, free-floating, blind-coded vibratome sections obtained from transgenic and non-transgenic mice grafted with WT and SH-SY5YGBA1-/- cells were immunostained as previously described with antibodies against total α-synuclein (Millipore), α-synuclein c-terminus (SYN105 antibody), and human α-synuclein (SYN211) (Bae, E. J. et al. 2012 *J Neurosci* 32, 13454-13469). Sections were then incubated with biotin-tagged secondary antibodies and developed with diaminobenzidine. Sections immunolabeled with antibodies against α-synuclein (three from each mouse at 100-µm intervals) were analyzed via the dissector method using the Stereo-Investigator System (MBF Bioscience; Williston, Vt.) and the results were averaged and expressed as the percentage of positive cells in the grafted area.

To determine the co-localization between α-synuclein and neuronal markers, double-labeling experiments were performed, as previously described (Masliah, E. et al. 2011 *PLoS One* 6, e19338). For this purpose, vibratome sections were immunolabeled using antibody against human α-synuclein (SYN211) and antibodies against TH (Millipore) and GCase (Abcam, ab55080). The TH- and GCase-immunoreactive grafted cells were detected with FITC-tagged antibodies (1:75; Vector; Burlingame, Calif.), while α-synuclein was detected with Tyramide Red (NEN Life Sciences). All sections were processed simultaneously under the same conditions, and experiments were performed in duplicate in order to assess the reproducibility of results. Sections were imaged with a Zeiss 63X (N.A. 1.4) objective on an Axiovert 35 microscope (Zeiss) with an attached MRC1024 laser scanning confocal microscope (LSCM) system (BioRad) (Masliah, E. et al. 2011 *PLoS One* 6, e19338). Series of paired optical sections were analyzed with ImageJ co-localization color map software to determine the α-synuclein pixel intensity associated with WT and GBA1-/- cells. An average of 20 digital images was analyzed per mouse. Each digital image contained an average of 4 cells. Values in the figures are expressed as means±SEM.

Experimental Results

Figure 8:
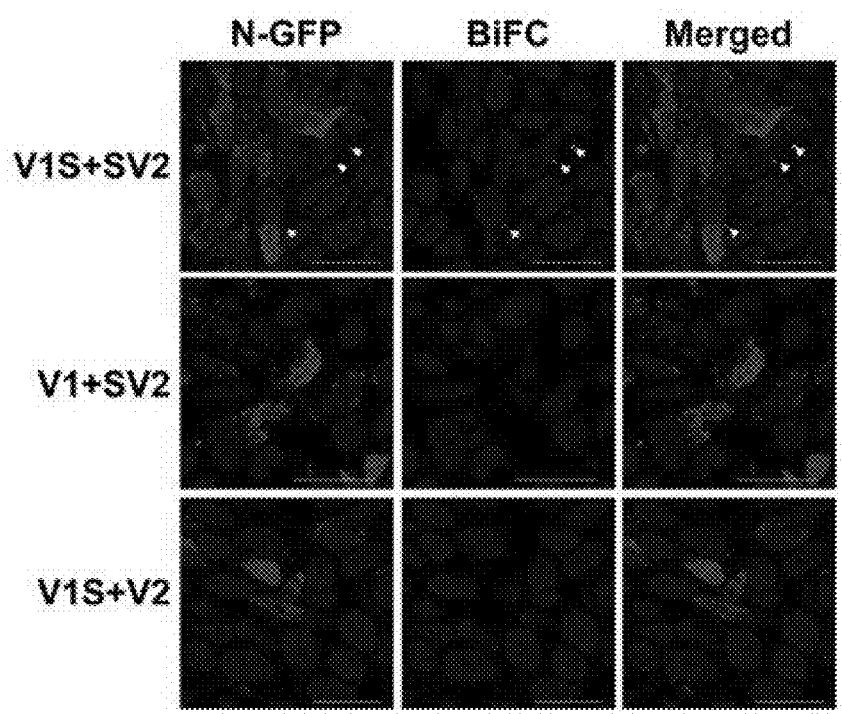
FIG. 8 illustrates α-synuclein-dependent cell-to-cell transmission in a dual-cell BiFC system.

Experimental Result 1-1. Seeding-Dependent Aggregate Transmission in the Novel Dual-Cell BiFC System In order to clarify the mechanism of aggregate spreading by direct observation of cell-to-cell transmission of α-synuclein aggregates, the present inventors developed an analysis based on BiFC. The present inventors produced two stable cell lines expressing α-synuclein fused to the N-terminus (V1S) or C-terminus (SV2) fragment of Venus, a variant of yellow fluorescence protein (FIG. 1a). The V1S and SV2 constructs were individually transfected into SH-SY5Y cells, and stable cell lines expressing similar levels of the two α-synuclein fusion proteins were selected (FIG. 1b). As anticipated, neither V1S-expressing cells nor SV2-expressing cells fluoresced in individual culture (FIGS. 1d and 1e). When the cell lines were co-cultured, however, fluorescence resulting from dimerization or oligomerization of the V1S and SV2 fusion proteins during cell-to-cell transfer of α-synuclein was visualized using BiFC (FIGS. 1a, 1d, and 1e). Neither the co-culture of cells expressing V1S and the C-terminal fragment (V2) of Venus nor those expressing SV2 and the N-terminal fragment (V1) of Venus produced BiFC frourescence (FIG. 8), validating the specificity of homotypic interaction between α-synuclein proteins. SinceV1S was secreted at a higher level than SV2 (FIG. 1c), transfer of α-synuclein during co-culture of the cell lines was assumed to primarily involve V1S.

Figure 1G:
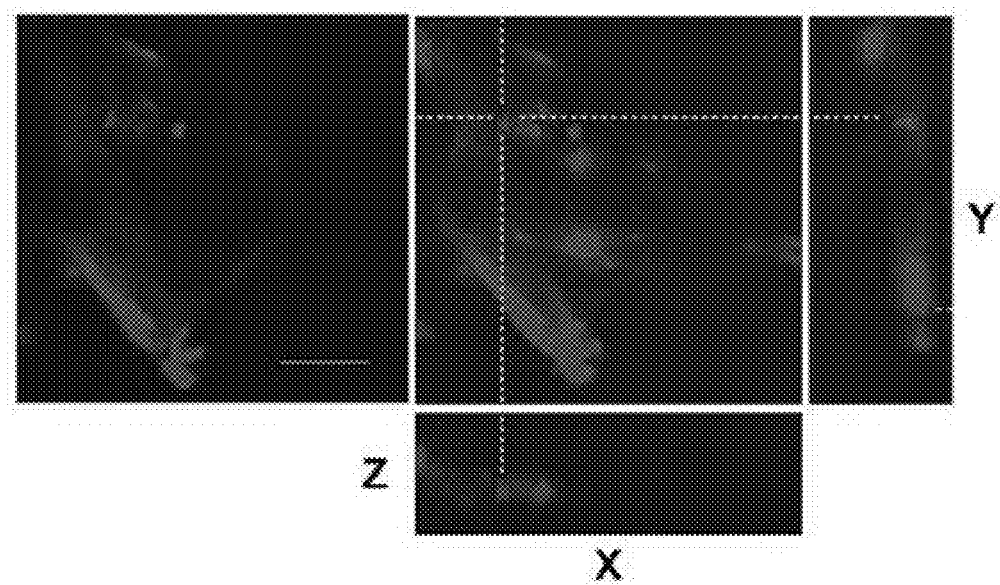

Immunoflourescence analysis showed that approximately 2-5% of cells contained small fluorescent inclusion bodies positive for α-synuclein and the N- and C-termini of Venus (FIGS. 1d and 1e), phospho-α-synuclein (Ser129), and ubiquitin (FIG. 10. These characteristics are similar to the Lewy bodies and pathogenic inclusions observed in transgenic models (Spillantini, M. G. et al. 1998 *Proc Natl Acad Sci USA* 95, 6469-6473). Three-dimensional reconstruction of z-stack images indicated that the fluorescent inclusions were intracellular structures (FIG. 1g). These results demonstrated the cell-to-cell transfer and co-aggregation of the transferred α-synuclein with resident α-synuclein.

Figure 2A:
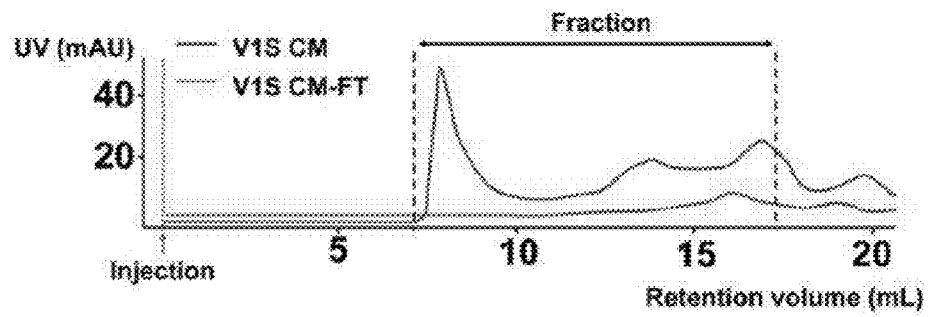
FIGS. 2a to 2e illustrate α-synuclein aggregates in V1S CM and their seeding effects.
Figure 2B:
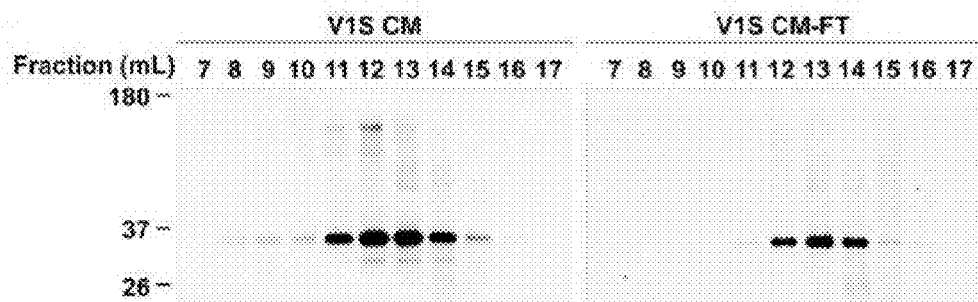
Figure 2C:
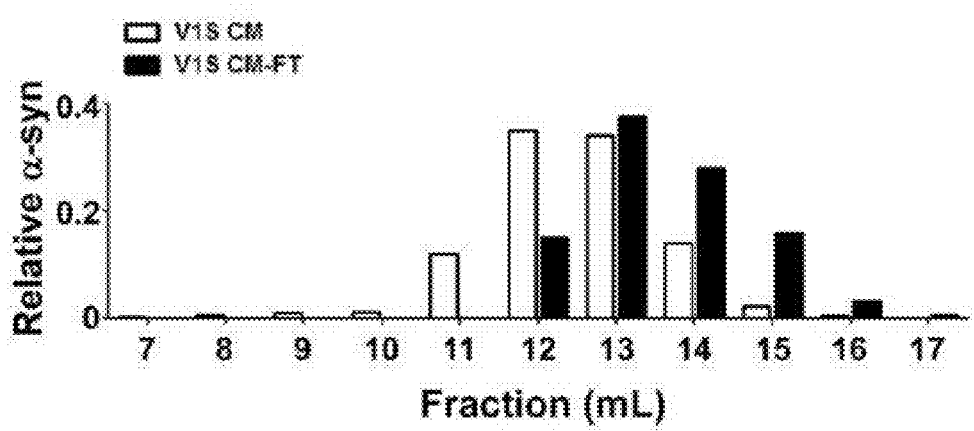
Figure 2D:
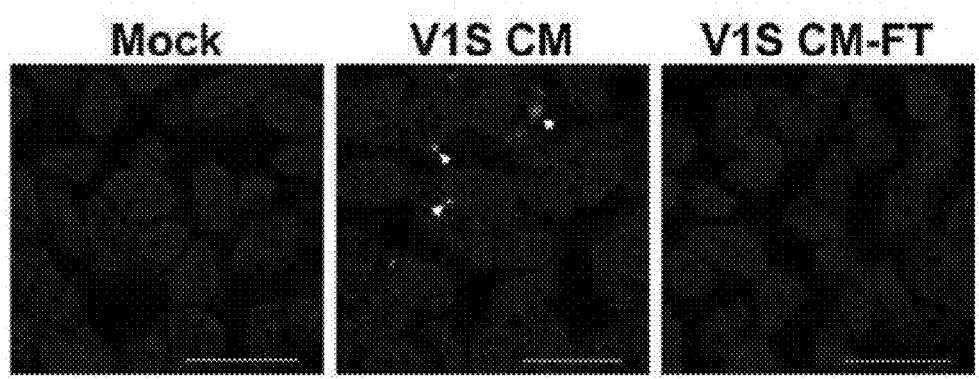
Figure 2E:
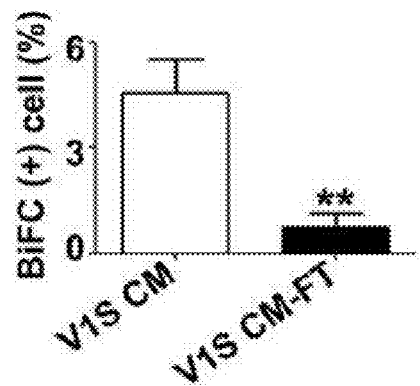

Assessed by western blot analysis, the majority of intracellular α-synuclein in V1S and SV2 cells was triton x-100 soluble and monomeric (FIG. 1b). However, the cell culture media contained the aggregates of α-synuclein (FIG. 1c), suggesting the aggregates were preferentially secreted from cells. To further validate the presence of aggregates in the culture media, size exclusion chromatography using the total culture medium (V1S CM) and the culture medium passed through a 100 kDa cutoff filter (V1S CM-FT) was performed (FIGS. 2a, 2b, and 2c). Histogram of V1S CM showed distribution of α-synuclein in a wide size ranges from monomer (13 mL) to void volume fractions (8 mL), while that of V1S CM-FT showed only the monomer (FIG. 2b and. 2c). This suggests that the V1S CM contained aggregated forms, and 100 kDa cutoff filtration effectively removed the aggregates, leaving only the monomers. To confirm the seeded aggregation in the recipient cells, SV2 cells were treated with either the total V1S CM or V1S CM-FT and BiFC-positive aggregates were analyzed. Administration of the total V1S CM resulted in BiFC-positive aggregates in SV2 cells, whereas removal of high-molecular weight aggregates from the V1S CM (V1S CM-FT) eliminated the "seeding" ability of the CM (FIGS. 2d and 2e). These data suggest that cells release aggregated α-synuclein, and the aggregated forms can seed the aggregation in the recipient cells in the dual cell-BiFC model of the present disclosure.

Figure 3A:
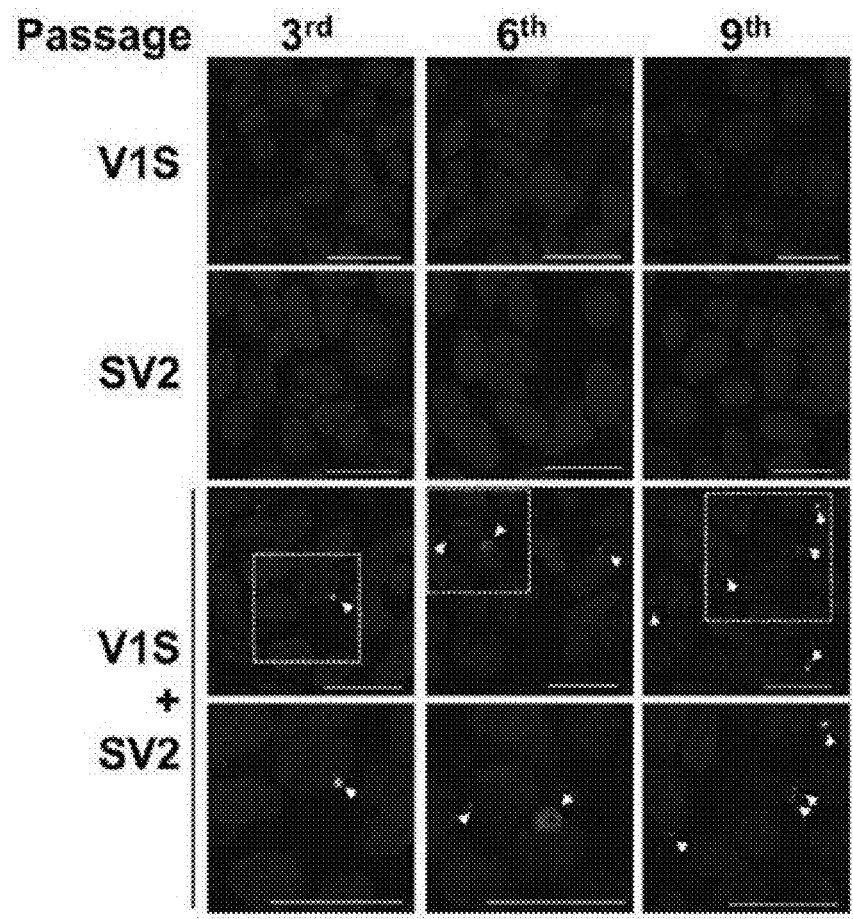
FIGS. 3a to 3k illustrate contiguous cell-to-cell transmission of α-synuclein aggregates.
Figure 3B:
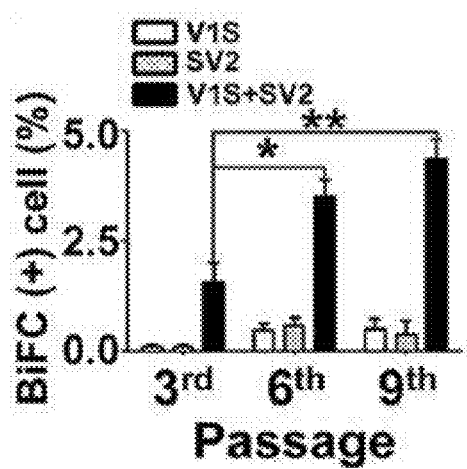
Figure 3C:
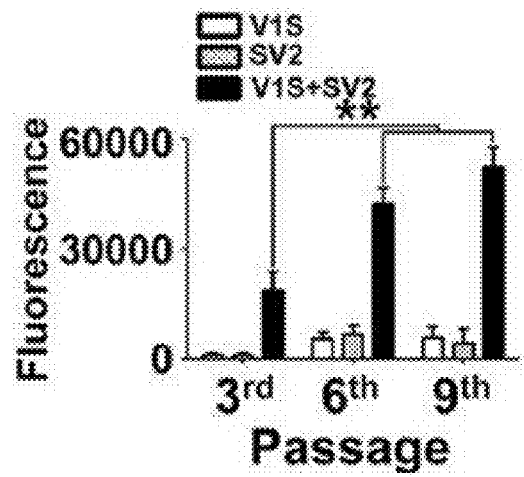
Figure 3D:
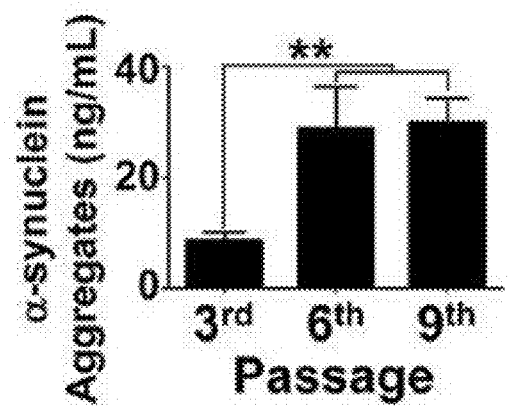

Experimental Result 1-2. Perpetual Spreading of α-Synuclein Aggregates Through Continuous Cell-to-Cell Transmission To explain pathological aggregate spreading within the central nervous system (CNS), cell-to-cell transmission should not be a single, discontinuous process. The secondary release of co-aggregated α-synuclein that is produced in the first round of transmission, is absolutely required for spreading of aggregate pathology. To address this problem, the present inventors used the dual-cell BiFC system. During continuous subculture of V1S and SV2-expressing cells, if transmission is a single, discontinuous event, the percentage of BiFC-positive cells decreases as passage number increased. Conversely, if the transmission is a continuous event, the percentage of BiFC-positive cells increases with passage number until reaching a steady state (FIG. 12). Co-culture of V1S and SV2 cells for several passages (cultured for 48 h for each passage) resulted in a continuous increase in the percentage of BiFC-positive cells (FIGS. 3a and 3b). Similarly, BiFC fluorescence in the culture media, representing the secondary secretion of co-aggregates of the "seed" and endogenous α-synuclein, also increased with increasing number of passages (FIG. 3c). This was confirmed by increased quantities of oligomers in the media (FIG. 3d). Also, it was confirmed that the ratio of BiFC-positive cells between V1S and SV2 cells does not change significantly during the successive subcultures (FIG. 13).

Figure 3E:
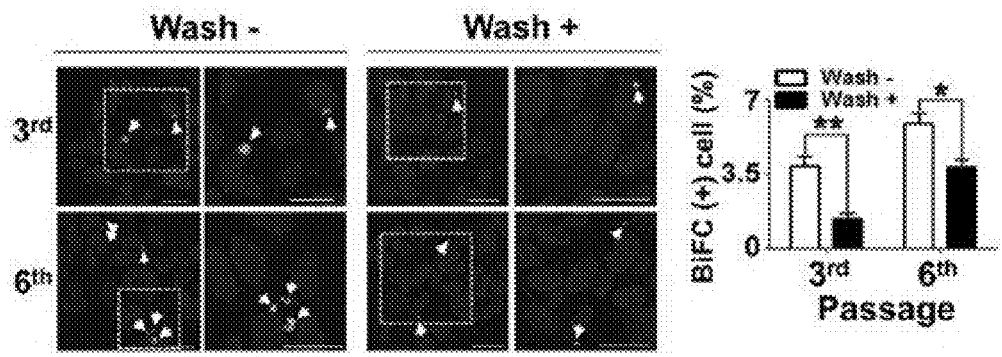
Figure 3F:
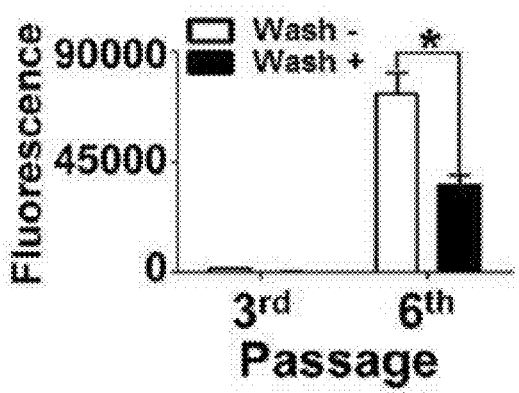
Figure 3G:
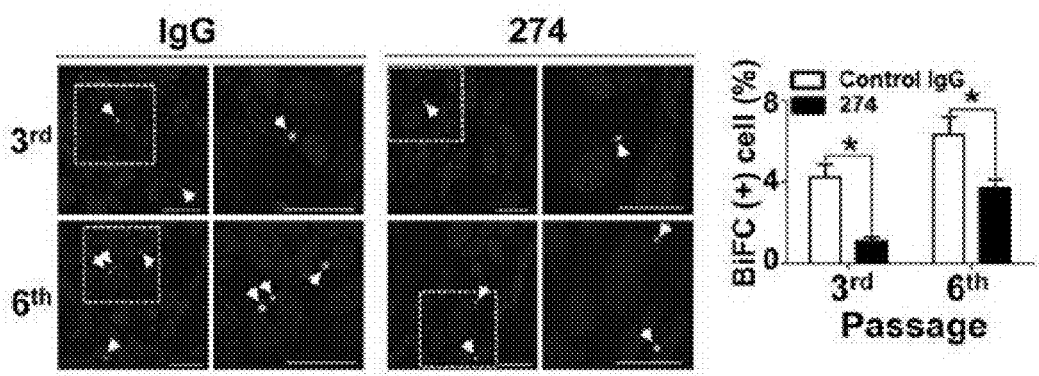
Figure 3H:
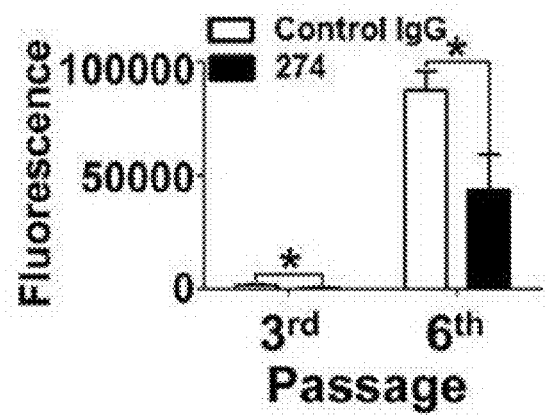
Figure 3I:
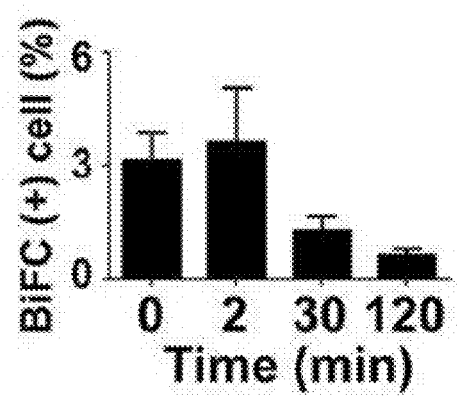
Figure 3J:
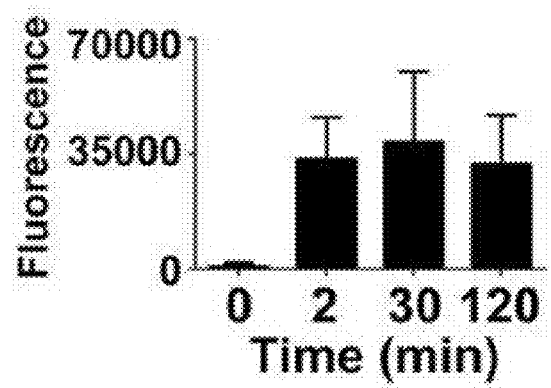
Figure 3K:
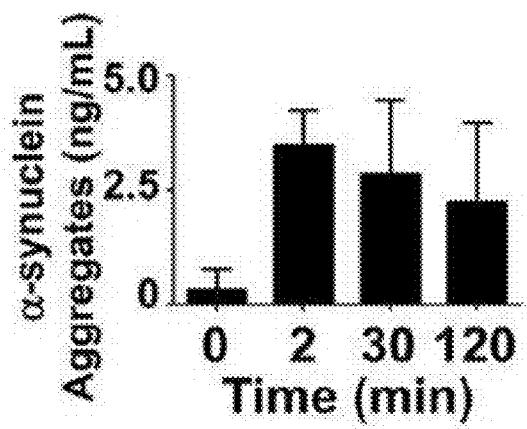

To demonstrate the transfer of seeds through the fluid phase, media washing and antibody blocking experiments were next performed. During the co-culture of V1S and SV2 cells, culture media were removed and replaced with the fresh media. When BiFC fluorescence was analyzed one day after the media replacement, both intracellular and media BiFC signals were decreased (FIGS. 3e and 3f), consistent with fluid phase transfer of the seed. Next, Ab274, an α-synuclein-specific antibody, was added to the co-culture one day prior to the BiFC analysis, in order to hijack the secreted α-synuclein, thereby blocking the transfer of this protein. This antibody treatment suppressed BiFC signals in both the cytoplasm and the media (FIGS. 3g and 3h). To assess the temporal changes of the seeding and secondary secretion, a pulse-chase experiment was performed, in which conditioned medium (CM) obtained from the V1S culture was added to the SV2 cells. After a steady state was reached, the V1S CM was washed out and the BiFC signal was analyzed in cells and the medium at selected time points. Co-aggregates of V1S and SV2 proteins disappeared rapidly from the cytoplasm after medium washing, whereas the secreted BiFC signal increased reciprocally (FIGS. 3i and 3j). Oligomer-specific ELISA confirmed the increase in the level of α-synuclein oligomers in the medium (FIG. 3k). Together, these results suggest that α-synuclein aggregates are transferred from cell to cell contiguously through a cycle of sequential events, involving inter-cellular aggregate transfer, seeding of the aggregation of endogenous α-synuclein, and secondary secretion of the seeded aggregates (FIG. 14).

Experimental Result 1-3. GBA1 Deficiency LED to Lysosomal Dysfunction

Figure 4A:
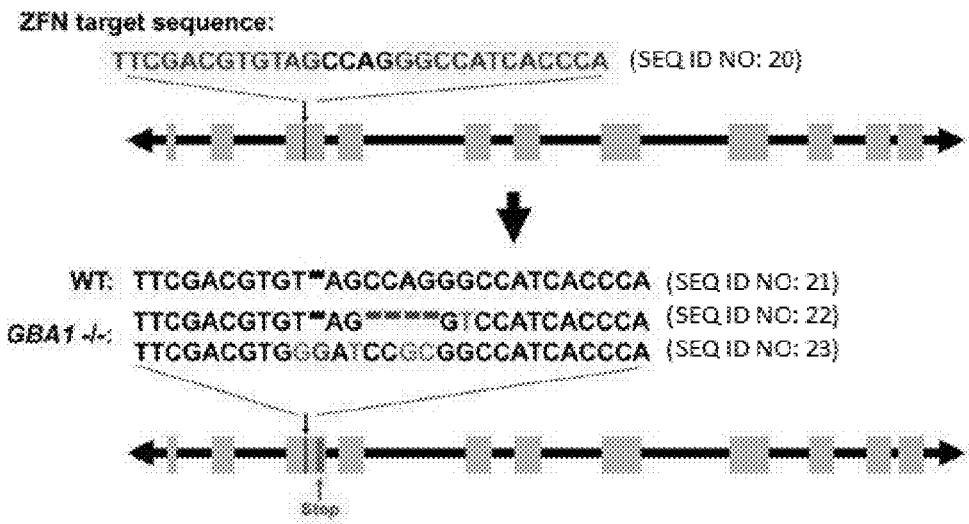
FIGS. 4a to 4e illustrate GBA1 knockout in SV2 cells zinc-finger nucleases (ZFN).
Figure 4B:
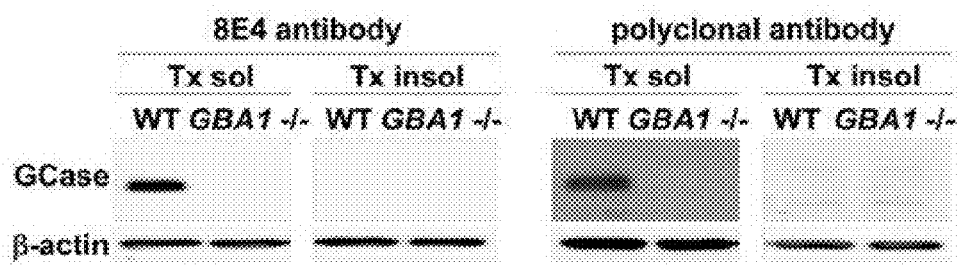
Figure 4C:
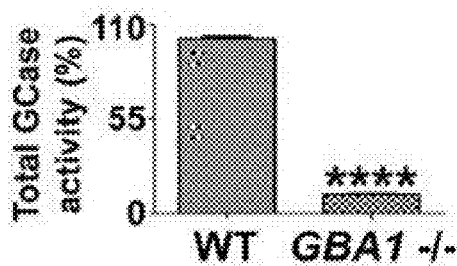
Figure 4D:
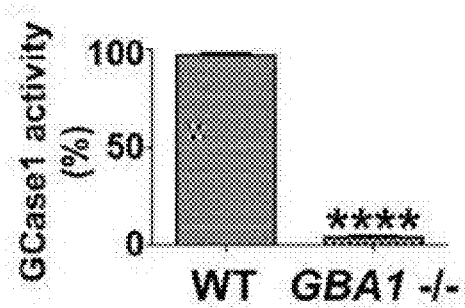
Figure 4E:
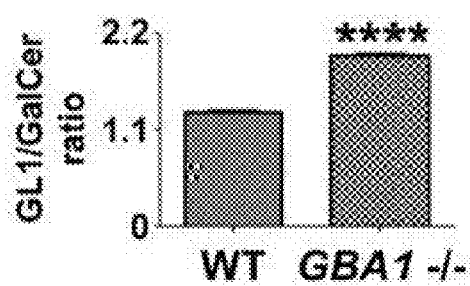

To assess the role of GBA1, a strong genetic risk factor for PD, in α-synuclein aggregate transmission, a zinc finger nuclease (ZFN)-based method was used to establish an SV2 cell line, SV2GBA1−/−, containing nonsense mutations in both alleles of the GBA1 gene (FIG. 4a and FIG. 15). This cell line fails to express GCase 1 (FIG. 4b), resulting in greatly reduced total GCase activity (FIG. 4c). GCase 2 activity was much lower than the GCase 1 activity, and did not change as a result of GBA1 gene mutation (FIG. 4d). As a consequence of depletion of GCase1, glucosylceramide, a substrate of the enzyme, accumulated in SV2GBA1−/− cells (FIG. 4e).

Figure 5A:
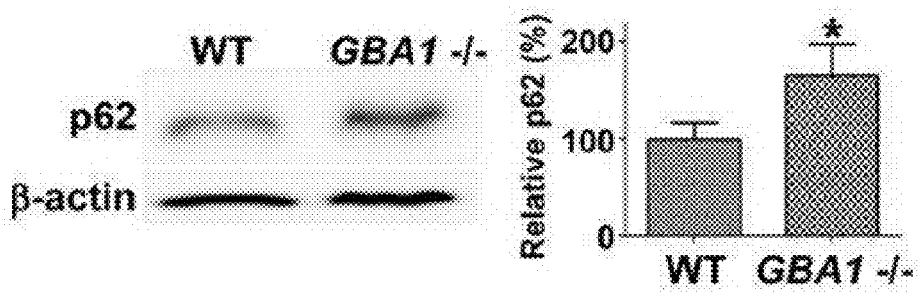
FIGS. 5a to 5e show that GBA1 deficiency causes lysosomal dysfunction.
Figure 5B:
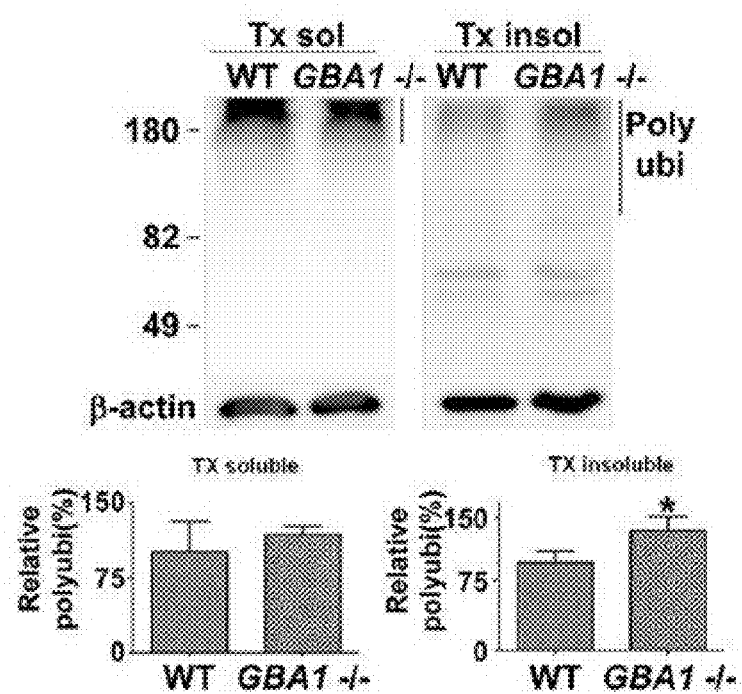
Figure 5C:
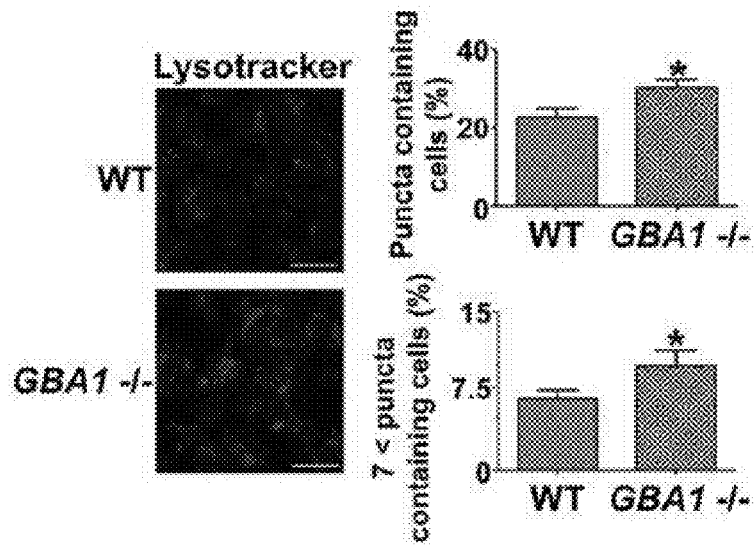
Figure 5D:
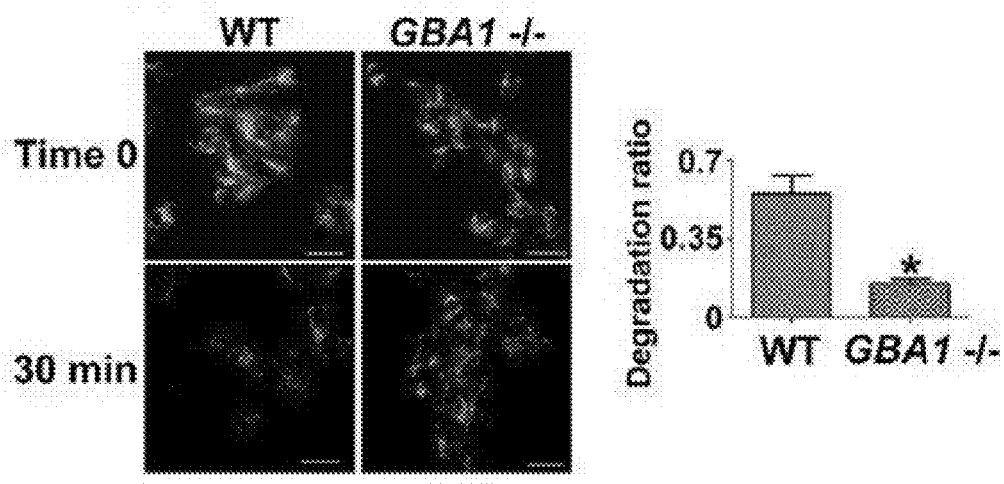
Figure 5E:
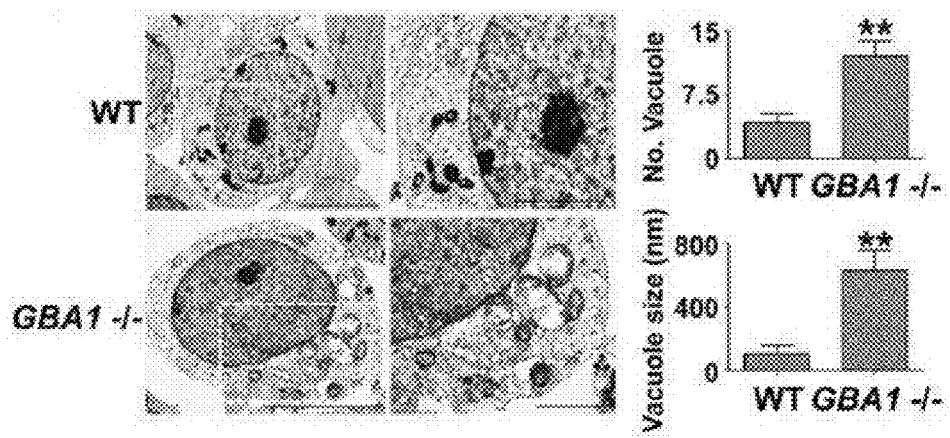

SV2GBA1−/− cells were characterized by accumulation of lysosomal substrates, such as p62 and polyubiquitinated proteins (FIGS. 5a and 5b), suggesting lysosomal dysfunction. Consistent with the lysosomal abnormalities, these cells have increased Lysotracker-positive structures (FIG. 5c), reduced degradation of ectopically introduced dextran (FIG. 5d), and exhibited accumulation of vacuolar structures in the cytoplasm (FIG. 5e), all of which clearly demonstrated lysosomal impairment. In addition, the present inventors confirmed that GBA1 gene deletion caused lysosomal dysfunction in parental SH-SY5Y cells.

Figure 6A:
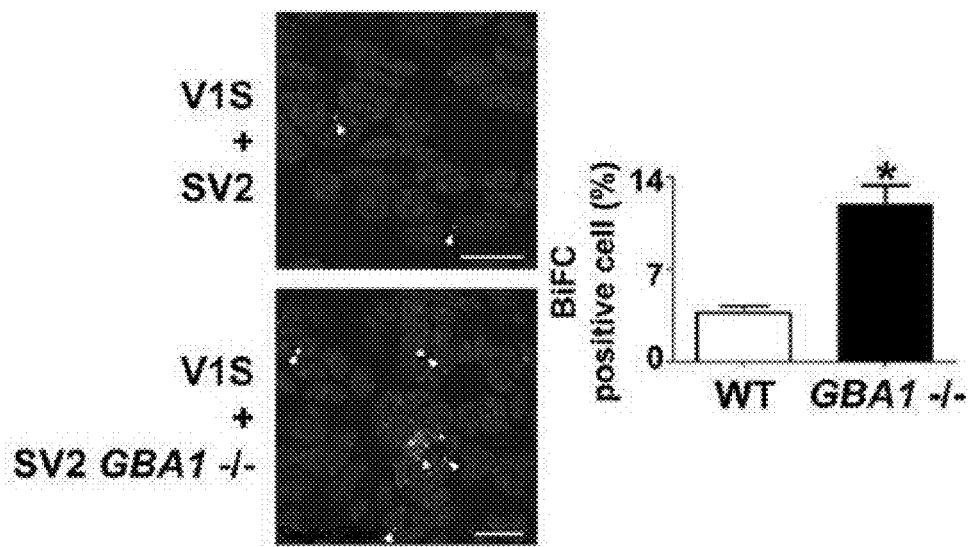
FIGS. 6a to 6g show that GBA1 deficiency leads to an increase in contiguous cell-to-cell transmission of α-synuclein aggregates. Scale bars: 20 μm.
Figure 6B:
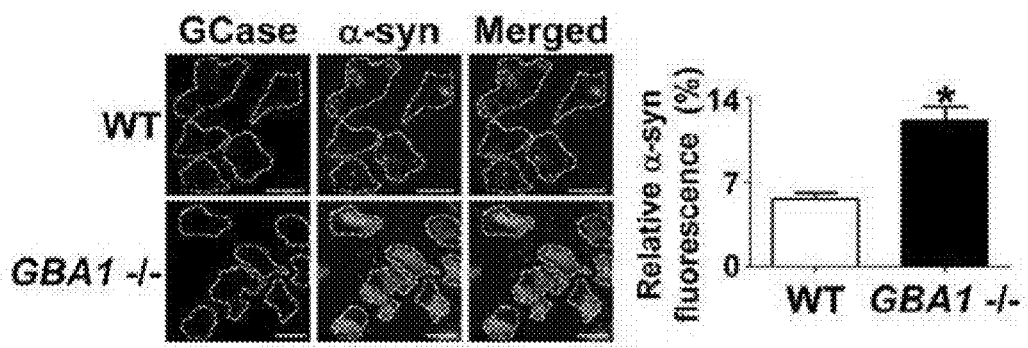
Figure 6C:
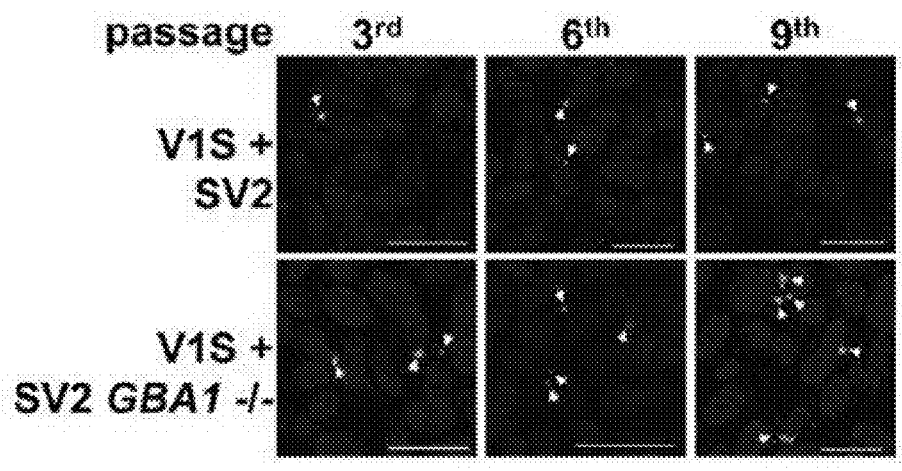
Figure 6D:
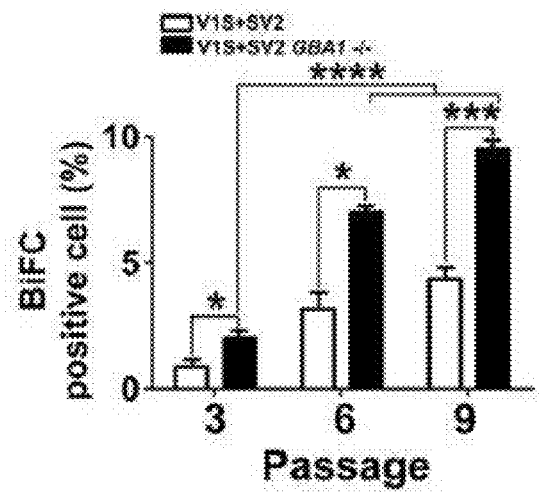
Figure 6E:
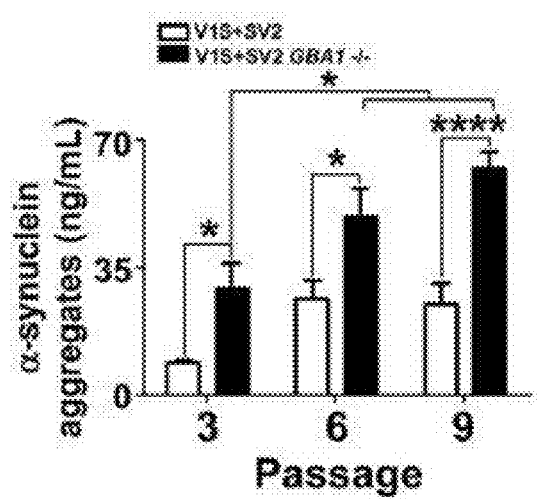
Figure 6F:
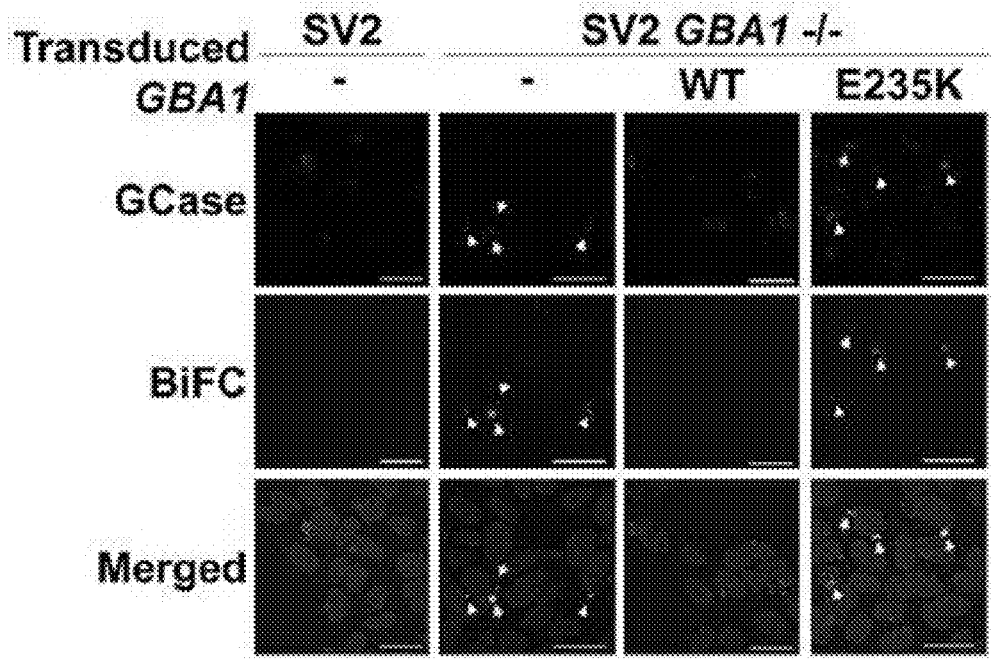
Figure 6G:
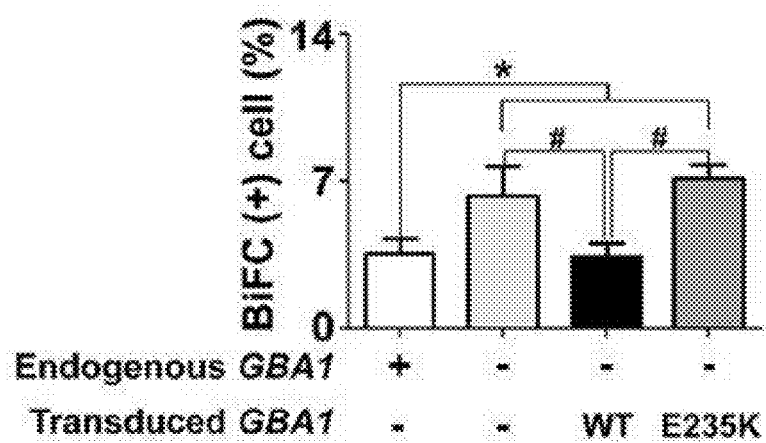

Experimental Result 1-4. GBA1 Deficiency Potentiated Continuous Transmission of α-Synuclein Aggregates Next, whether GBA1 deletion affects cell-to-cell transmission of α-synuclein was examined. When V1S cells were co-cultured with SV2GBA1-/- cells, the percentage of BiFC-positive cells was significantly increased compared with V1S/SV2 co-cultures (FIG. 6a). The present inventors interpret this to reflect the reduced capacity of SV2GBA1-/- cells to clear internalized aggregates due to lysosomal impairment (FIG. 6b). Then, the effects of GBA1 gene deletion were examined on contiguous transmission. Co-culturing of V1S and SV2GBA1-/- cells resulted in a significant increase in the number of BiFC-positive cells relative to V1S/SV2 co-cultures during several passages (FIGS. 6c and 6d). Similarly, levels of α-synuclein oligomers were higher in the media of V1S/SV2GBA1-/--co-cultures than in V1S/SV2 co-cultures (FIG. 6e and FIG. 16). Again, the ratio of BiFC-positive cells between V1S and SV2GBA1-/- did not change significantly during the sub-culture (FIG. 17). Further indicating the role of GCase activity in this process, this phenomenon was reversed by AAV vector-mediated ectopic expression of the wild type GBA1 gene, but not in that encoding the activity-deficient E235K mutant (FIGS. 6f and 6g).

To ensure that the results of the GBA1 gene deletion did not represent "off-target" effects, RNA interference (RNAi) experiments using AAV vectors were next performed. Reduction of GCase 1 expression using two different shR-NAs was confirmed with western analysis and activity analysis (FIG. 18). Knockdown of GCase 1 production resulted in a consistent increase in cell-to-cell transfer of α-synuclein. This effect of GCase 1 knockdown was reversed by recovery of GCase 1 production, hence the recovered activity, from ectopic expression of the wild type GBA1 gene (FIG. 19). Collectively, these results show that GBA1 depletion promoted perpetual transmission of α-synuclein aggregates and that ectopic expression of wild type GBA1 reversed this effect, suggesting that loss of GBA1 function increases α-synuclein aggregate spreading.

Figure 7A:
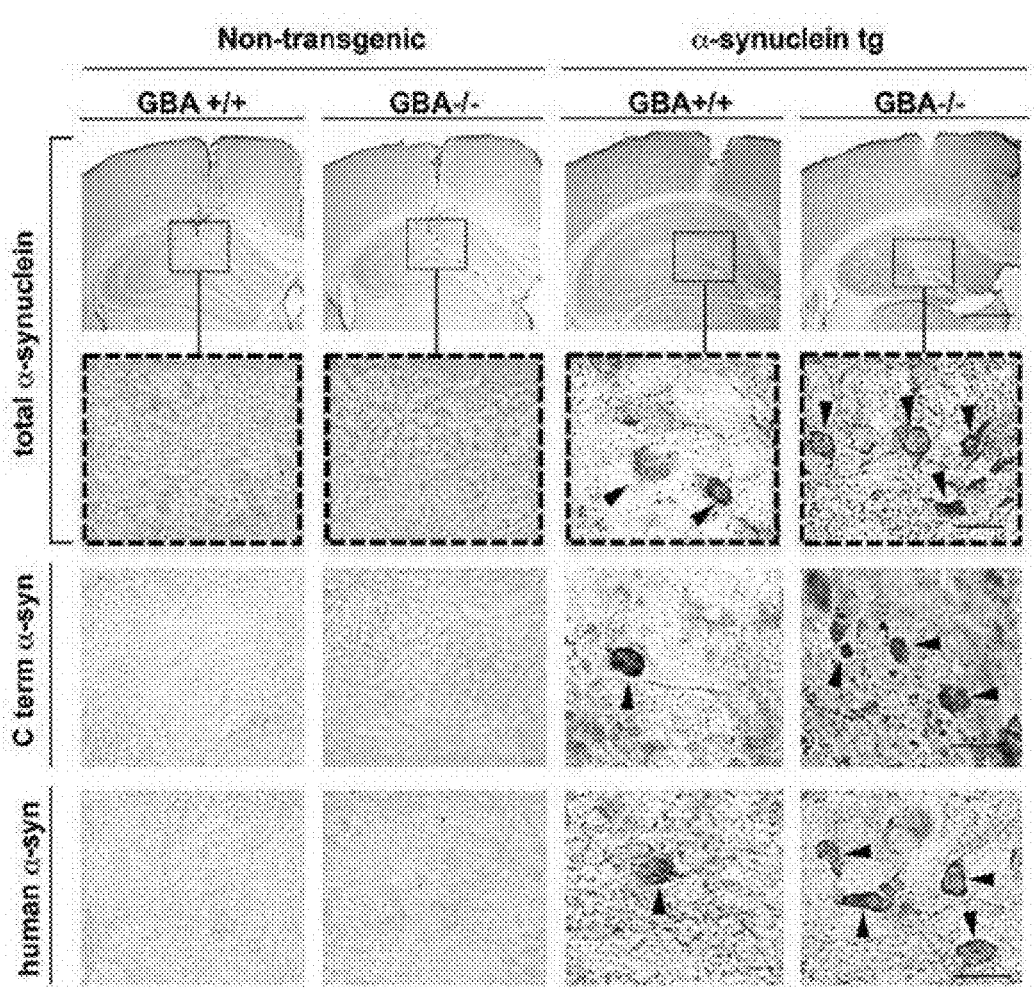
FIGS. 7a to 7g show that GBA1 deficiency increases the spreading of α-synuclein pathology in vivo.
Figure 7B:
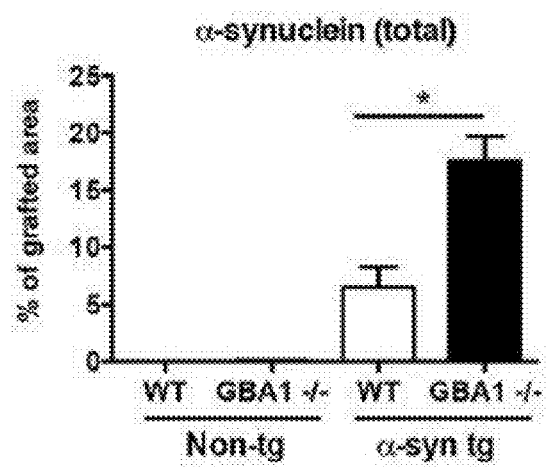
Figure 7C:
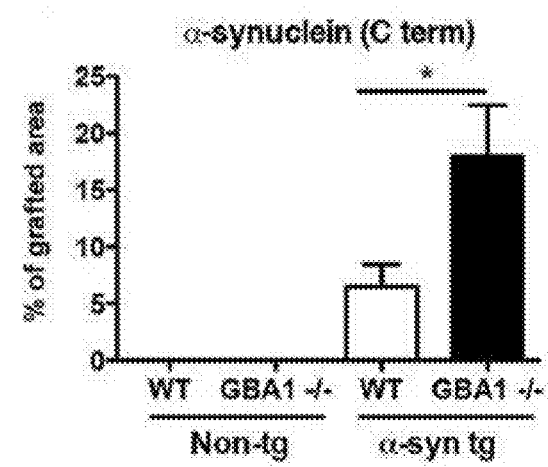
Figure 7D:
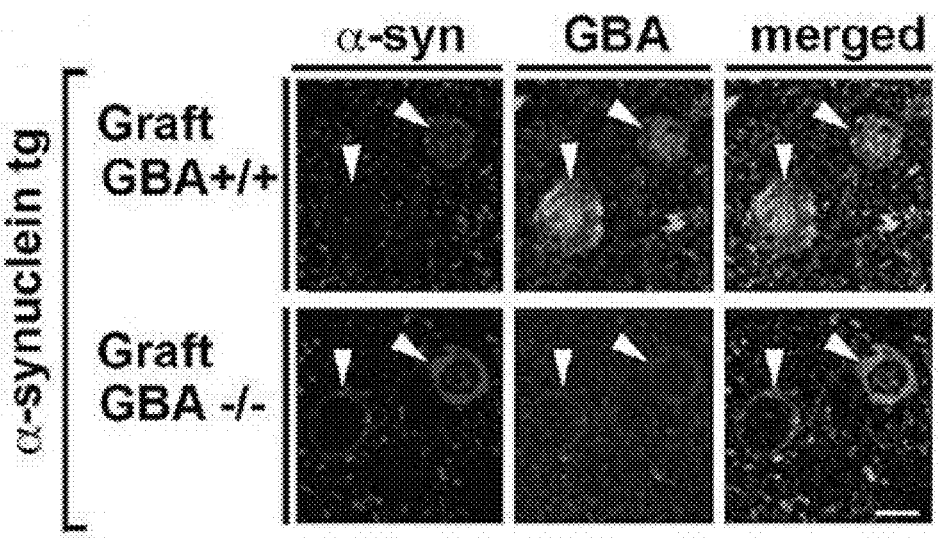
Figure 7E:
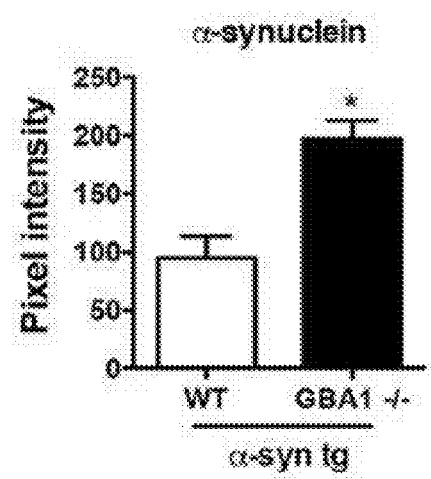
Figure 7F:
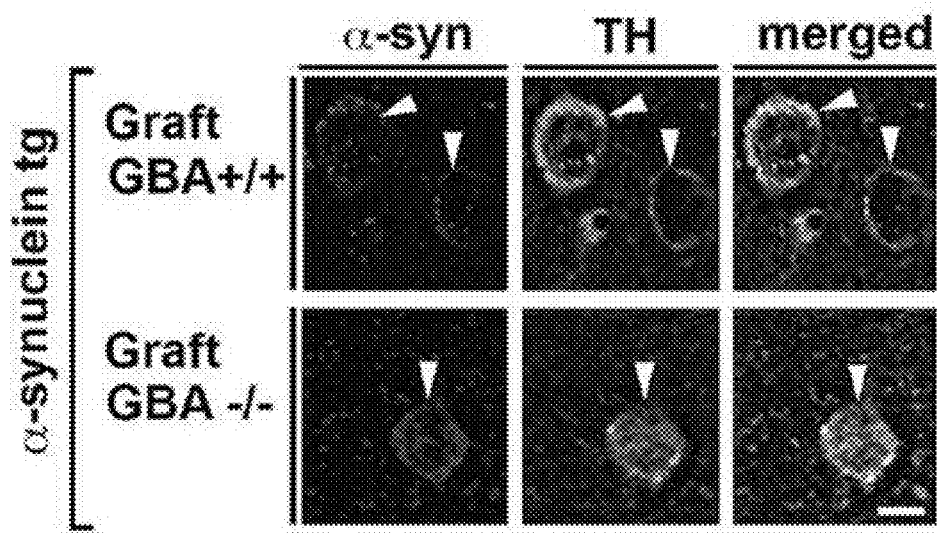
Figure 7G:
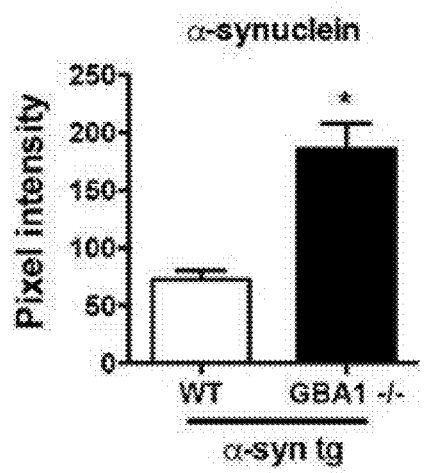

In the previous study, it was found that transgenic human α-synuclein was transferred from host cells to engrafted cells (Desplats, P. et al. 2009 Proc Natl Acad Sci USA 106, 13010-13015). To validate the role of GBA1 in vivo, a transplantation experiment was performed in which normal SH-SY5Y cells and GBA1-/- (SH-GBA1-/-) cells were transplanted into the hippocampus of transgenic mice expressing human α-synuclein, and transfer of α-synuclein from host cells to the grafted cells was analyzed. The grafted SH-SY5Y cells do not overexpress α-synuclein, only expressing small amount of endogenous α-synuclein, which hardly shows up in regular immunological detection protocols (FIGS. 7a, 7b, and 7c). The present inventors found that host-derived α-synuclein was accumulated at a higher rate in SH-GBA1-/- cells than in normal SH-SY5Y cells (FIGS. 7a, 7b, and 7c). Moreover, co-immunofluorescence analysis showed that SH-GBA1-/- cells accumulated host-derived α-synuclein at higher levels than normal SH-SY5Y cells (FIGS. 7d and 7e). Although SH-SY5Y cells express low levels of endogenous α-synuclein, the present inventors failed to detect expression of endogenous α-synuclein in engrafted SH-SY5Y cells (FIGS. 7a, 7b, and 7c). SH-SY5Y cells are human neuroblastoma cells that produce catecholamines, including dopamine. To ensure that the analysis of the present disclosure was specific for engrafted cells, immunostaining for tyrosine hydroxylase (TH) was performed, and it was found that levels of host-derived α-synuclein were higher in TH-positive engrafted SH-SY5Y GBA1-/- cells than in TH-positive engrafted SH-SY5Y cells (FIGS. 7f and 7g). Although there are TH-positive fibers in the hippocampus, there are no TH-positive cells. Thus, TH-positive cells in the hippocampus represent the grafted cells. The present inventors also performed a control experiment where differentiated SH-SY5Y cells were tagged with the enhanced green fluorescence protein (eGFP) via lentiviral infection and co-labeled for TH. The present inventors found that in vitro approximately 95% of the eGFP-positive cells were TH-positive. Likewise, about 80% of the grafted SH-SY5Y-eGFP cells in the mouse hippocampus (n=5) were TH-positive (FIG. 20).

EXAMPLE 2

Preparation of C. elegans Model and Measurement of Cell-to-Cell Transmission of α-Synuclein Using the Same Experimental Materials and Processes Example 2-1. Strains and Culturing All strains were handled using standard procedures, on nematode growth medium (NGM) plates containing a lawn of Escherischia coli (E. coli) strain OP50 at 20° C. (Brenner, S. 1974. The genetics of Caenorhabditis elegans. Genetics 77, 71-94). Wild-type Bristol N2 and the mutant strains unc-119(ed3), dyn-1(ky51), and asp-4(ok2693) were obtained from the Caenorhabditis Genetics Center (CGC, University of Minnesota, St. Paul, Minn.). The mutant strain asp-1(tm666) was provided by C. elegans National BioResource Project (NBRP, Tokyo Women's Medical University School of Medicine, Tokyo, Japan). The mutant strains daf-2(e1370) and daf-16(mu86) were provided by Professor Kyuhyung Kim (DGIST, Daegu, Korea).

Example 2-2. Plasmids Construction for C. elegans

V1S and SV2 template plasmids were provided by Dr. Pamela McLean (Massachusetts General Hospital, Boston, USA).

1) Pmyo-2::EGFP

The myo-2 promoter (Pmyo-2) was PCR-amplified from genomic DNA obtained from wildtype N2 worms. A sense primer containing a HindIII site, 5'-GACAAGCT-TGGGGTTTTGTGCTGTGGACGTT-3' (SEQ ID NO: 6) and an anti-sense primer containing a BamHI site, 5'-GACGGATCCTTCTGTGTCTGACGATCGAGG-3' (SEQ ID NO: 7) were used. Pmyo-2::EGFP was prepared by inserting the PCR product into the HindIII and BamHI sites of the pFX_EGFPT vector (Gengyo-Ando et al., 2006).

2) Pmyo-2::α-synuclein (Myc)

A sense primer containing a SalI site, 5'-AGCGTC-GACGCCACCATGGATGTATTCATGAAAGGAC-3' (SEQ ID NO: 8) and an anti-sense primer containing myc tag sequence and BglII site, 5'-AGCAGATCTCTACA-GATCCTCTTCAGAGATGAGTTTCTGCTCGGCTTCA-GGTT CGTAGTCTTG-3' (SEQ ID NO: 9) were used to amplify the myc tagged human α-synuclein obtained from pcDNA3.1 MycHis α-synuclein vector (ref). The EGFP fragment of Pmyo-2::EGFP was replaced by the PCR-amplified myc tagged human α-synuclein fragment to prepare Pmyo-2:: α-synuclein (Myc).

3) Pmyo-2::V1S

A sense primer containing a SalI site, 5'-AGCGTC-GACGCCACCATGGTGAGCAAGGCCGAGG-3' (SEQ ID NO: 10) and an anti-sense primer containing a BglII site, 5'-AGCAGATCTTTAGGCTTCAGGTTCGTAGTC-3' (SEQ ID NO: 11) were used to amplify V1S. In addition, the EGFP fragment of Pmyo-2::EGFP was replaced by the PCR amplified V1S fragment to prepare Pmyo-2::V1S.

4) Pflp-21::SV2

The EGFP fragment of pFX_EGFPT was replaced by the PCR-amplified SV2 fragment to make an SV2 vector. The sense primer containing a SpeI site, 5'-AGCACTAGTGC-CACCATGGATGTATTCATGAAAGG-3' (SEQ ID NO: 12) and an anti-sense primer containing a BglII site, 5'-AGCAGATCTTACTTGTACAGCTCGTCCATGCCG-3' (SEQ ID NO: 13) were used. The flp-21 promoter (Pflp-21) was PCR-amplified from N2 genomic DNA and subcloned into KpnI and SalI sites of the SV2 vector to prepare Pflp-21::SV2. A sense primer containing a KpnI site, 5'-AGCGGTACCAACTAGGTCCAGTGACCGAAAG-3' (SEQ ID NO: 14) and an anti-sense primer containing a SalI site, 5'-AGCGTCGACGCCACCATGGATGTATTCAT-GAAAGGAC-3' (SEQ ID NO: 15) were used to amplify the flp-21 promoter.

5) Pflp-21::SV2-ICR-DsRed

To prepare an SV2 vector co-expressing DsRed as a pharyngeal neuronal marker, Pflp-21 was subcloned into the KpnI and SalI sites of the pFX_DsRedxT vector (Gengyo-Ando, K., et al., 2006. An efficient transgenic system by TA cloning vectors and RNAi for C. elegans. Biochem. Biophys. Res. Commun 349, 1345-1350) and named Pflp-21::DsRed. Co-expression of SV2 and DsRed under the flp-21 promoter was achieved by placing an intercistronic region (ICR) between SV2 and DsRed, which was PCR-amplified from N2 (Lee, L. W., et al. 2010a. Vectors for co-expression of two genes in Caenorhabditis elegans. Gene 455, 16-21). The SV2 fragment was fused with the ICR region by fusion PCR (Hobert, O. 2002. PCR fusion-based approach to create reporter gene constructs for expression analysis in transgenic C. elegans. BioTechniques 32, 728-730) and subcloned into the Pflp-21::DsRed to prepare Pflp-21::SV2-ICR-DsRed. A sense primer containing a SalI site, 5'-AGCGTCGACGCCACCATGGATGTATTCAT-GAAAGGAC-3' (SEQ ID NO: 16) and an anti-sense primer containing an overlapping region with an ICR, 5'-CGAT-CATTTTGGAGATTACTTGTACAGCTTGTCC-3' (SEQ ID NO: 17) was used in the PCR reaction for SV2. The ICR region was amplified with a sense primer containing an overlapping region with SV2, 5'-GGACGAGCTGTA-CAAGTAATCTCCAAAATCATCG-3' (SEQ ID NO: 18) and an anti-sense primer containing a SpeI site 5'-AG-CACTAGTTACCCTGTAATAATATATTAAAC-3' (SEQ ID NO: 19).

Example 2-3. Preparation of BiFC Transgenic Worms

Pmyo-2::V1S and Pflp-21::SV2-ICR-DsRed plasmids were co-injected into the gonads of late L4-stage N2 worms with a selection marker, pRF4 which expresses a mutant collagen gene, rol-6(su1006) (Mello, C. C., et al. 1991. Efficient gene transfer in C. elegans: extrachromosomal maintenance and integration of transforming sequences. The EMBO J 10, 3959-3970), to prepare double transgenic line expressing the BiFC pair. As a negative control for BiFC, Pmyo-2::V1S alone was injected into N2 worms with pRF4, and Pflp-21::SV2-ICR-DsRed alone was injected into unc-119(ed3) mutant worms with a selection marker, pCFJ151, which expresses unc-119(+) gene (Frokjaer-Jensen, et al. 2008. Single-copy insertion of transgenes in Caenorhabditis elegans. Nat. Genet 40, 1375-1383). The plasmid Pmyo-2::V1 was prepared to express the BiFC partial sequence only by introducing the stop codon right before the α-synuclein coding sequence in Pmyo-2::V1S and was prepared using a QuickChange Site-Directed Mutagenesis Kit (Stratagene, La Jolla, Calif.). Pmyo-2::V1 and Pflp-21::SV2-ICR-DsRed plasmids were then co-injected into N2 with pRF4. In addition, Pflp-21::DsRed was injected into N2 with pRF4 as a control for the effects of general protein overexpression in neurons. For chromosomal integration of the introduced plasmids, injected lines were exposed to UV irradiation. After UV irradiation, each integrated line was out-crossed 4 times with N2. Double transgenic lines carrying Pmyo-2::V1S and Pflp-21::SV2-ICR-DsRed were prepared by mating an integrated Pmyo-2::V1S line with an integrated Pflp-21::SV2-ICR-DsRed line. All of these transgenic worms showed a roller phenotype and expression of DsRed fluorescence in the pharyngeal neurons.

Example 2-4. Generation of Untagged α-Synuclein Models

Pmyo-2:: α-synuclein and Pflp-21:: α-synuclein plasmids were prepared to express α-synuclein only by introducing stop codon right after the α-synuclein coding sequence by using a QuickChange Site-Directed Mutagenesis Kit. As a negative control, Pmyo-2:: α-synuclein alone was injected into N2 worms with pRF4. Pmyo-2:: α-synuclein and Pflp-21:: α-synuclein plasmids were co-injected into the gonads of late L4-stage N2 worms with pRF4. All of these worms showed a roller phenotype and three representative lines of each genotype were used for experiments.

Example 2-5. Preparation of Aging-Related BiFC Models

Pmyo-2::V1S and Pflp-21::SV2-ICR-DsRed plasmids were co-injected into the gonads of late L4-stage daf-2 (e1370) and daf-16(mu86) mutant worms with the pRF4. As a control for aging related BiFC models, Pmyo-2::V1S or Pflp-21::SV2-ICR-DsRed alone was injected into the gonads of late L4-stage of N2 and daf-16(mu86) mutant worms with pRF4. After several transgenic lines containing the introduced plasmids were obtained, three representative lines in each mutant background were used for experiments.

Example 2-6. Preparation of Hlh-30 Transgenic Lines

A plasmid expressing hlh-30p::hlh-30::gfp was obtained from Dr. Malene Hansen (Sanford-Burnham Medical Research Institute, CA, USA). The plasmid hlh-30p::hlh-30 was designed to introduce codon before the GFP coding sequence using a QuickChange Site-Directed Mutagenesis Kit to inhibit GFP expression. As a control, each Pmyo-2::V1S or Pflp 21::SV2-ICR-DsRed and hlh-30p::hlh-30 were co-injected into the gonads of late L4-stage N2 worm with pRF4. The plasmids expressing Pmyo-2::V1S, Pflp-21::SV2-ICR-DsRed and hlh-30p::hlh-30 were co-injected into the gonads of late L4-stage daf-16(mu86) mutant worms with pRF4. To analyze lysosomal dysfunction, asp-4 (ok2693) and asp-1(tm666) mutant worms, in which the lysosomal enzyme cathepsin gene is inactivated, were used. Pmyo-2::V1S and Pflp-21::SV2-ICR-DsRed plasmids were co-injected into the gonads of late L4-stage mutant worms with pRF4. After transgenic lines containing the introduced plasmids were obtained, three representative lines of each genotype were used for experiments

Example 2-7. Immunofluorescence Microscopy

For immunofluorescence staining of worms, wild-type N2 and transgenic worms were collected, washed with M9 buffer (22 mM KH2PO4, 22 mM Na2HPO4, 85 mM NaCl, 1 mM MgSO4), and then pre-fixed with 4% paraformaldehyde in MRWB (80 mM KCl, 20 mM NaCl, 10 mM EGTA, 5 mM spermidine, 50% methanol). To reduce cuticle layer rigidity for penetrance, the worms were subjected to several freeze/thaw cycles using liquid nitrogen, and incubated with agitation at 4° C. for 2 h. Because reduction and oxidation steps increase the permeability of the worm, the worms were washed with Tris-Triton buffer [100 mM Tris-HCl (pH 7.4), 1% Triton X-100, 1 mM EDTA], and incubated with 1% β-mercaptoethanol in Tris-Triton buffer at room temperature (RT) for 2 h. Subsequently, the worms were incubated in collagenase solution[100 unit of collagenase type IV in 100 mM Tris-HCl (pH 7.4), 1 mM CaCl2, 0.1% Triton X-100] with rotation at RT for 4 h. Then the worms were incubated in Tris-Triton buffer supplemented with 0.3% $H_2O_2$ at RT for 15 min. After incubation in blocking buffer (1% BSA, 0.5% Triton X-100, 1 mM EDTA in PBST), the worms were incubated with monoclonal antibody, 274 mAb (Lee et al., 2011) overnight at 4° C. in primary antibody solution (1% BSA, 0.5% Triton X-100, 1 mM EDTA in PBS). The following day, the worms were washed with blocking buffer and incubated with rhodamine red X-conjugated goat anti-mouse IgG (Jackson Immunoresearch Laboratories, West grove, PA, USA) for 2 h. The worms were then washed with blocking buffer and fixed in Antifade reagent (Invitrogen, Eugene, Oreg., USA). Samples were analyzed using Olympus FV1000 confocal laser scanning microscopy (Olympus, Tokyo, Japan).

Example 2-8. Single-Worm PCR

A gravid single worm from each line was lysed in lysis buffer (50 mM KCl, 10 mM ris-HCl, pH 8.3, 2.5 mM MgCl2, 0.45% NP-40, 0.45% Tween 20) with 0.1 mg/ml proteinase K (Sigma). The single worm in the buffer was subjected to several freeze-thaw cycles using liquid nitrogen, incubated at 65° C. for 1 h to release genomic DNA, and then heated at 95° C. for 15 min to inactivate proteinase K. Single-worm PCR analysis was performed using ExTaq™ polymerase (Takara Shuzo Co. Ltd, Shiga, Japan).

Example 2-9. PCR-RFLP Genotyping

Gravid 5 worms from each line were lysed in the lysis buffer with 0.1 mg/ml proteinase K. Worms in the buffer were subjected to several freeze-thaw cycles using liquid nitrogen, incubated at 65° C. for 1 h to release genomic DNA, and then heated at 95° C. for 15 min to inactivate proteinase K. After performing PCR, the PCR products were digested with NcoI enzyme (New England Biolabs Inc., MA, USA), at 37° C. overnight and electrophoresed to detect RFLP.

Example 2-10. Heat-Shock Treatment of Dyn-1 Mutant

The double transgenic worms (Pmyo-2::V1S+Pflp-21::SV2-ICR-DsRed) were mated with dyn-1(ky51) mutant worms (Clark et al., 1997 A dynamin GTPase mutation causes a rapid and reversible temperature-inducible locomotion defect in C. elegans. Proc. Natl. Acad. Sci. USA 94, 10438-10443). Adult mother worms of the double transgenic line, with or without the dyn-1(ky51) mutation, were cultured on NGM plates containing E. coli OP50 at 20° C. for 4 h to lay eggs, and were then removed. Synchronized progeny worms of each strain at the L4-stage were cultured at 30° C. for observation.

Example 2-11. Fluorescence Microscopy of Live Worms

Worms were immobilized with 10 mM sodium azide in M9 buffer, mounted on 2% agar pads, and covered with a coverslip. Images of the worms were acquired using Olympus FV1000 confocal laser scanning microscopy (Olympus, Tokyo, Japan).

Example 2-12. Life Span Assay

Eggs laid by adult mother worms were synchronously grown up to the L4 larval stage on NGM plates seeded with E. coli OP50 at 20° C. The L4-stage worms were transferred to NGM plates containing 100 mM 5-fluoro-2'-deoxyuridine (Sigma) to prevent them from producing progeny. The number of worms that were alive or dead was recorded every 1-2 days.

Example 2-13. Pharyngeal Pumping Analysis

Pharyngeal pumping was counted for 1 min at RT using a fluorescence microscope. 25 worms from each strain were analyzed. The data were expressed as PPM (Pumps Per Minute).

Example 2-14. Anti-Aging Agent Treatment

N-acetylglucosamine (GlcNAc) (Sigma) was dissolved in distilled water to prepare 1 M as stock solution. The stock solution was diluted with LB liquid medium. The L4-stage worms of each transgenic line were transferred to NGM plates containing a final concentration of 10 mM GlcNAc.

Example 2-15. Western Blotting

Adult worms were washed with M9 buffer and subsequently with PBS containing 1% Triton X-100. The worm pellet was sonicated in PBS containing 1% Triton X-100, 1% (v/v) protease inhibitor cocktail (Sigma) and centrifuged to obtain the Triton-soluble (supernatant) and insoluble (pellet) fractions. Protein concentration was measured using the BCA protein assay kit (Pierce, Rockford, USA). Protein samples (3 μg for α-synuclein expression test and 50 μg to detect polyubiquitin proteins) were loaded onto 12% SDS-PAGE gels. The primary antibodies used for western blotting were monoclonal anti-α-synuclein antibody, 274 mAb and anti-ubiquitn antibody (ab7254; Abcam, Cambridge, Mass.). Chemiluminescence detection was performed using the LAS-3000 luminescence image analyzer, (Fujifilm, Tokyo, Japan), and Multi Gauge (y3.0) software.

Example 2-16. Dot Blotting

Adult worms of each strain were washed with M9 buffer and subsequently with PBS containing 1% Triton X-100. The worm pellet was sonicated in PBS containing 1% Triton X-100, 1% (v/v) protease inhibitor cocktail. Protein samples (500 ng) were loaded onto nitrocellulose membranes, which were then dried and incubated in blocking solution. The primary antibodies used for dot blotting were the monoclonal anti-α-synuclein antibodies 274 mAb and Syn-O2, the latter of which is specific for aggregated α-synuclein. Chemiluminescence detection was performed using the LAS-3000 luminescence image analyzer and Multi Gauge (v3.0) software.

Example 2-17. Quantitative PCR (qPCR)

Adult transgenic worms derived from daf-16(mu86) mutants with or without hlh-30p::hlh-30 expression were collected, and washed in M9 buffer. The worms in the buffer were sonicated and the samples were subjected to several freeze-thaw cycles using liquid nitrogen. RNA was extracted with Trizol (Invitrogen, Carlsbad, Calif.) and purified using the RNeasy kit (Qiagen, Valencia, Calif., USA). Each cDNA was synthesized from 500 ng of total RNA using the iScript cDNA synthesis kit (Bio-Rad, Hercules, Calif.). For real-time PCR, target genes and specific primers were mixed with SYBR Premix Ex Taq II (Takara, Shiga, Japan) in 96-well plates. Specific primers previously designed by other group were used (Lapierre, L. R., et al. (2013). The TFEB orthologue HLH-30 regulates autophagy and modulates longevity in Caenorhabditis elegans. Nat. Commun 4, 2267). The DNA products were analyzed using the 7500 Real-Time PCR system (Applied Biosystems, Foster City, Calif.). The DNA products were analyzed using the 7500 Real-Time PCR system (Applied Biosystems, Foster City, Calif.). Relative mRNA levels of target genes were normalized to act-1.

Example 2-18. Statistical Analysis

All experiments were performed blind-coded and repeated at least three times. The values are expressed as mean±S.E.M. Differences were considered significant ifp values were <0.05. The graphs were drawn using Prism 5 software (Graphpad Software Inc., La Jolla, Calif.). Values were compared by one-way ANOVA with Tukey's post-hoc test using InStat (version 3.05) software (Graphpad Software Inc.).

Experimental Results

Figure 23A:
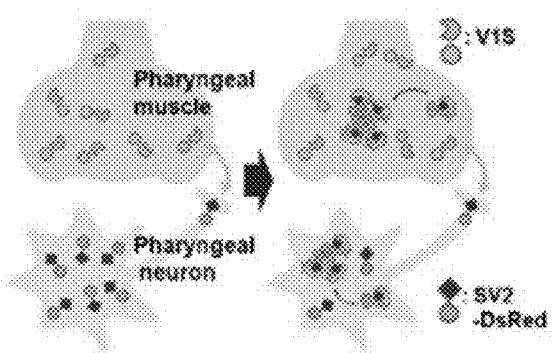
Figure 23B:
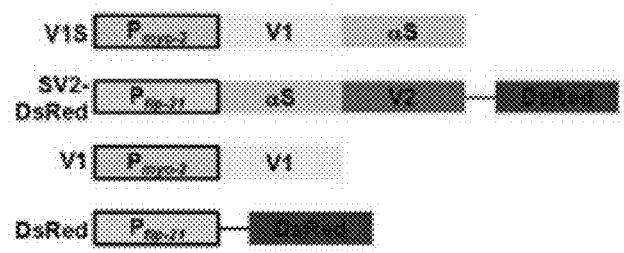
Figure 23C:
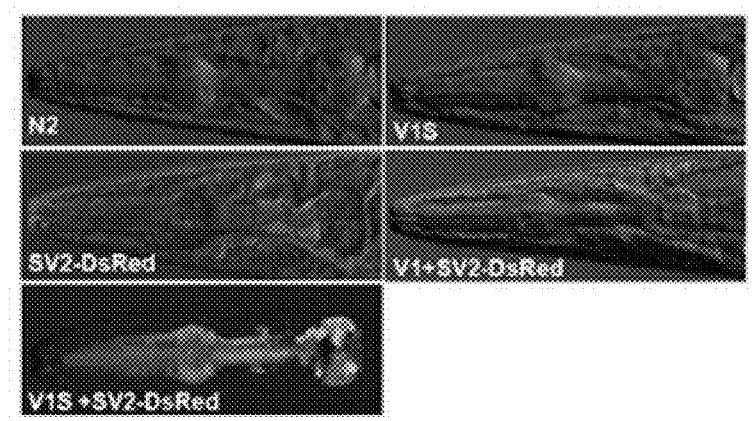
Figure 23D:
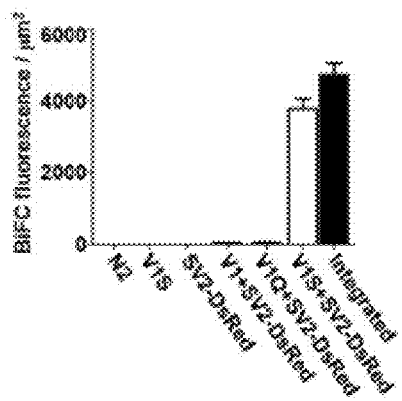

Experimental Result 2-1. Preparation and Characterization of C. elegans Model for Transmission of Synuclein In order to develop an animal model for convenient assay of cell-to-cell protein transmission, the present inventors prepared C. elegans transgenic lines expressing α-synuclein fused to the N terminal or C-terminal fragment of Venus, a variant of yellow fluorescence protein (FIG. 23a). The N-terminal part (V1) of Venus was attached to N-terminus (V1S) of α-synuclein, and the C-terminal part (V2) of Venus to C-terminus of α-synuclein (SV2). In the C. elegans model, V1S was expressed in the pharynx muscle using the myo-2 promoter (Pmyo-2), and SV2 and DsRed were co-expressed in neurons linked to the pharynx using the flp-21 promoter (Pflp-21) (FIG. 23b). The presence and expression of these transgenes were verified using single-worm PCR and immunofluorescence with the anti-α-synuclein antibody Ab274 ("A" to "D" of FIG. 28), verifying specific expressions of proteins exclusively in the intended cell types.

Expression pattern of Pflp-21 was described in (Rogers et al., 2003. Inhibition of Caenorhabditis elegans social feeding by FMRF amide-related peptide activation of NPR-1. Nat. Neurosci 6, 1178-1185), and the marker (Ds-Red) for flp-21 promoter activity also exhibited the same expression pattern, which includes expression in the ADL, ASE and ASH sensory neurons, the URA motor neurons, the MC, M2 and M4 pharyngeal neurons, and the intestine ("E" of FIG. 28).

Expression of V1S or SV2 alone did not produce BiFC fluorescence. However, coinjection of both constructs produced strong BiFC fluorescence in both the pharyngeal muscle and adjacent neurons, and the latter were labeled with DsRed (FIGS. 23c and 23d; "E" and "G" of FIG. 28). The experimental results indicated that protein transmission occurred in both directions. The co-expression of Pflp-21:: SV2-DsRed and Pmyo-2::V1 (without α-synuclein gene) did not produce a BiFC signal (FIGS. 23c and 23d; "E" of FIG. 28), indicating that the signal was not due to non-specific interactions between the Venus fragments. To test the specificity of the BiFC system, the present inventors prepared Pmyo-2::V1Q25+Pflp-21::SV2-DsRed lines. The transgenic worm expresses huntingtin exon 1 with a 25 glutamine stretch under the control of myo-2 promoter and SV2 in neurons. These worms did not exhibit a BiFC signal in the pharyngeal muscle or neurons (FIG. 23d; "E" of FIG. 28). This result validates that the BiFC transgenic worms are specific for α-synuclein transmission.

The present inventors also established integrated transgenic lines expressing V1S and SV2-DsRed respectively, and crossed them to create an integrated double transgenic line. As expected, neither V1S nor SV2-DsRed integrated line produced BiFC fluorescence, whereas the integrated double transgenic line showed strong BiFC fluorescence in both the pharyngeal muscle and adjacent neurons ("F" and "H" of FIG. 28). Thus, the C. elegans BiFC system can be utilized as an in vivo model in which both protein transfer and co-aggregation between α-synuclein proteins derived from adjacent cells can be accurately and quantitatively analyzed in real time.

Figure 23E:
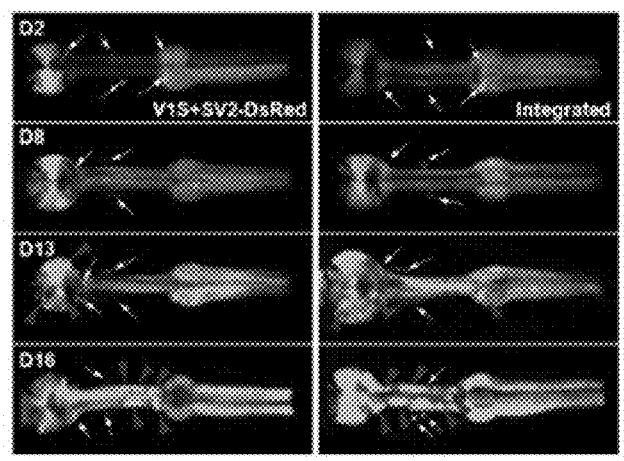
Figure 23F:
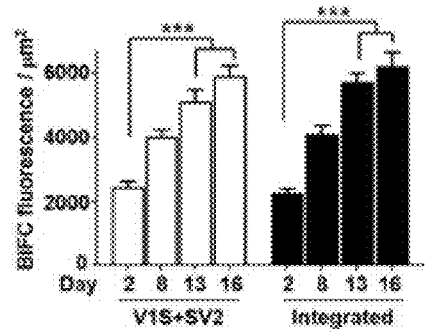
Figure 23G:
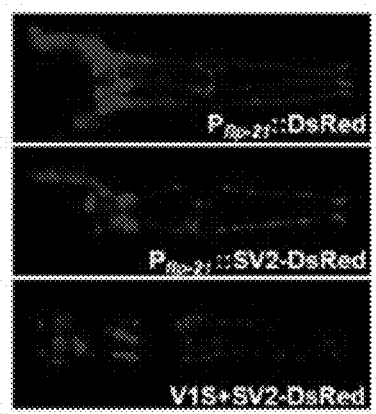

BiFC fluorescence increased as the worm aged (FIGS. 23e and 23f), and older animals showed clumps of BiFC signal while younger ones showed mostly diffuse patterns (FIG. 23e). These results indicate that α-synuclein transmission is a continuous process, and that the accumulated aggregates make larger inclusions later in life.

Figure 23H:
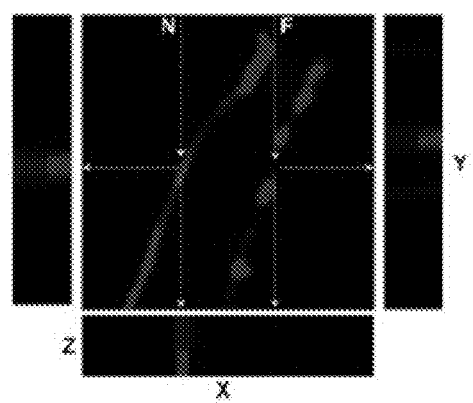
Figure 23I:
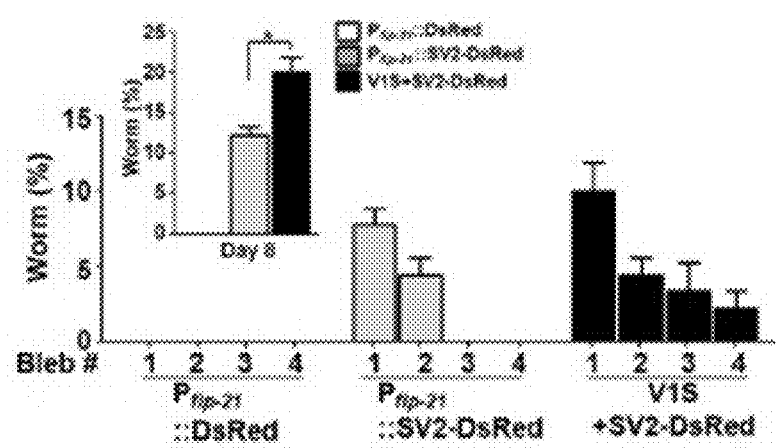
Figure 23J:
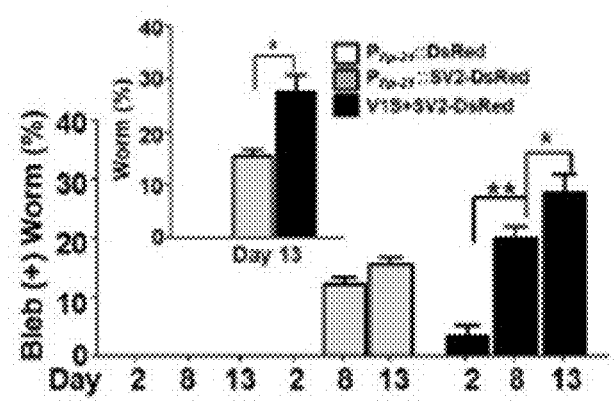
Figure 23K:
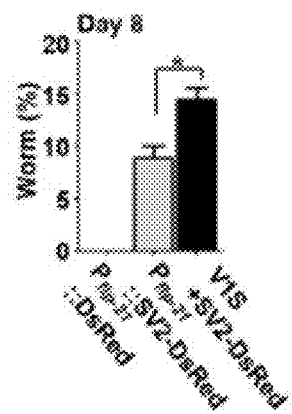
Figure 23L:
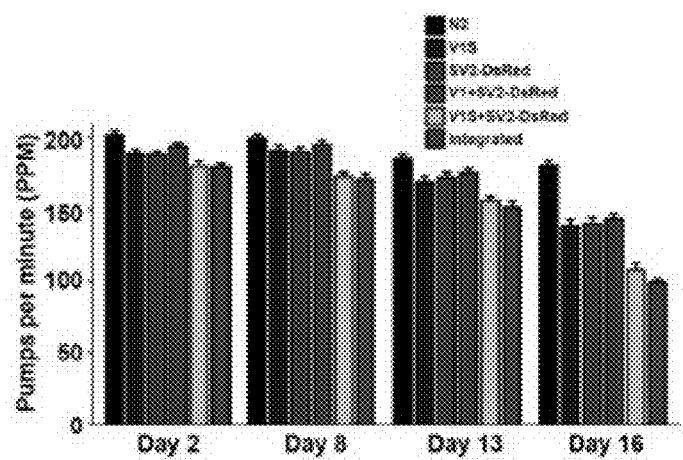

The present inventors then examined the degeneration of axonal processes from the URA motor neuron (Rogers et al., 2003). These nerves were intact in the wild-type N2 at day 8. Expression of SV2 in neurons caused neuritic bleb formation and nerve fragmentation in a small number of worms (FIGS. 23g, 23h, 23i, 23j, and 23k), indicating autonomous cellular toxicity of α-synuclein in neurons. These degenerative phenotypes were further exacerbated when V1S was expressed in the pharyngeal muscle, and approximately 15% of nerves were completely lost (FIG. 23k). To verify nerve fragmentation, 3-D reconstruction of the stacked images of nerve processes was performed. This experiment clearly exhibited nerve fragmentation and bleb formation (FIG. 23h). These results clearly demonstrate non-autonomous cellular effects on neuronal viability. Nerve degeneration worsened as the transgenic worms aged (FIG. 23j).

In order to assess behavioral changes due to the transmission of α-synuclein aggregates, the present inventors performed pharyngeal pumping analysis. The pumping rates of the wild-type N2 did not change significantly with aging until day 16. Single expression of V1S or SV2-DsRed in the pharyngeal muscle and adjacent neurons, respectively, resulted in a slight decline in pumping rates in old age. The reduction in pumping rates of all the single expressers became significant on day 13 (FIG. 23*l*; Table 1). Co-injection and double integrated lines showed more severe phenotypes for pumping rates, with the decline becoming apparent as early as day 2 and progressively deteriorating as the worms aged (FIG. 23*l*; Table 1). The following Table 1 shows P values of the pharyngeal pumping rates.

TABLE 1

| Day | | N2 | V1S | SV2::DsRed | V1 + SV2::DsRed | V1S + SV2::DsRed | Integrated |
|---|---|---|---|---|---|---|---|
| 2 | N2 | | p < 0.005 | p < 0.005 | ns | p < 0.001 | p < 0.001 |
| | V1S | p < 0.005 | | ns | ns | p < 0.005 | p < 0.005 |
| | SV2::DsRed | p < 0.005 | ns | | ns | p < 0.005 | p < 0.005 |
| | V1 + SV2::DsRed | ns | ns | ns | | p < 0.005 | p < 0.005 |
| | V1S + SV2::DsRed | p < 0.001 | p < 0.005 | p < 0.005 | p < 0.005 | | ns |
| | Integrated | p < 0.001 | p < 0.005 | p < 0.005 | p < 0.005 | ns | |
| 8 | N2 | | p < 0.05 | p < 0.05 | ns | p < 0.001 | p < 0.001 |
| | V1S | p < 0.05 | | ns | ns | p < 0.001 | p < 0.001 |
| | SV2::DsRed | p < 0.05 | ns | | ns | p < 0.001 | p < 0.001 |
| | V1 + SV2::DsRed | ns | ns | ns | | p < 0.001 | p < 0.001 |
| | V1S + SV2::DsRed | p < 0.001 | p < 0.001 | p < 0.001 | p < 0.001 | | ns |
| | Integrated | p < 0.001 | p < 0.001 | p < 0.001 | p < 0.001 | ns | |
| 13 | N2 | | p < 0.001 | p < 0.05 | p < 0.05 | p < 0.001 | p < 0.001 |
| | V1S | p < 0.005 | | ns | ns | p < 0.001 | p < 0.001 |
| | SV2::DsRed | p < 0.05 | ns | | ns | p < 0.001 | p < 0.001 |
| | V1 + SV2::DsRed | p < 0.05 | ns | ns | | p < 0.001 | p < 0.001 |
| | V1S + SV2::DsRed | p < 0.001 | p < 0.001 | p < 0.001 | p < 0.001 | | ns |
| | Integrated | p < 0.001 | p < 0.001 | p < 0.001 | p < 0.001 | ns | |
| 16 | N2 | | p < 0.001 | p < 0.001 | p < 0.001 | p < 0.001 | p < 0.001 |
| | V1S | p < 0.001 | | ns | ns | p < 0.001 | p < 0.001 |
| | SV2::DsRed | p < 0.001 | ns | | ns | p < 0.001 | p < 0.001 |
| | V1 + SV2::DsRed | p < 0.001 | ns | ns | | p < 0.001 | p < 0.001 |
| | V1S + SV2::DsRed | p < 0.001 | p < 0.001 | p < 0.001 | p < 0.001 | | ns |
| | Integrated | p < 0.001 | p < 0.001 | p < 0.001 | p < 0.001 | ns | |

Figure 23M:
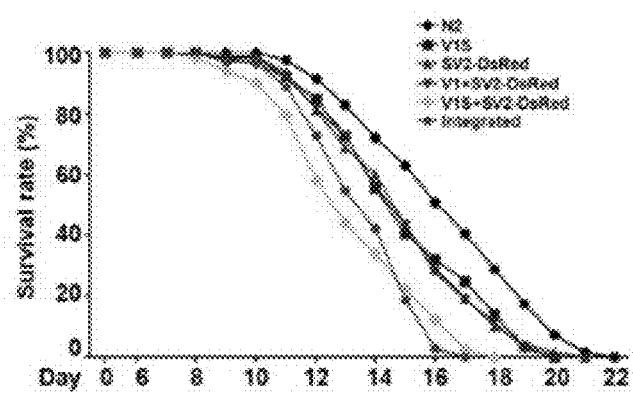

In longevity assays, the single transgenic animals showed a slightly decreased life span compared to the N2 wildtype, whereas the life span of the double transgenic animals was shorter than the single transgenic lines (FIG. 23*m*). Thus, aggregate transmission and inclusion body formation are associated with degenerative phenotypes, further progressing with aging. Comparison of the timelines indicates that death of the organism is preceded by the accumulation of BiFC signal, nerve degeneration, and a decline in pumping behavior. These results were replicated with the worms expressing non-tagged α-synuclein in the same cell types as the BiFC model ("I" to "L" of FIG. 28), suggesting that the phenotypes observed in the BiFC model is attributed to α-synuclein.

Experimental Result 2-2. Effects of Aging-Related Genetic Factors on Cell-to-Cell α-Synuclein Transmission The present inventors examined the effects of changes in aging rates on aggregate transmission and the degenerative phenotypes. The BiFC α-synuclein constructs were injected into daf-2(e1370) and daf-16(mu86) mutants ("A" and "B" of FIG. 29), which are models showing aging effects, with daf-2(e1370) mutants showing slower aging rate and extended life span while daf-16(mu86) mutants age faster than wild-type and have a shortened life span (Kenyon et al., 1993. A. *C. elegans* mutant that lives twice as long as wild type. Nature 366, 461-464). The daf-2(e1370); V1S+SV2 animals showed reduced BiFC signal (FIGS. 24*a* and 24*b*; "D" of FIG. 29), smaller number of inclusion bodies (FIGS. 24*c* and 24*d*; "E" of FIG. 29), less nerve degeneration (FIGS. 24*e* and 24*f*; "F" and "G" of FIG. 29), increased pumping behavior (FIG. 24*g*; "H" of FIG. 29), and extended life span than the V1S+SV2 line (FIG. 24*h*; "I" of FIG. 29). On the other hand, in the daf-16(mu86); V1S+SV2 animals, BiFC-positive inclusion bodies appeared much earlier than in the V1S+SV2 animals; as early as 2-days post the L4-stage (FIGS. 24*c* and 24*d*; "E" of FIG. 29). The BiFC signal itself was lower in the daf-16(mu86); V1S+SV2 than in the V1S+SV2 (FIG. 24*b*; "D" of FIG. 29), probably due to early and robust formation of inclusion bodies. The daf-16(mu86); V1S+SV2 animals showed more severe nerve degeneration (FIGS. 24*e* and 24*f*; "F" and "G" of FIG. 29), more decreased pumping behavior (FIG. 24*g*; "H" of FIG. 29), and shorter life span than the V1S+SV2 animals (FIG. 24*h*; "I" of FIG. 29). Similar results were obtained in three independent lines for each genotype. These results indicate that aging is the major factor regulating the rate of cell-to-cell transmission of α-synuclein aggregates and the associated degenerative phenotypes in vivo.

Figure 25H:
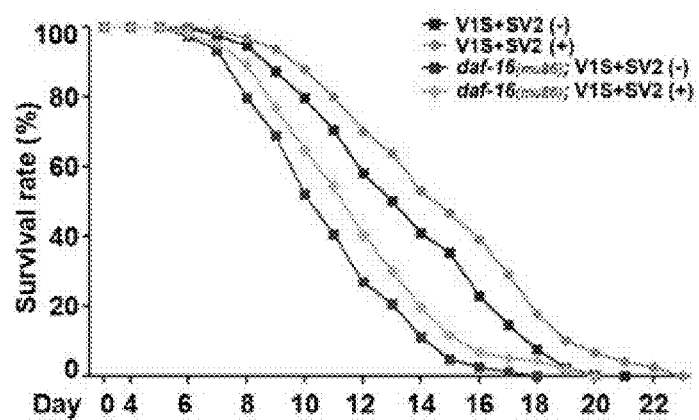

Experimental Result 2-3. Effects of Anti-Aging Treatment on Cell-to-Cell Transmission of α-Synuclein Transmission The present inventors then measured the effects of the anti-aging agent, N-acetylglucosamine (GlcNAc) (Denzel M. S., et al., 2014. Hexosamine pathway metabolites enhance protein quality control and prolong life. Cell 156, 1167-1178), on aggregate transmission. When GlcNAc was administered to the V1S+SV2 and daf-16(mu86); V1S+SV2 animals, both animals showed reduced formation of BiFC-positive inclusion bodies (FIGS. 25a and 25b) and significantly alleviated phenotypes for nerve degeneration (FIGS. 25c, 25d, 25e, and 25f), pumping behavior (FIG. 25g), and life span (FIG. 25h). These results suggest that anti-aging treatments can slow the progress of synucleinopathy.

Figure 26A:
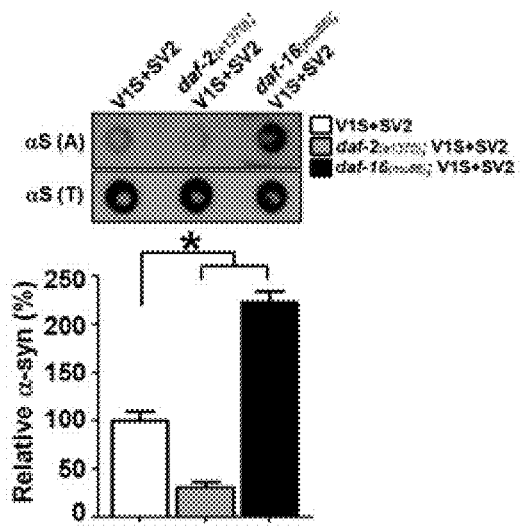
Figure 26B:
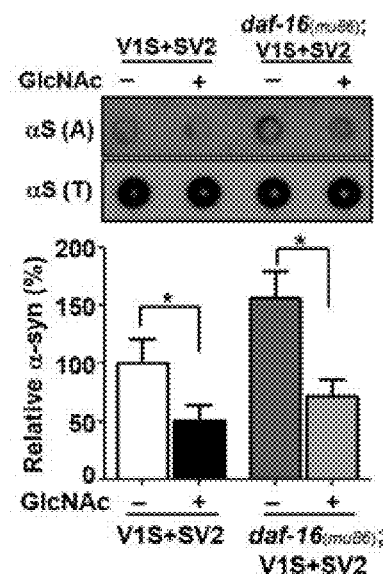
Figure 26C:
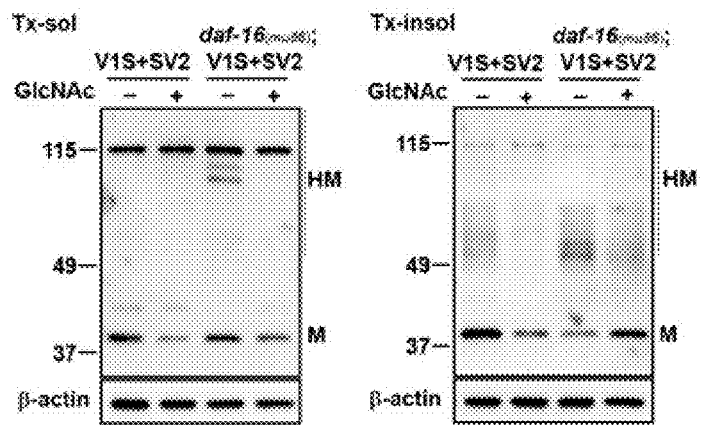
Figure 26D:
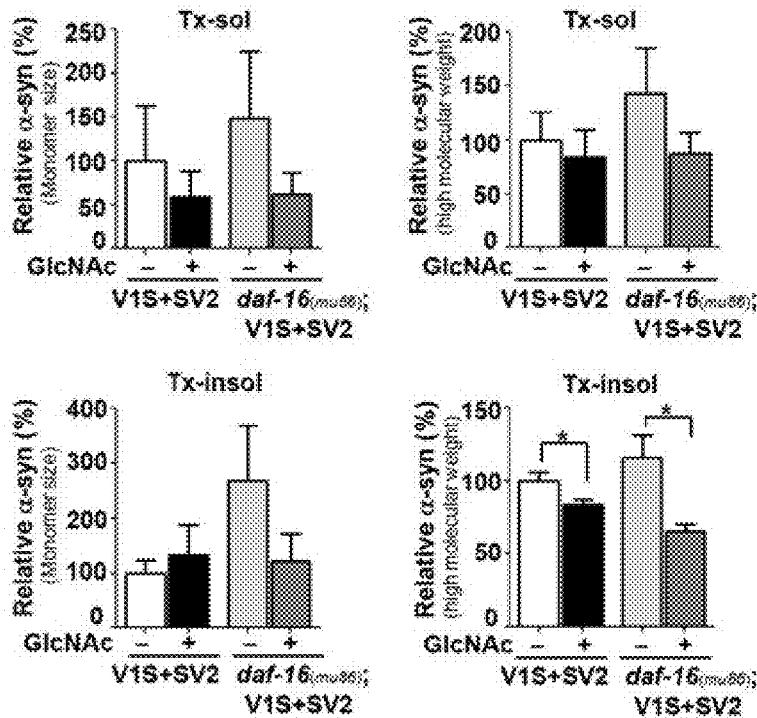
Figure 26E:
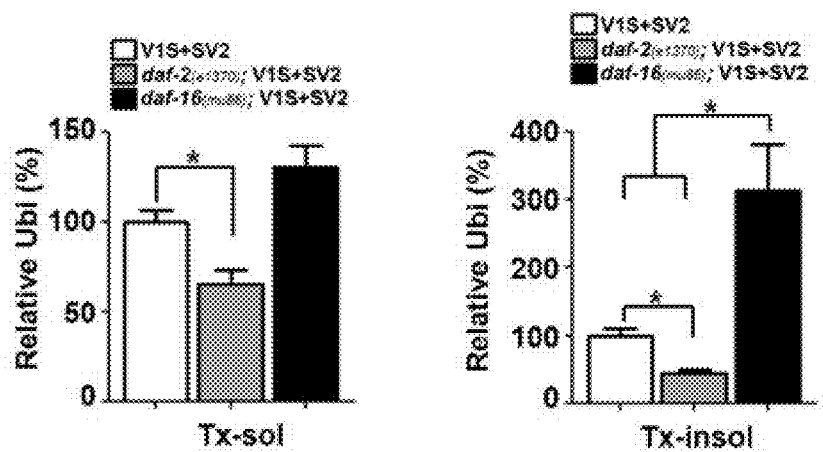
Figure 26F:
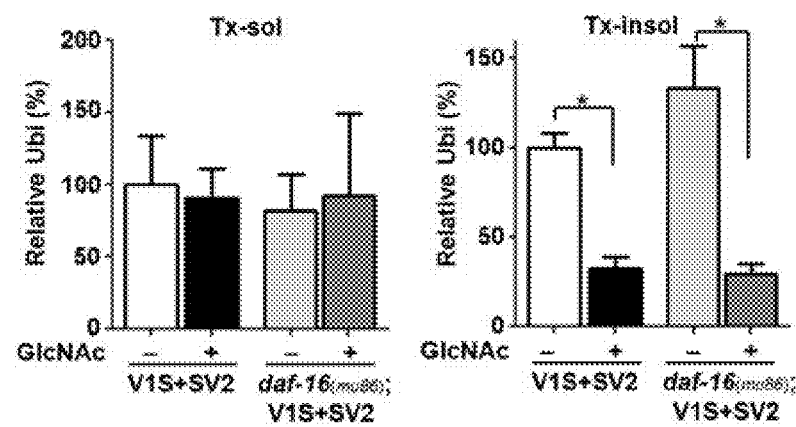

Experimental Result 2-4. Changes in Steady-State Levels of Polyubiquitinated Proteins by Anti-Aging Treatment To confirm the microscopic data for changes in the levels of aggregates, a dot blot analysis was performed with an antibody specific to β-sheet-rich α-synuclein multimers (Syn-02). Consistent with the BiFC inclusion analysis, the dot blot analysis showed that β-sheet-rich α-synuclein aggregates were reduced by the daf-2 mutation and by GlcNAc, whereas the daf-16 mutation increased the aggregates (FIGS. 26a and 26b). Furthermore, treatment of anti-aging agent significantly decreased the levels of high molecular weight (HM) α-synuclein aggregates in the Triton-insoluble (Tx-insol) fraction of transgenic worms (FIGS. 26c and 26d).

Aging causes a progressive decline in protein homeostasis (Denzel et al., 2014; Lapierre et al., 2013). This led the present inventors to examine the steady state levels of polyubiquitinated proteins, which represent the activities of major protein degradation systems, such as the ubiquitin-proteasome system and autophagy. The levels of polyubiquitinated proteins were increased in the daf-16 transgenic animals, while they were decreased in the daf-2 transgenic animals (FIG. 26e; "A" of FIG. 31). Similarly, the treatment of animals with GlcNAc decreased the levels of polyubiquitinated proteins (FIG. 26f; "B" of FIG. 31). These results suggest that the effects of aging and anti-aging treatments on the propagation of synucleinopathy are mediated by the changes in the capacity of protein degradation systems.

Experimental Result 2-5. The Endolysosomal Pathway in α-Synuclein Transmission

Figure 26G:
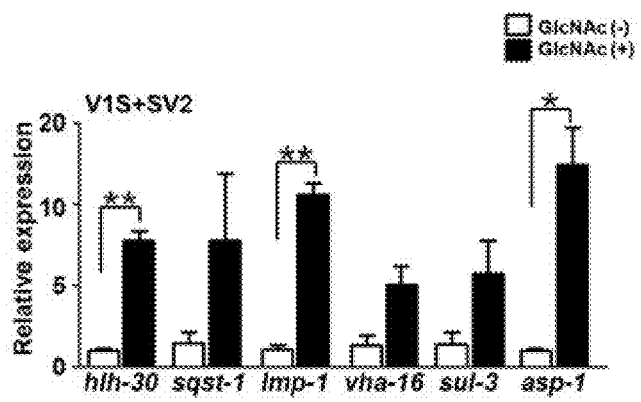
Figure 26H:
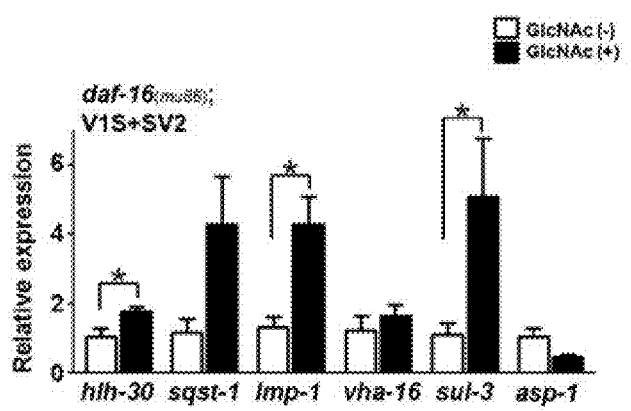

Previous studies in cell models have shown that cell-to-cell transmission of α-synuclein is mediated by endocytosis, and the transferred proteins are delivered to lysosomes for degradation (Hansen, C., et al. 2011. alph-Synuclein propagates from mouse brain to grafted dopaminergic neurons and seeds aggregation in cultured human cells. J. Clin. Invest 121, 715-725; Desplats, P., et al. 2009. Inclusion formation and neuronal cell death through neuron-to neuron transmission of alpha-synuclein. Proc. Natl. Acad. Sci. USA 106, 13010-13015). When V1S+SV2 was introduced into dynamin mutants, dyn-1(ky51) (Clark S. G. et al., 1997. A dynamin GTPase mutation causes a rapid and reversible temperature-inducible locomotion defect in C. elegans Proc. Natl. Acad. Sci. USA 10438-10443), BiFC fluorescence was significantly reduced compared to that in wild-type (FIGS. 27a and 27b). Reduction of the BiFC signal in the dyn-1 (ky51) transgenic animals was greater at day 5 than at day 2, suggesting that the effect was cumulative. Example 1 and the previous studies of the present inventors showed that lysosomal function is important for clearing the "seeds" in the process of cell-to-cell transmission of α-synuclein, and lysosomal dysfunction resulted in enhancement of aggregate transmission. Consistent with these studies, when V1S+SV2 was introduced into asp-4(ok2693) and asp-1(tm666) mutants, mutations in cathepsin genes (Syntichaki, P., et al., 2002. Specific aspartyl and calpain proteases are required for neurodegeneration in C. elegans. Nature 419, 939-944), BiFC fluorescence was significantly increased in both mutants, often in the form of inclusion bodies (FIGS. 27c, 27d, and 27e; "D" and "E" of FIG. 31). These results suggest that lysosomal responses are crucial for protecting the animals from age-dependent aggregate propagation. Consistent with this interpretation, GlcNAc treatment increased the expression of lysosomal genes as well as the gene involved in autophagy, sqst-1/p62 (FIGS. 26g and 26h). This was further validated by epistasis analysis, where asp-4(ok2693); V1S+SV2 and asp-1(tm666); V1S+SV2 worms were treated with GlcNAc. In contrast to the V1S+SV2 worms, aging-related phenotypes were not rescued by GlcNAc treatment in the asp-1 and asp-4 mutant transgenic animals (FIGS. 27f and 27g)

Experimental Result 2-6. The Effects of Anti-Aging Treatments on Aggregate Transmission Associated with Enhanced Lysosomal Function To verify the role of lysosome in protection against aggregate propagation, the hlh-30 transgenic lines overexpressing the vector hlh-30p::hlh-30, an ortholog of TFEB, the master control transcription factor for lysosome biogenesis into the daf-16(mu86); V1S+SV2 transgenic animals (Lapierre et al., 2013; Sardiello et al., 2009. A gene network regulating lysosomal biogenesis and function. Science 325, 473-477). In addition to lysosomal and autophagic genes, down-stream target genes for HLH-30 include genes involved in metabolism, apoptosis, and signaling (ref). Expression of hlh-30p::hlh-30 in the daf-16(mu86); V1S+SV2 animals increased autophagy-related and lysosomal gene induction, such as sqst-1, asp-1, (FIG. 27h) and reduced the formation of α-synuclein aggregates (FIG. 27i) and the steady state levels of polyubiquitinated proteins (FIG. 27j; "C" of FIG. 31), which indicate the restoration of protein degradation. The hlh-30 transgenic lines showed reduced BiFC signal (hence, reduced aggregate propagation), decreased nerve degeneration, increased pumping rates, and increased life-span (FIGS. 27k, 27l, 27m, 27n, 27o, 27p, 27q, and 27r; "L" to "O" of FIG. 32).

Experimental Result 2-7. Cell-Autonomous Aggregation Vs. Intercellular Transmission The results above do not present differentiation between intercellular aggregate transmission and cell-autonomous aggregation. To address this issue, the present inventors have prepared four transgenic lines expressing V1S or SV2 alone in N2 and daf-16(mu86) mutant worms. Also two transgenic worms overexpressing hlh-30p::hlh-30 transgene with V1S or SV2 were prepared. Expression levels were normalized with single worm PCR and western analysis (in case of V1S lines) or Ds-Red fluorescence (in case of SV2 lines). Nerve degeneration, pumping behavior, and life span of the transgenic worms in mutant backgrounds were compared with the ones in normal genetic backgrounds. As a result, no significant differences were found in the phenotypes (FIG. 30; "D" to "G" of FIG. 31), suggesting the genetic modification the present inventors investigated do not have a large impact on α-synuclein aggregation in the respective tissues.

The present inventors also treated the single tissue expression lines carrying V1S or SV2 alone in N2 and daf-16

(mu86) mutant worms with GlcNAc and compared the same battery of phenotypic assays with untreated animals. Unlike the transmission models, the single tissue expression lines did not exhibit significant changes in pathogenic phenotypes upon treatment with GlcNAc ("D" to "M" of FIG. 30). To examine the effects of GlcNAc on the expression levels of α-synuclein, the levels of α-synuclein by dot blot were measured ("N", "O" and "P" of FIG. 30). The result showed that the expression levels were not changed by GlcNAc treatment. The present inventors also examined neuronal expression of flp-21 promoter upon GlcNAc treatment by monitoring Ds-Red. Expression of Ds-Red was strictly confined in neuronal cells with or without GlcNAc treatment ("Q" of FIG. 30), indicating that the treatment does not change the cell-type specificity of the promoter.

These results suggest that the anti-aging and pro-lysosomal treatments used in the present disclosure exert their effects on cell-to-cell transmission of aggregate.

The transgenic neuroblastoma cell lines have been deposited with Korean Cell Line Research Foundation (KCLRF) having the address of Cancer Research Institute, Seoul National University, College of Medicine, 28 Yungon-dong, Chongno-gu, Seoul 110-799, Republic of Korea, under the Access numbers of KCLRFBP00322 and KCLRFBP00323, respectively, on Aug. 26, 2014. The deposits have been made under the terms of the Budapest Treaty and all restrictions imposed by the depositor on the availability to the public of the biological material will be irrevocably removed upon the granting of a patent. The Deposit will be maintained in a public depository for a period of thirty years after the date of deposit or five years after the last request for a sample or for the effective life of the patent, whichever is longer. The above-referenced cell line was viable at the time of the deposit. The deposit will be replaced if viable samples cannot be dispensed by the depository. The material has been deposited under conditions that ensure that access to the material will be available during the pendency of the patent application to one determined by the Commissioner to be entitled thereto under 35 C.F.R. §1.14 and 35 U.S.C. §122.

The present disclosure is described with reference to the above embodiments. It should be appreciated by those skilled in the art that various changes and modifications may be made to the embodiments without departing from the scope of the present disclosure. Thus, the described embodiments set forth above are intended solely for explanatory purposes, not for limiting the present disclosure. The scope of the present disclosure is defined by the claims below. It should be appreciated that the present disclosure is not limited to the above embodiments, and all changes and/or equivalents thereto also belong to the scope of the present disclosure.

What is claimed is:

1. A method for measuring cell-to-cell transmission of α-synuclein aggregates using a cell system comprising a first cell expressing a first fusion protein where an N-terminal fragment of a fluorescent protein and α-synuclein are fused; and a second cell expressing a second fusion protein where a C-terminal fragment of the fluorescent protein and α-synuclein are fused, the method comprising:
co-expressing the first fusion protein and the second fusion protein in the first cell and the second cell, respectively, through co-culture of the first cell and the second cell; and
quantitatively detecting, in the first cell and the second cell, a bimolecular fluorescence complementation (BiFC) fluorescent signal generated by linking the N-terminal fragment and the C-terminal fragment of the fluorescent protein, to analyze cell-to-cell transfer and co-aggregation of α-synuclein proteins derived from adjacent cells,
wherein the cell model system includes a transgenic neuroblastoma cell line having Accession No. KCLRF-BP-00322 as the first cell and a transgenic neuroblastoma cell line having Accession No. KCLRF-BP-00323 as the second cell.

2. The method of claim 1, further comprising:
mixing the first cell and the second cell in a culture medium and subculturing the mixture; and
measuring the percentage of a BiFC-positive cell in the subculture.

3. The method of claim 1, wherein the fluorescent protein is Venus, the first fusion protein is encoded by a polynucleotide having a nucleotide sequence represented by SEQ ID NO: 4, and the second fusion protein is encoded by a polynucleotide having a nucleotide sequence represented by SEQ ID NO: 5.

4. A method for screening a substance for preventing or treating a neurodegenerative disease associated with α-synuclein aggregation, using the method of claim 1, the method comprising:
increasing or decreasing an expression level of a candidate gene expressed in the first cell and the second cell of the cell system; and
measuring a change in a bimolecular fluorescence complementation (BiFC) fluorescent signal based on a change in the expression level of the candidate gene, to analyze association between the candidate gene and the cell-to-cell transmission of α-synuclein aggregates.

5. A method for screening a substance for preventing or treating a neurodegenerative disease associated with α-synuclein aggregation, using the method of claim 1, the method comprising:
treating a test substance in the cell;
measuring a change in a bimolecular fluorescence complementation (BiFC) fluorescent signal according to the treatment of the test substance; and
when the BiFC fluorescent signal is reduced, determining the test substance as a substance for preventing or treating the neurodegenerative disease.

6. The method of claim 5, wherein the measuring of the change in the BiFC fluorescent signal according to the treatment of the test substance comprises measuring a change in the BiFC fluorescent signal according to aging of the cell.

7. The method of claim 5, wherein the cell completely or partially absent from lysosomal function.

8. The method of claim 4, wherein the candidate gene is a gene associated with aging.

9. The method of claim 5, wherein the test substance has an anti-aging activity.

10. The method of claim 5, wherein the neurodegenerative disease associated with the α-synuclein aggregation is Parkinson's disease.

* * * * *

SEQUENCE LISTING

```
<160> NUMBER OF SEQ ID NOS: 25

<210> SEQ ID NO 1
<211> LENGTH: 158
<212> TYPE: PRT
<213> ORGANISM: Artificial Sequence
<220> FEATURE:
<223> OTHER INFORMATION: Venus 1-158 amino acid

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln
145                 150                 155

<210> SEQ ID NO 2
<211> LENGTH: 91
<212> TYPE: PRT
```

<213> ORGANISM: Artificial Sequence
<220> FEATURE:
<223> OTHER INFORMATION: Venus 159 to 239 amino acid

<400> SEQUENCE: 2

```
Lys Asn Gly Ile Lys Ala Asn Phe Lys Ile Arg His Asn Ile Glu Asp
1               5                   10                  15

Gly Gly Val Gln Leu Ala Asp His Tyr Gln Gln Asn Thr Pro Ile Gly
            20                  25                  30

Asp Gly Pro Val Leu Leu Pro Asp Asn His Tyr Leu Ser Tyr Gln Ser
        35                  40                  45

Ala Leu Ser Lys Asp Pro Asn Glu Lys Arg Asp His Met Val Leu Leu
    50                  55                  60

Glu Phe Val Thr Ala Ala Gly Ile Thr Leu Gly Met Asp Glu Leu Tyr
65                  70                  75                  80

Lys Gly Ala Trp Ser His Pro Gln Phe Glu Lys
                85                  90
```

<210> SEQ ID NO 3
<211> LENGTH: 140
<212> TYPE: PRT
<213> ORGANISM: Homo sapiens

<400> SEQUENCE: 3

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 4
<211> LENGTH: 933
<212> TYPE: DNA
<213> ORGANISM: Artificial Sequence
<220> FEATURE:
<223> OTHER INFORMATION: Venus1 linker alphaSyn fusion protein

<400> SEQUENCE: 4

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
```

```
ttcaaggacg acggcaacta caagacccgc gccgaggtga agttcgaggg cgacaccctg    360
gtgaaccgca tcgagctgaa gggcatcgac ttcaaggagg acggcaacat cctgggcac    420 aagctggagt acaactacaa cagccacaac gtctatatca ccgccgacaa gcaaatcgat    480
ggtggcggtg gctctggagg tgtgggtcc cttaaggatg tattcatgaa aggactttca    540
aaggccaagg agggagttgt ggctgctgct gagaaaacca acagggtgt ggcagaagca    600 gcaggaaaga caaagagggg tgttctctat gtaggctcca aaaccaagga gggagtggtg    660
catggtgtgg caacagtggc tgagaagacc aaagagcaag tgacaaatgt tggaggagca    720
gtggtgacgg tgtgtgacagc agtagcccag aagacagtgg agggagcagg gagcattgca    780
gcagccactg gctttgtcaa aaaggaccag ttgggcaaga atgaagaagg agccccacag    840
gaaggaattc tggaagatat gcctgtggat cctgacaatg aggcttatga aatgccttct    900
gaggaagggt atcaagacta cgaacctgaa gcc                                 933

<210> SEQ ID NO 5
<211> LENGTH: 673
<212> TYPE: DNA
<213> ORGANISM: Artificial Sequence
<220> FEATURE:
<223> OTHER INFORMATION: alphaSyn Venus2 fusion protein

<400> SEQUENCE: 5
atggatgtat tcatgaaagg actttcaaag gccaaggagg gagttgtggc tgctgctgag     60
aaaaccaaac agggtgtggc agaagcagca ggaaagacaa agagggtgt tctctatgta    120 ggctccaaaa ccaaggaggg agtggtgcat ggtgtggcaa cagtggctga aagaccaaa    180 gagcaagtga caaatgttgg aggagcagtg gtgacgggtg tgacagcagt agcccagaag    240
acagtggagg gagcagggag cattgcagca gccactggct ttgtcaaaaa ggaccagttg    300
ggcaagaatg aagaaggagc cccacaggaa ggaattctgg aagatatgcc tgtggatcct    360
gacaatgagg cttatgaaat gccttctgag gaagggtatc aagactacga acctgaagcc    420
ctcgaggaag aacggcatca aggccaactt caagatccgc cacaacatcg aggacggcgg    480
cgtgcagctc gccgaccact accagcagaa caccccatc ggcgacggcc ccgtgctgct    540
gcccgacaac cactacctga gctaccagtc caagctgagc aaagacccca cgagaagcg    600 cgatcacatg gtcctgctgg agttcgtgac cgccgccggg atcactctcg gcatggacga    660
gctgtacaag taa                                                       673

<210> SEQ ID NO 6
<211> LENGTH: 31
<212> TYPE: DNA
<213> ORGANISM: Artificial Sequence
<220> FEATURE:
<223> OTHER INFORMATION: Artificial Sequence

<400> SEQUENCE: 6
gacaagcttg ggttttgtg ctgtggacgt t                                    31

<210> SEQ ID NO 7
<211> LENGTH: 30
<212> TYPE: DNA
<213> ORGANISM: Artificial Sequence
<220> FEATURE:
<223> OTHER INFORMATION: Artificial Sequence

<400> SEQUENCE: 7
gacggatcct tctgtgtctg acgatcgagg                                     30
```

<210> SEQ ID NO 8
<211> LENGTH: 37
<212> TYPE: DNA
<213> ORGANISM: Artificial Sequence
<220> FEATURE:
<223> OTHER INFORMATION: Artificial Sequence

<400> SEQUENCE: 8
agcgtcgacg ccaccatgga tgtattcatg aaaggac                      37

<210> SEQ ID NO 9
<211> LENGTH: 63
<212> TYPE: DNA
<213> ORGANISM: Artificial Sequence
<220> FEATURE:
<223> OTHER INFORMATION: Artificial Sequence

<400> SEQUENCE: 9
agcagatctc tacagatcct cttcagagat gagtttctgc tcggcttcag gttcgtagtc    60
ttg                                                                  63

<210> SEQ ID NO 10
<211> LENGTH: 34
<212> TYPE: DNA
<213> ORGANISM: Artificial Sequence
<220> FEATURE:
<223> OTHER INFORMATION: Artificial Sequence

<400> SEQUENCE: 10
agcgtcgacg ccaccatggt gagcaaggcc gagg                         34

<210> SEQ ID NO 11
<211> LENGTH: 30
<212> TYPE: DNA
<213> ORGANISM: Artificial Sequence
<220> FEATURE:
<223> OTHER INFORMATION: Artificial Sequence

<400> SEQUENCE: 11
agcagatctt taggcttcag gttcgtagtc                              30

<210> SEQ ID NO 12
<211> LENGTH: 35
<212> TYPE: DNA
<213> ORGANISM: Artificial Sequence
<220> FEATURE:
<223> OTHER INFORMATION: Artificial Sequence

<400> SEQUENCE: 12
agcactagtg ccaccatgga tgtattcatg aaagg                        35

<210> SEQ ID NO 13
<211> LENGTH: 33
<212> TYPE: DNA
<213> ORGANISM: Artificial Sequence
<220> FEATURE:
<223> OTHER INFORMATION: Artificial Sequence

<400> SEQUENCE: 13
agcagatctt acttgtacag ctcgtccatg ccg                          33

<210> SEQ ID NO 14
<211> LENGTH: 31
<212> TYPE: DNA

```
<213> ORGANISM: Artificial Sequence
<220> FEATURE:
<223> OTHER INFORMATION: Artificial Sequence

<400> SEQUENCE: 14
agcggtacca actaggtcca gtgaccgaaa g                              31

<210> SEQ ID NO 15
<211> LENGTH: 37
<212> TYPE: DNA
<213> ORGANISM: Artificial Sequence
<220> FEATURE:
<223> OTHER INFORMATION: Artificial Sequence

<400> SEQUENCE: 15
agcgtcgacg ccaccatgga tgtattcatg aaaggac                        37

<210> SEQ ID NO 16
<211> LENGTH: 37
<212> TYPE: DNA
<213> ORGANISM: Artificial Sequence
<220> FEATURE:
<223> OTHER INFORMATION: Artificial Sequence

<400> SEQUENCE: 16
agcgtcgacg ccaccatgga tgtattcatg aaaggac                        37

<210> SEQ ID NO 17
<211> LENGTH: 34
<212> TYPE: DNA
<213> ORGANISM: Artificial Sequence
<220> FEATURE:
<223> OTHER INFORMATION: Artificial Sequence

<400> SEQUENCE: 17
cgatcatttt ggagattact tgtacagctt gtcc                           34

<210> SEQ ID NO 18
<211> LENGTH: 34
<212> TYPE: DNA
<213> ORGANISM: Artificial Sequence
<220> FEATURE:
<223> OTHER INFORMATION: Artificial Sequence

<400> SEQUENCE: 18
ggacgagctg tacaagtaat ctccaaaatc atcg                           34

<210> SEQ ID NO 19
<211> LENGTH: 32
<212> TYPE: DNA
<213> ORGANISM: Artificial Sequence
<220> FEATURE:
<223> OTHER INFORMATION: Artificial Sequence

<400> SEQUENCE: 19
agcactagtt accctgtaat aatatattaa ac                             32

<210> SEQ ID NO 20
<211> LENGTH: 28
<212> TYPE: DNA
<213> ORGANISM: Artificial Sequence
<220> FEATURE:
<223> OTHER INFORMATION: zinc-finger nuclease target sequence

<400> SEQUENCE: 20
ttcgacgtgt agccagggcc atcaccca                                  28
```

<210> SEQ ID NO 21
<211> LENGTH: 28
<212> TYPE: DNA
<213> ORGANISM: Artificial Sequence
<220> FEATURE:
<223> OTHER INFORMATION: frame-shift mutation in two alleles of GBA1
      gene in SV2 cells

<400> SEQUENCE: 21
ttcgacgtgt agccagggcc atcaccca                                          28

<210> SEQ ID NO 22
<211> LENGTH: 24
<212> TYPE: DNA
<213> ORGANISM: Artificial Sequence
<220> FEATURE:
<223> OTHER INFORMATION: frame-shift mutation in two alleles of GBA1
      gene in SV2 cells

<400> SEQUENCE: 22
ttcgacgtgt aggtccatca ccca                                              24

<210> SEQ ID NO 23
<211> LENGTH: 29
<212> TYPE: DNA
<213> ORGANISM: Artificial Sequence
<220> FEATURE:
<223> OTHER INFORMATION: frame-shift mutation in two alleles of GBA1
      gene in SV2 cells

<400> SEQUENCE: 23
ttcgacgtgg gatccgcggc catcaccca                                         29

<210> SEQ ID NO 24
<211> LENGTH: 933
<212> TYPE: DNA
<213> ORGANISM: Artificial Sequence
<220> FEATURE:
<223> OTHER INFORMATION: nucleotide sequence of fusion proteins V1S
      (Venus1-alphaSyn)

<400> SEQUENCE: 24
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagct gatctgcacc accggcaagc tgcccgtgcc ctggcccacc       180
ctcgtgacca ccctgggcta cggcctgcag tgcttcgccc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca ccgccgacaa gcaaatcgat       480
ggtggcggtg gctctggagg tggtgggtcc cttaaggatg tattcatgaa aggactttca       540
aaggccaagg agggagttgt ggctgctgct gagaaaacca acagggtgt ggcagaagca       600 gcaggaaaga caaagaggg tgttctctat gtaggctcca aaaccaagga gggagtggtg       660
catggtgtgg caacagtggc tgagaagacc aaagagcaag tgacaaatgt ggaggagca       720 gtggtgacgg gtgtgacagc agtagcccag aagacagtgg agggagcagg gagcattgca       780
gcagccactg gctttgtcaa aaaggaccag ttgggcaaga atgaagaagg agcccccacag      840

```
gaaggaattc tggaagatat gcctgtggat cctgacaatg aggcttatga aatgccttct      900
gaggaagggt atcaagacta cgaacctgaa gcc                                  933

<210> SEQ ID NO 25
<211> LENGTH: 673
<212> TYPE: DNA
<213> ORGANISM: Artificial Sequence
<220> FEATURE:
<223> OTHER INFORMATION: nucleotide sequence of fusion proteins SV2
      (alphaSyn-Venus2)

<400> SEQUENCE: 25
atggatgtat tcatgaaagg actttcaaag gccaaggagg gagttgtggc tgctgctgag       60
aaaaccaaac agggtgtggc agaagcagca ggaaagacaa aagagggtgt tctctatgta      120
ggctccaaaa ccaaggaggg agtggtgcat ggtgtggcaa cagtggctga aagaccaaa       180 gagcaagtga caaatgttgg aggagcagtg gtgacgggtg tgacagcagt agcccagaag      240
acagtggagg gagcagggag cattgcagca gccactggct ttgtcaaaaa ggaccagttg      300
ggcaagaatg aagaaggagc cccacaggaa ggaattctgg aagatatgcc tgtggatcct      360
gacaatgagg cttatgaaat gccttctgag gaagggtatc aagactacga acctgaagcc      420
ctcgaggaag aacggcatca aggccaactt caagatccgc cacaacatcg aggacggcgg      480
cgtgcagctc gccgaccact accagcagaa cacccccatc ggcgacggcc ccgtgctgct      540
gcccgacaac cactacctga gctaccagtc caagctgagc aaagacccca acgagaagcg      600
cgatcacatg gtcctgctgg agttcgtgac cgccgccggg atcactctcg gcatggacga      660
gctgtacaag taa                                                       673
```